US011559556B2

(12) United States Patent
Medina Cruz et al.

(10) Patent No.: US 11,559,556 B2
(45) Date of Patent: Jan. 24, 2023

(54) CITRUS FRUIT EXTRACT-MEDIATED SYNTHESIS OF TELLURIUM NANOMATERIALS HAVING BIOMEDICAL APPLICATIONS

(71) Applicant: Northeastern University, Boston, MA (US)

(72) Inventors: David Medina Cruz, Boston, MA (US); William Tien-Street, Boston, MA (US); Bohan Zhang, Malden, MA (US); Xinjing Huang, Boston, MA (US); Ada Vernet Crua, Boston, MA (US); Thomas J. Webster, Barrington, RI (US)

(73) Assignee: Northeastern University, Boston, MA (US)

( * ) Notice: Subject to any disclaimer, the term of this patent is extended or adjusted under 35 U.S.C. 154(b) by 236 days.

(21) Appl. No.: 16/817,856

(22) Filed: Mar. 13, 2020

(65) Prior Publication Data
US 2020/0289600 A1  Sep. 17, 2020

Related U.S. Application Data

(60) Provisional application No. 62/819,445, filed on Mar. 15, 2019.

(51) Int. Cl.
*A61K 9/51* (2006.01)
*A61K 33/04* (2006.01)
*A61K 36/752* (2006.01)

(52) U.S. Cl.
CPC .......... *A61K 36/752* (2013.01); *A61K 9/5115* (2013.01); *A61K 9/5123* (2013.01); *A61K 33/04* (2013.01); *A61K 9/5192* (2013.01)

(58) Field of Classification Search
None
See application file for complete search history.

(56) References Cited

U.S. PATENT DOCUMENTS

| 9,259,005 B2 | 2/2016 | Webster et al. |
|---|---|---|
| 2012/0157519 A1* | 6/2012 | Sredni .............. A61P 31/16 549/348 |
| 2013/0236523 A1 | 9/2013 | Webster et al. |
| 2016/0000725 A1 | 1/2016 | Geilich et al. |
| 2017/0181971 A1 | 6/2017 | Geilich et al. |
| 2019/0307895 A1 | 10/2019 | Brown et al. |

OTHER PUBLICATIONS

Kaviya, S., et al., Biosynthesis of silver nanoparticles using citrus sinensis peel extract and its antibacterial activity, Spectrochimica Acta Part A 79 (2011) 594-598.*
Estevam, E.C., et al., Aspects of a Distinct Cytotoxicity of Selenium Salts and Organic Selenides in Living Cells with Possible Implications for Drug Design, Molecules 2015, 20, 13894-13912.*
Qiu, W.-Y., et al., Construction, stability, and enhanced antioxidant activity of pectin-decorated selenium nanoparticles, Colloids and Surfaces B: Biointerfaces 170 (2018) 692-700 (Year: 2018).*
Ba, L.A., et al., "Tellurium: an element with great biological potency and potential," Org. Biomol. Chem., 8, 4203-4216 (2010).
Borghese, R., et al., "Extracellular production of tellurium nanoparticles by the photosynthetic bacterium Rhodobacter capsulatus," Journal of Hazardous Materials 309, 202-209 (2016).
Clark, J., et al., "Green Chemistry Principles," Process Intensification for Green Chemistry: Engineering Solutions for Sustainable Chemical Processing, Chapter 2, pp. 33-58 (2013).
Centers for Disease Control and Prevention. 2014 National and State Healthcare-Associated Infections Progress Report. Published Mar. 2016. Available at www.cdc.gov/hai/progress-report/index.html.
Chasteen, T.G., et al., "Tellurite: history, oxidative stress, and molecular mechanisms of resistance," FEMS Microbiol Rev 33, 820-832 (2009).
Cruz, D. M., et al., "Synthesis and characterization of biogenic selenium nanoparticles with antimicrobial properties made by Staphylococcus aureus, methicillin-resistant *Staphylococcus aureus* (MRSA), *Escherichia coli*, and Pseudomonas aeruginosa," J Biomed Mater Res Part A:106A:1400-1412 (2018).
Davey et al., "Interventions to improve antibiotic prescribing practices for hospital inpatients review)," Cochrane Database of Systematic Reviews, Issue 2, Art. No. CD003543, 2017.
Dayem, A.A., et al., "The Role of Reactive Oxygen Species (ROS) in the Biological Activities of Metallic Nanoparticles," Int. J. Mol. Sci. 18, 120, pp. 1-21 (2017).
Fathima, B. S., et al., "Biosynthesis and optimization of silver nanoparticles by endophyticfungus Fusarium solani," Materials Letters132, 428-431 (2014).
Forootanfar, H., et al., "Microbial-assisted synthesis and evaluation the cytotoxic effect of tellurium nanorods," Materials Science and Engineering C 49, 183-189 (2015).
Gacem, N., et al., "Effect of solvent polarity on the assembly behavior of PVP coated rhodium nanoparticles," Colloids and Surfaces A: Physicochem. Eng. Aspects 417, 32-38 (2013).
Guo, D., et al., "Anti-leukemia activity of PVP-coated silver nanoparticles via generation of reactive oxygen species and release of silver ions," Biomaterials 34, 7884-7894 (2013).
He, W., et al., "A facile synthesis of Te nanoparticles with binary size distribution by green chemistry," Nanoscale, 3, 1523 (2011).
Ikemoto, H., Goyo, A., and Miyanaga, T. (2011). Size Dependence of the Local Structure and Atomic Correlations in Tellurium Nanoparticles. The Journal of Physical Chemistry C, 115(7), 2931-2937. https://doi.org/10.1021/jp107475x.

(Continued)

*Primary Examiner* — H. Sarah Park
(74) *Attorney, Agent, or Firm* — Hamilton, Brook, Smith & Reynolds, P.C.

(57) ABSTRACT

Methods disclosed herein provide for an environmentally-friendly approach that employ citric extracts from fruits as unique reducing and stabilizing agents for making a tellurium nanomaterial. A particular method of making a tellurium nanomaterial includes combining citrus fruit extract with a tellurium salt to form a mixture of citrus fruit extract and dissolved tellurium salt; and heating the mixture of citrus fruit extract and dissolved tellurium salt, thereby making the tellurium nanomaterial. The resulting nanoparticles exhibit enhanced and desirable biomedical properties toward treatment of both infectious diseases and cancer.

8 Claims, 31 Drawing Sheets

(56) References Cited

OTHER PUBLICATIONS

Jianfeng, Y., et al., "Preparation of PVP coated Cu NPs and the application for low-temperature bonding," J. Mater. Chem., 21, 15981 (2011).
Lara, H. H., et al., "Bactericidal effect of silver nanoparticles against multidrug-resistant bacteria," World J Microbiol Biotechnol (2010) 26:615-621 (2010).
Li, M., et al., "Toxicity of ZnO Nanoparticles to *Escherichia coli*: Mechanism and the Influence of Medium Components," American Chemical Society, Environ. Sci. Technol., 45, 1977-1983 (2011).
Li, X., et al., "Functional Gold Nanoparticles as Potent Antimicrobial Agents against Multi-Drug-Resistant Bacteria," vol. 8, No. 10, pp. 10682-10686 (2014).
Liu, Z., et al., "Size-Controlled Synthesis and Growth Mechanism of Monodisperse Tellurium Nanorods by a Surfactant-Assisted Method," Langmuir 20, 214-218 (2004).
Liu, L., et al., "The potent antimicrobial properties of cell penetrating peptide-conjugated silver nanoparticles with excellent selectivity for Gram-positive bacteria over erythrocytes," Nanoscale, 5, 3834 (2013).
Lushniak, B. D. "Antibiotic Resistance: A Public Health Crisis." Public Health Reports, vol. 129, No. 4, 2014, pp. 314-316., doi:10. 1177/0.
Mousavi-Kamazani, M., et al., "Sonochemical synthesis, formation mechanism, and solar cell application of tellurium nanoparticles," Ultrasonics—Sonochemistry 39, 233-239 (2017).
Ogra, Y., "Biology and toxicology of tellurium explored by speciation analysis," Metallomics, 9, 435 (2017).
Parveen, K., et al., "Green synthesis of nanoparticles: Their advantages and disadvantages," AIP Conference Proceedings 1724, 020048; https://doi.org/10.1063/1.4945168 (2016).
Polsongkram, D., et al., "Effect of synthesis conditions on the growth of ZnO nanorods via hydrothermal method," Physica B 403, 3713-3717 (2008).
Pugin, B., et al., "Glutathione Reductase-Mediated Synthesis of Tellurium-Containing Nanostructures Exhibiting Antibacterial Properties," vol. 80, No. 22, Applied and Environmental Microbiology p. 7061-7070 (2014).
Rai et al., "Silver nanoparticles: the powerful nanoweapon against multidrug-resistant bacteria," Journal of Applied Microbiology 112, The Society for Applied Microbiology, pp. 841-852, 2012.
Ramos-Ruiz, A., "Recovery of Elemental Tellurium Nanoparticles by the Reduction of Tellurium Oxyanions in a Methanogenic Microbial Consortium," Environ Sci Technol. 50(3): 1492-1500 (2016).
Seng, H.L., "Anti-cancer potential of selenium- and tellurium-containing species: opportunities abound!," Appl. Organometal. Chem. 26, 655-662 (2012).
Sredni, B., "Immunomodulating tellurium compounds as anti-cancer agents," Seminars in Cancer Biology 22 (2012) 60-69 (2012).
Suresh, A.K., "Co-Relating Metallic Nanoparticle Characteristics and Bacterial Toxicity," Springer Briefs in Molecular Science Biometals, pp. 1-47 (2015).
Taylor, D.E., "Bacterial tellurite resistance," Trends in Microbiology, 111 vol. 7 No. 3 (1999).
Ventola, C. Lee, "The antibiotic resistance crisis. Part 1: causes and threats," P&T, vol. 40, No. 4, pp. 277-283, Apr. 2015.
Virkutyte, J., et al., "Green synthesis of metal nanoparticles: Biodegradable polymers and enzymes in stabilization and surface functionalization," Chem. Sci., 2, 837 (2011).
Virkutyte, J., et al., "Environmentally Friendly Preparation of Metal Nanoparticles," RSC Green Chemistry No. 19, Chapter 2, pp. 7-33, The Royal Society of Chemistry (2013).
Walter, E.G., et al., "Plasmid-Mediated Resistance to Tellurite: Expressed and Cryptic," Plasmid 27, 52-64 (1992).
Wang, J., et al., "Te hexagonal nanotubes: formation and optical properties," J Mater Sci 51:7170-7178 (2016).
Yu, Q., et al., "Inhibition of gold nanoparticles (AuNPs) on pathogenic biofilm formation and invasion to host cells," www.nature. com/scientificreports, pp. 1-14 (2016).
Yuan, L., "Nanostructured tellurium semiconductor: from nanoparticles to nanorods," Journal of Experimental Nanoscience, 8:7-8, 931-936 (2013).
Zannoni, D., et al., "The Bacterial Response to the Chalcogen Metalloids Se and Te," Advances in Microbial Physiology, vol. 53 (2008).
Zare, B., et al., "Biosynthesis and recovery of rod-shaped tellurium nanoparticles and their bactericidal activities," Materials Research Bulletin 47, 3719-3725 (2012).
Zare, B., et al., "Tracing Tellurium and Its Nanostructures in Biology," Biol Trace Elem Res 180:171-181 (2017).
Zhang, Y., et al., "Hyperbranched Poly(amidoamine) as the Stabilizer and Reductant to Prepare Colloid Silver Nanoparticles in Situ and Their Antibacterial Activity," J. Phys. Chem. C, 112, 2330-2336 (2008).
Zheng, R., et al., "Synthesis of tellurium nanorods via spontaneous oxidation of NaHTe at room temperature," Chemical Physics Letters 395, 302-305 (2004).
Zonaro, E., et al., "Biogenic selenium and tellurium nanoparticles synthesized by environmental microbial isolates efficaciously inhibit bacterial planktonic cultures and biofilms," Frontiers in Microbiology, www.frontiersin.org, vol. 6, Article 584 (2015).
Cunha, R. L.O.R., et al., "A glimpse on biological activities of tellurium compounds," Anais da Academia Brasileira de Ciências 81(3): 393-407 (2009).
Qian et al., "High-Quality Luminescent Tellurium Nanowires of Several Nanometers in Diameter and High Aspect Ratio Synthesized by a Poly (Vinyl Pyrrolidone)—Assisted Hydrothermal Process," Langmuir, 22, 2006, pp. 3830-3835.
Zhong et al., "Controlled solvothermal synthesis of single-crystal tellurium nanowires, nanotubes, and trifold structures and their photoelectrical properties," Cryst. Eng. Comm., 2017, 19, pp. 2813-2820.
Zhu et al., "Poly(vinylpyrrolidone): a new reductant for preparation of tellurium nanoro, nanowires, and tubes from $TeO_2$," Nanotechnology, 17, 2006, pp. 645-650.
Liu et al., "Mesostructured Assemblies of Ultrathin Superlong Tellurium Nanowires and Their Photoconductivity," J. Am. Chem. Soc., 132: 8945-8952 (2010).
Weast, Robert C. and Astle, Melvin J. (Eds.), CRC Handbook of Chemistry and Physics, 61st ed, CRC Press, Inc. (1980) (pp. D-155 through D-157).

* cited by examiner

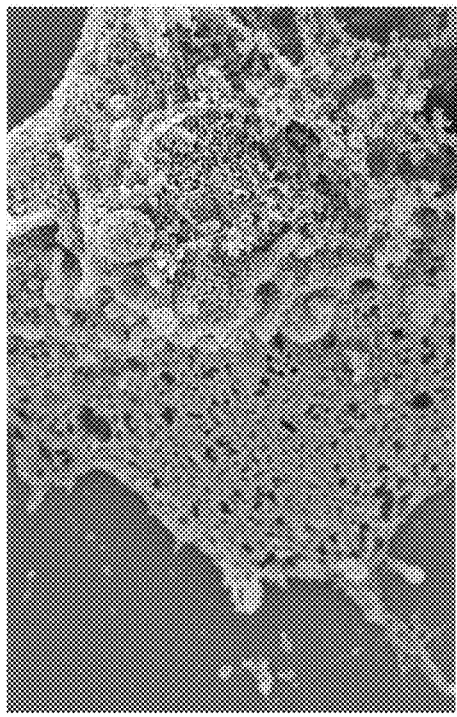
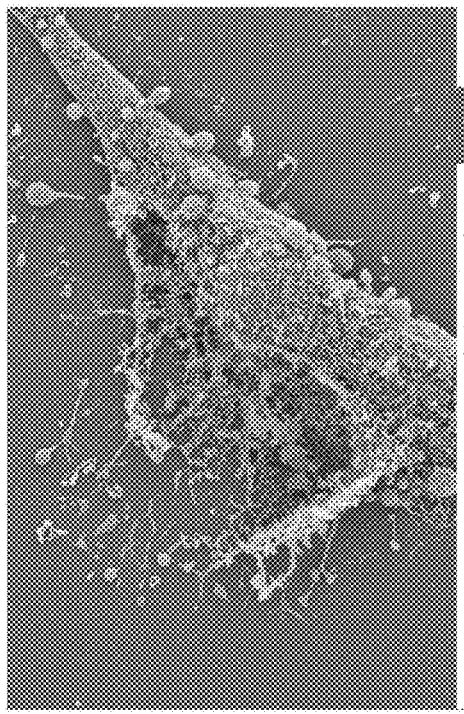
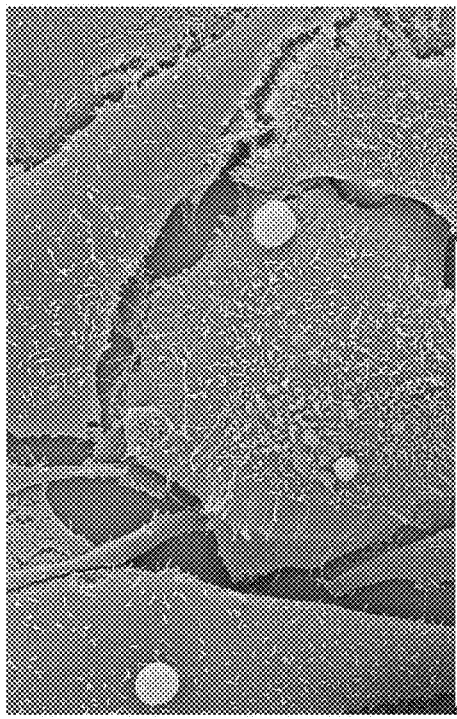
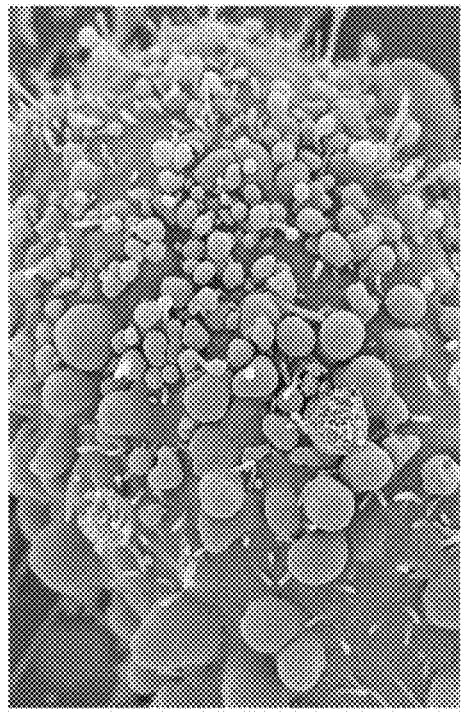
FIG. 12A
FIG. 12B
FIG. 12C
FIG. 12D

LEM-Te NPs

High resolution SEM image of a zone close to Area 2

LIM-Te NPs

High resolution SEM image of a zone close to Area 2

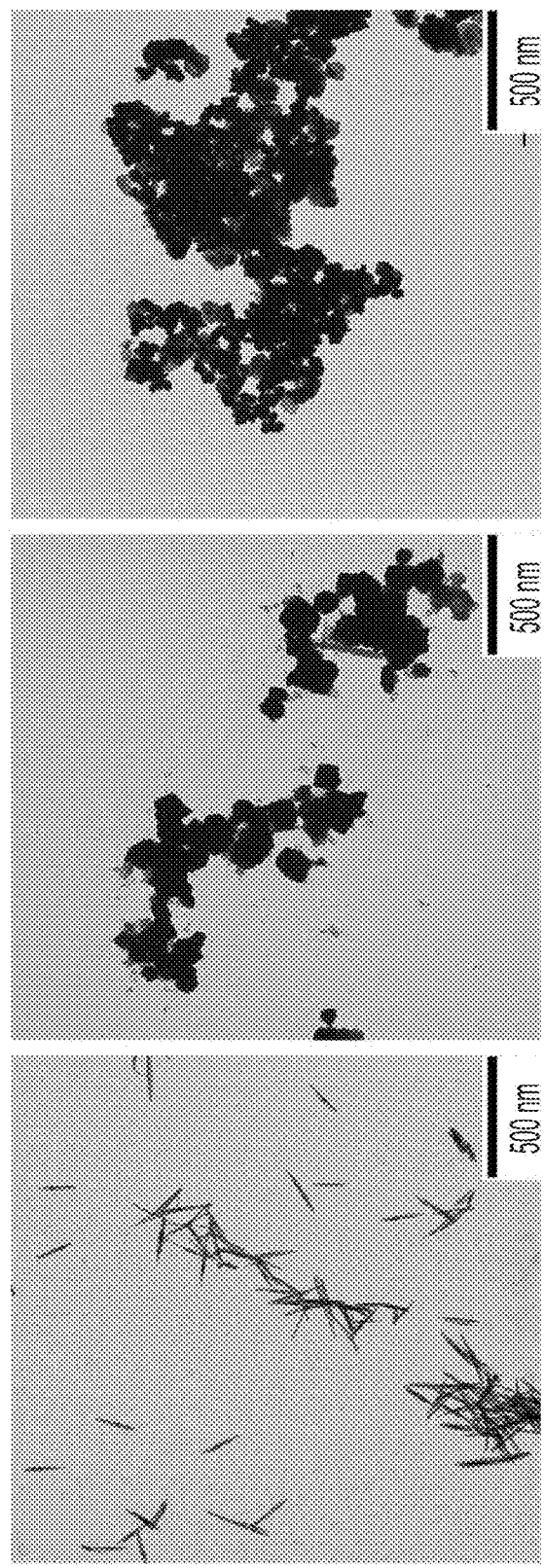

CITRUS FRUIT EXTRACT-MEDIATED SYNTHESIS OF TELLURIUM NANOMATERIALS HAVING BIOMEDICAL APPLICATIONS

RELATED APPLICATION

This application claims the benefit of U.S. Provisional Application No. 62/819,445, filed on Mar. 15, 2019. The entire teachings of the above application are incorporated herein by reference.

BACKGROUND

The widespread use of antibiotics has led to the development of antibiotic-resistant bacteria, threatening our global healthcare system. Because of our over dependence and over prescription of antibiotics, humankind now lives in the post-antibiotic era, where diseases that were easily treated can now kill again.[1,2] According to the Centers for Disease Control (CDC), antimicrobial-resistance to antibiotic (AMR) infections affect 2 million people in the United States annually, and it is predicted that more people will die from AMR pathologies than all diseases combined, including cancer, by 2050, culminating into one person dying from an infection every three seconds.[3]

Cancer can be understood as the abnormal growth of cells and tissue within biological systems. Some cancers are developing resistance to commonly used chemotherapeutics. Using mechanisms such as drug target alteration, drug efflux, DNA damage repair and cell death inhibition, these resistant cells are not killed by conventional cancer therapies.[4] Data from the National Cancer Institute (NCI) shows that in 2018, an estimated 1.7 million new cases of cancer will be diagnosed in the United States and around 600,000 people will die from the disease.[5]

A growing and innovative approach for the treatment of antibiotic resistant bacteria and/or cancer uses nanotechnology. There is an ongoing need to find alternative methods to synthesize nanoparticles in ways that are more environmentally-friendly.

SUMMARY

In the methods described herein, citrus juice (e.g., orange, lemon, and lime extracts) were used as both reducing and capping agents for the green synthesis of tellurium nanoparticles (TeNPs). In some embodiments, the methods use microwave-assisted heating. The TeNPs showed a uniform size distribution, and rod- and cubic-shapes, and were extensively characterized in terms of morphology, structure and composition using TEM, SEM, XPS, XRD, FTIR and EDX analysis. TeNPs showed an important antibacterial activity against both Gram-negative and -positive bacteria in a range of concentrations from 5 to 50 μg mL$^{-1}$ over a 24-hour time period. The resultant nanoparticles showed an anticancer effect toward human melanoma cells over 48 hours at concentrations up to 50 μg mL$^{-1}$. The Te nanostructures showed no significant cytotoxic effect towards human dermal fibroblast at concentrations up to 50 μg mL$^{-1}$.

In summary, described herein are environmentally-friendly and cost-effective methods for synthesizing TeNPs using fruit juices. The resulting nanoparticles exhibit enhanced and desirable biomedical properties, namely, inhibiting growth of bacteria and decreasing viability of cancer cells.

Described herein is a method of making a tellurium nanomaterial. The method includes combining citrus fruit extract with a tellurium salt to form a mixture of citrus fruit extract and dissolved tellurium salt; and heating the mixture of citrus fruit extract and dissolved tellurium salt, thereby making the tellurium nanomaterial.

In some embodiments, the citrus fruit extract is from an orange, a lemon, or a lime. In some embodiments, tellurium salt is sodium tellurite ($Na_2TeO_3$), sodium tellurate ($Na_2TeO_4$), potassium tellurate ($K_2TeO_4$), potassium tellurate hydrate ($K_2TeO_4.H_2O$), potassium tellurite ($K_2TeO_3$), telluric acid ($Te(OH)_6$), or tellurium tetrachloride ($TeCl_4$). In some embodiments, the tellurium salt is $Na_2TeO_3$.

In some embodiments, the method includes dissolving the tellurium salt in a solvent, such as water, prior and adding the solvent to the citrus fruit extract.

In some embodiments, the method includes centrifuging the tellurium nanomaterial.

In some embodiments, heating the mixture of citrus fruit extract and dissolved tellurium salt is performed by microwave heating. In some embodiments, heating the mixture of citrus fruit extract and dissolve tellurium salt includes heating to a temperature from about 25° C. to about 100° C.

Described herein is a method of treating a bacterial infection or cancer in a patient in need thereof. The method includes administering an effective amount of a pharmaceutical composition that includes a tellurium nanoparticle made according to the methods described herein.

Described herein is a composition comprising tellurium nanoparticles. The tellurium nanoparticles are coated with one or more sugars, flavonoids, and water-soluble pectin molecules.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 10A: OR-TeNPs. FIG. 10B: LEM-TeNPs. FIG. 10C: LIM-TeNPs

FIGS. 12A-D are SEM images showing the interaction between melanoma cells and OR- (FIG. 12B), LEM- (FIG. 12C) and LIM-TeNPs (FIG. 12D). Interaction with 0 μg mL$^{-1}$ (FIG. 12A) and 50 μg mL$^{-1}$ (FIGS. 12B, 12C, and 12D) of the respective Te nanoparticles and melanoma cells were analyzed.

FIG. 17A is scanning electron microscope image of a sample containing OR-TeNPs, showing the selection of two areas of interest that will be characterized. FIG. 17B is high resolution scanning electron microscope image of Area 1 in the sample containing OR-TeNPs. FIG. 17C is an energy-dispersive X-ray spectroscopy (EDX) analysis of both area 1 and 2 of a sample containing OR-TeNPs showing the elemental distribution of different elements of interest (carbon, oxygen, sodium, potassium and tellurium). FIG. 17D is a bar graph showing the atomic composition of area 1 of a sample containing OR-TeNPs converted to percentage. FIG. 17E is a bar graph showing the atomic composition of area 2 of a sample containing OR-TeNPs converted to percentage.

FIG. 18A is scanning electron microscope image of a sample containing LEM-TeNPs, showing the selection of two areas of interest that will be characterized. FIG. 18B is high resolution scanning electron microscope image of Spot 1 in the sample containing LEM-TeNPs. FIG. 18C is an energy-dispersive X-ray spectroscopy (EDX) analysis of both Spot 1 and Area 2 of a sample containing LEM-TeNPs showing the elemental distribution of different elements of interest (carbon, oxygen, sodium, potassium and tellurium). FIG. 18D is a bar graph showing the atomic composition of Spot 1 of a sample containing LEM-TeNPs converted to percentage. FIG. 18E is a bar graph showing the atomic composition of area 2 of a sample containing LEM-TeNPs converted to percentage.

FIG. 19A is scanning electron microscope image of a sample containing LIM-TeNPs, showing the selection of two areas of interest that will be characterized. FIG. 19B is high resolution scanning electron microscope image of Spot 1 in the sample containing LIM-TeNPs. FIG. 19C is an energy-dispersive X-ray spectroscopy (EDX) analysis of both Spot 1 and Area 2 of a sample containing LIM-TeNPs showing the elemental distribution of different elements of interest (carbon, oxygen, sodium, potassium and tellurium). FIG. 19D is a bar graph showing the atomic composition of Spot 1 of a sample containing LIM-TeNPs converted to percentage. FIG. 19E is a bar graph showing the atomic composition of area 2 of a sample containing LIM-TeNPs converted to percentage.

FIGS. 21A-C are TEM images of OR- (FIG. 21A), LEM- (FIG. 21B) and LIM- (FIG. 21C) TeNPs after 60 days of synthesis. The samples were synthesized using a Te precursor concentration of 50 mM.

DETAILED DESCRIPTION

Figure 1C:
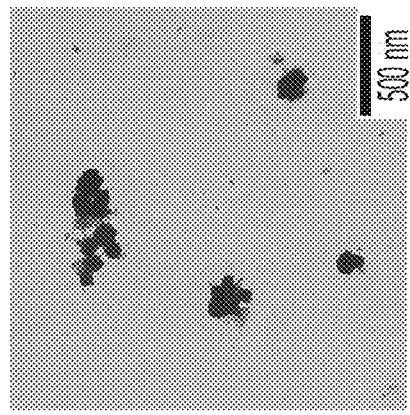
FIGS. 1A-C are transmission electron microscopy (TEM) characterization of TeNPs synthesized by orange (FIG. 1A), lemon (FIG. 1B) and lime (FIG. 1C) juices with 50 mM of metallic salt concentration. Different morphologies and features were found when the nanomaterials were characterized by TEM.

A description of example embodiments follows.

INTRODUCTION

The widespread use of antibiotics has led to the development of antibiotic-resistant bacteria, threatening our global healthcare system. Because of our over dependence and over prescription of antibiotics, humankind now lives in the post-antibiotic era, where diseases that were easily treated can now kill again.[1,2] According to the Centers for Disease Control (CDC), antimicrobial-resistance to antibiotic (AMR) infections affect 2 million people in the United States annually, and it is predicted that more people will die from AMR pathologies than all diseases combined, including cancer, by 2050, culminating into one person dying from an infection every three seconds.[3]

Cancer can be understood as the abnormal growth of cells and tissue within biological systems. Some cancers are developing resistance to commonly used chemotherapeutics. Using mechanisms such as drug target alteration, drug efflux, DNA damage repair and cell death inhibition, these resistant cells are not killed by conventional cancer therapies.[4] Data from the National Cancer Institute (NCI) shows that in 2018, an estimated 1.7 million new cases of cancer will be diagnosed in the United States and around 600,000 people will die from the disease.[5]

Nanotechnology emerged in the 1980s, and soon enough, it was applied to medicine, causing the birth of nanomedicine.[6] Since then, nanomedicine has been reported to decrease bacterial survival and cancerous cell activity and can simultaneously be compatible or even promote mammalian cell functions due to a combination of properties, especially depending on the interfacial layer of the nanoparticles.[7,8] Nanoparticles fundamentally exhibit higher reactivity compared to their respective bulk materials due to high surface area to volume ratios.[9] Moreover, due to their size, nanoparticles can penetrate bacterial and cancer cell membranes in a relatively simple way.[10] A wide variety of metallic nanoparticles that exhibit this behavior are composed of elements widely studied, including silver,[11] gold,[12] titanium and zinc oxides,[13,14] silica,[15] and carbon.[16]

On the other hand, chalcogens, such as selenium (Se) and tellurium (Te), are gaining special interest in nanomedicine for biomedical applications.[17-19] Previous research on the antibacterial properties of tellurium started as early as 1932, and the antimicrobial activity of the metalloid was even reported before the wide-spread use of antibiotics.[20] Primarily, tunable tellurium nanoparticles (TeNPs) and nanotubes have been recently researched and produced for solar energy cells.[21,22] In the biomedical field, tellurite ions ($TeO_3^{2-}$) have been previously researched and have long been known to be toxic and kill most Gram-negative bacteria at concentrations lower than other poisonous metals/metalloids.[23,24]

Tellurium-based nanomaterials can be synthesized using different physical and chemical procedures.[25] However, traditional chemical and physical synthesis methods can have significant drawbacks, including the use of high temperature and pressure, acidic pH of the medium, the use of harsh and expensive chemicals, and the formation toxic-by-products.[26] For instance, some reducing agents used for the synthesis of nanomaterials, such as hydrazine or ammonia, represent a real concern not only for the laboratory in which they are used, but also for the environment.[27] Most of them are not accessible to research facilities in developing countries, where antibacterial solutions are vitally needed to fight against the spread of bacteria that are resistant to antibiotics.[28,29]

Therefore, new methods for nanoparticle synthesis are increasingly in demand to meet the need for clean, cost-effective, environmentally-friendly, and efficient synthesis processes.[30] Compared to traditional synthesis approaches, green methods of synthesizing nanoparticles are clean, inexpensive, and utilize eco-friendly and non-toxic materials and methods.[31] The biological routes for nanoparticle synthesis can be relatively easy and performed in ambient conditions.[32] Living organisms (such as bacteria,[33] fungi[34] and human cells[35]) have shown the ability to reduce metallic ions to elemental nanoparticles. In addition, dietary compounds and natural components have been used, such as honey[36] or tea extracts.[37]

In the methods described herein, the biomolecules presented in the raw materials (such as proteins, cytokines, growth factors, ligands, etc.) may coat nanoparticles acting as natural stabilizers to prevent the formation of clusters of nanoparticles.[38] Aggregation is an extremely detrimental property when discussing nanoparticles and their bioavailability within living organisms and can be a major drawback for the use of nanoparticles in medicine. When aggregated, nanomaterials lose their ability to, for instance, act as antibacterial or anticancer agents since they may not enter cells, clog membrane pores, or may even be cleared by the immune system if too large. More dispersed nanoparticles have a higher cytotoxic effect. The availability of the particles to be internalized by the cells seems to be strongly dependent on the size and morphology of the structures.[39,40]

In this study, different citric juices were used as unique reducing and stabilizing agents for the formation of nanoparticles. On a molecular level, citric juices are composed of organic acids, sugars and phenolic compounds that are able to reduce metallic ions to their elemental form. While the main organic acids are citric, malic and ascorbic, the most prevalent sugars are sucrose, glucose and fructose. There are between 10 and 15 phenolic compounds in these juices, including flavanones and hydroxycinnamic acids, which can serve as reducing agents.[41-43]

Described herein are methods of making TeNPs using a green and environmentally-friendly approach that employs citric extracts from the fruits as unique reducing and stabilizing agents. TeNPs with a uniform size distribution were synthesized using lemon (LEM-TeNPs), lime (LIM-TeNPs), and orange extract (OR-TeNPs). Once purified, the TeNPs were characterized in terms of composition and morphology and tested as antimicrobial agents against both antibiotic-resistant Gram-positive and Gram-negative bacteria, showing different degrees of bacterial inhibition. Cytocompatibility tests were conducted to determine and quantify the effects of the nanoparticles on both healthy and cancerous human cells, showing no significant cytotoxicity for healthy cells yet promising anticancer activity at an acceptable concentration range.

Methods of Making Tellurium Nanoparticles

A salt containing tellurium is dissolved in extract from a citrus fruit. In some embodiments, the salt containing tellurium is dissolved in a solvent, typically water, and then the solvent is added to the citrus juice. The mixture of citrus juice and dissolved tellurium salt is heated. Over a period of time, the tellurium nanomaterials form. The tellurium nanomaterials can be separated from the reaction mixture.

Suitable salts containing tellurium include salts having a tellurite anion ($TeO_3^{2-}$) or tellurate anion ($TeO_4^{2-}$). Examples of suitable salts include sodium tellurite ($Na_2TeO_3$), sodium tellurate ($Na_2TeO_4$), potassium tellurate ($K_2TeO_4$), potassium tellurate hydrate ($K_2TeO_4.H_2O$) (sometimes available as $K_2TeO_4.xH_2O$), potassium tellurite ($K_2TeO_3$), telluric acid ($Te(OH)_6$), and tellurium tetrachloride ($TeCl_4$).

In some embodiments, the tellurium salt is added to the reaction mixture so that it has a concentration from about 1 mM to about 10 mM. The combined concentration of the reducing/capping agents: constant, ranging from 1 to 10 mM.

In general, a capping agent coats the nanostructures during the synthesis. Capping agents within citrus juice include proteins, amino acids, ascorbic acid, and vitamins (e.g., vitamin A, vitamin B1, vitamin B2, vitamin B3, vitamin B6, vitamin C, and others).

In general, a reducing agent is a molecule containing reducing groups, such as hydroxyl groups (—OH), which can react with the ions of the metalloid salt (in this case, tellurium) to generate nuclei of nanoparticles that will lead to bigger structures. An example of a reducing agent within citrus juices is carbohydrates.

Several methods for heating the reaction mixture are suitable. In some embodiments, and in the examples described herein, microwave energy is used to heat the reaction mixture. With microwave-assisted heating, the tellurium nanomaterials can form beginning within seconds. In some embodiments, no longer than one minute of continuous microwave heating is necessary to form the tellurium nanomaterials. Typically, the reaction mixture is heated to a temperature from about 40° C. to about 100° C. Typically, the reaction mixture is heated for a duration from about 5 seconds to about 25 seconds.

In some embodiments, a hydrothermal process is used to heat the reaction mixture. For example, a closed reactor vessel can be used. The closed reactor vessel can be heated, typically to a temperature from about 100° C. to about 200° C., though other temperatures are suitable. The pressure in the closed reaction vessel can be elevated, relative to ambient pressure, such as to a pressure from about 1 MPa to about 3 MPa. Reaction times between 10 and 20 hours.

In some embodiments, a water bath reaction can be used. In these embodiments, the reaction vessel can be placed in a water bath, which can be heated to a temperature from about 40° C. to about 95° C. Typically, the reaction is heated for a duration from about 5 minutes to about 60 minutes.

In some embodiments, the reaction mixture can be stirred and heated using a hot plate having a stirring function and a small magnet (e.g., magnetic stirring bar) placed within the reaction vessel. Typically, the reaction mixture is heated to a temperatures from about 40° C. to about 95° C. Typically, the reaction is heat heated for a duration from about 5 minutes to about 60 minutes.

Typically, the reaction mixture has a pH from about 6 to about 8. Preferable, the reaction mixture has a pH from about 6.5 to about 7.5. Even more preferably, the reaction mixture has a pH close to 7.2.

Extract from Citrus Fruits

Citrus is a genus of flowering trees and shrubs in the Rutaceae family. "Citrus juice" refers to juice extracted from the fruit of tree within the genus Citrus. A wide variety of citrus juices are suitable for the methods described herein. Some examples are listed in Table 1, though there are many others, including many hybrids.

TABLE 1

Examples of suitable citrus plants

| Common Name | Genus and Species |
| --- | --- |
| Amanatsu | Citrus natsudaidai |
| Balady citron | Citrus medica |
| Israel citron | |
| Bergamot orange | Citrus bergamia |
| Bitter orange | Citrus x aurantium |
| Seville orange | |
| Sour orange | |
| Bigarade orange | |
| Marmalade orange | |
| Blood orange | Citrus x sinensis |
| Buddha's hand | Citrus medica var. sarcodactylis |
| Bushukan | |
| Fingered citron | |
| Calamondin | x Citrofortunella mitis |
| Calamansi | |
| Cam sành | Citrus reticulata x maxima |
| Citron | Citrus medica |
| Clementine | Citrus reticulata |
| Corsican citron | Citrus medica |
| Desert lime | Citrus glauca |
| Etrog | Citrus medica |
| Finger lime | Citrus australasica |
| Florentine citron | Citrus medica |
| Grapefruit | Citrus x paradisi |
| Greek citron | Citrus medica |
| Hyuganatsu | Citrus tamurana |
| Konatsu | |
| Tosakonatsu | |
| New Summer Orange | |
| First Lady | Citrus x iyo |
| Anadomikan | |
| Kabosu | Citrus sphaerocarpa |
| Kaffir lime | Citrus hystrix |
| Key lime | Citrus aurantiifolia |
| Kinnow | Citrus nobilis x Citrus deliciosa |
| Kiyomi | Citrus unshiu x Citrus sinensis |
| Kumquat | Citrus japonica |
| Lemon | Citrus limon |
| Lime | |
| Mandarin orange | Citrus reticulata |
| Mandarin | |
| Mandarine | |
| Mangshanyegan | Citrus mangshanensis |
| Meyer lemon | Citrus x meyeri |
| Moroccan citron | Citrus medica |
| Myrtle-leaved orange tree | Citrus myrtifolia |
| Orange | Citrus x sinensis |
| Sweet orange | |
| Oroblanco | Citrus grandis x C. Paradisi/Citrus maxima/Citrus grandis |
| Sweetie | |
| Papeda | |
| Persian lime | Citrus x latifolia |
| Tahiti lime | |
| Bearss lime | |
| Pomelo | Citrus maxima or Citrus grandis |
| Pummelo | |
| Pommelo | |
| Shaddock | |
| Ponderosa lemon | Citrus maxima x medica |
| Rangpur | Citrus x limonia |
| Lemandarin | |
| Round lime | Citrus australis |
| Australian lime | |
| Australian round lime | |

TABLE 1-continued

Examples of suitable citrus plants

| Common Name | Genus and Species |
| --- | --- |
| Satsuma | Citrus unshiu |
| Cold hardy mandarin | |
| Satsuma mandarin | |
| Satsuma orange | |
| Christmas orange | |
| Tangerine | |
| Shangjuan | Citrus cavaleriei × C. maxima |
| Ichang lemon | |
| Shonan Gold | Citrus flaviculpus hort. ex Tanaka (Ōgonkan) × Citrus unshiu |
| Sudachi | Citrus sudachi |
| Sweet limetta | Citrus limetta |
| Mediterranean sweet lemon | |
| Sweet lemon | |
| Sweet lime | |
| Taiwan tangerine | Citrus × depressa |
| Flat lemon | |
| Hirami lemon | |
| Thin-skinned flat lemon | |
| Tangelo | C. reticulata × C. maxima or × C. paradisi |
| Honeybell | |
| Tangerine | Citrus tangerina |
| Tangor | C. reticulata × C. sinensis |
| Ugli fruit | Citrus reticulata × Citrus paradisi |
| Yuzu | Citrus cavaleriei × C. reticulata |

Extracts from the citrus fruit can be made by squeezing the citrus fruit and collecting the liquid extract. Purification of the extract is not required.

Tellurium Nanoparticles

A nanoparticle is a particle of less than about 1 micron in its largest dimension. A rod shape is a three-dimensional solid shape that is longer than it is wide, and can, for example, be a cylindrical or substantially cylindrical shape. A nanorod is a nanoparticle that is rod shaped.

Tellurium nanoparticles produced in accordance with methods described herein can be rod shape. In some embodiments, the tellurium nanoparticles are rod-shaped and can have a length from about 50 nm to about 200 nm, and a width from about 2 nm to about 15 nm. In some embodiments, the tellurium nanoparticles are closer to a cubic shape, with lengths from about 100 nm to about 200 nm.

Pharmaceutical Compositions and Uses of Tellurium Nanoparticles

Tellurium nanoparticles can be administered to a patient or subject as an antibacterial agent or an anticancer agent. Pharmaceutical compositions are described herein.

Tellurium nanoparticles can be coatings applied to surfaces (e.g., of medical devices) as an antibacterial agent. Nanoparticle can be coated on surfaces using a variety of known techniques, including chemical vapor deposition (CVD), electrospinning, electrophoretic deposition, and spray coating.

Tellurium nanoparticles can be used as a coating agent for medical platforms/deliverables (e.g., bandages for administration to the skin). Nanoparticle can be coated on surfaces using a variety of known techniques, including electrospinning, electrophoretic deposition, and spray coating.

Tellurium nanoparticles can be used as additives in hand soaps and other cleaning or disinfecting products.

An antibacterial property is the property of inhibiting or killing bacteria, and an antibacterial agent is a substance that inhibits or kills bacteria. An anticancer property is the property of destroying or inhibiting cancer cells, and an anticancer agent is a substance that destroys or inhibits cancer cells.

Nanoparticles in accordance with an embodiment of the invention can be used in coatings for medical equipment that is susceptible to bacterial growth. The anti-cancer properties of the nanoparticles allow them to be used in applications in cancer therapeutics. A feature of the nanoparticles is the use of tellurium, an antibacterial, yet under-researched metalloid material. The effects of the nanoparticles on cells, such as human dermal fibroblasts (HDF) and melanoma, allow for a wide range of uses outside of antimicrobial coatings. The nanoparticles can also be used to counter the problem of antibiotic resistance.

Nanoparticles in accordance with an embodiment of the invention can be used in a variety of different possible applications, including, for example: medical device applications, including antibacterial coatings for medical equipment or tubing; anticancer applications, including potential cancer treatments containing these nanoparticles; antibacterial treatment of hospital acquired infections (HAIs), which represent greater than $28 billion in direct cost to US hospitals and result in 90,000 patient deaths each year; antibacterial coatings for pipes; and cancer therapeutic applications.

The nanoparticle can have antibacterial properties against Gram-positive bacteria, Gram-negative bacteria, or both; and can have antibacterial properties against antibiotic resistant bacteria. For example, the nanoparticle can have antibacterial properties against one or more of: *Escherichia coli*, *Staphylococcus aureus*, methicillin-resistant *Staphylococcus aureus*, and multidrug-resistant *Escherichia coli*. For example, in experiments in accordance with embodiments described herein, the following strains of bacteria have been used: *Escherichia coli* (e.g., strain K-12 HB101; Bio-Rad, Hercules, Calif.), *Staphylococcus aureus* (subsp. *aureus* Rosenbach, e.g., ATCC® 12,600™; ATCC, Manassas, Va.), methicillin-resistant *Staphylococcus aureus* (e.g., ATCC 4330; ATCC, Manassas, Va.), and multidrug-resistant *Escherichia coli* (e.g., ATCC BAA-2471; ATCC, Manassas, Va.). The nanoparticle can have anticancer properties, and can, for example, have cytotoxic effects against human melanoma cells. In experiments in accordance with an embodiment described herein, for example, effects against primary human dermal fibroblasts (ATCC® PCS201012™, Manassas, Va.) and melanoma (ATCC® CRL-1619, Manassas, Va.) cells were performed.

A composition according to the invention includes a carrier medium, and the nanoparticles taught herein, with the nanoparticles present in the carrier medium in a concentration of between about 10 µg/mL and about 100 µg/mL, for example in a concentration of between about 25 µg/mL and about 100 µg/mL in the carrier medium. A concentration of between about 10 µg/mL and about 100 µg/mL can, for example, be used for anticancer effects, and the concentration of between about 25 µg/mL and about 100 µg/mL can, for example, be used for antibacterial effects. In experiments in accordance with an embodiment of the invention, bacterial analysis has been performed at 25, 50, 75 and 100 µg/mL, for example, while cell analysis has been performed at 10, 15, 50 and 100 µg/mL, for example.

The carrier medium can be a solvent, such as an aqueous solution. The composition can be a pharmaceutical composition, and can include a pharmaceutically acceptable excipient. The pharmaceutical composition can be suitable for one or more of parenteral administration and oral administration.

A device in accordance with an embodiment of the invention includes an antibacterial or anticancer surface, with a coating on at least part of the surface of the device, the coating including the nanoparticles taught herein. The device can, for example, be medical equipment, such as one or more of: a medical implant, a surgical instrument, a medical tubing, and a component of a medical operating theater.

A method of treating cancer in a patient in need thereof, in accordance with an embodiment of the invention, can include administering an effective amount of a pharmaceutical composition comprising the tellurium nanoparticle described herein. The pharmaceutical composition comprises (i) a carrier medium; (ii) a plurality of tellurium nanoparticles, which, in some embodiments, can have a rod shape; and (iii) a pharmaceutically acceptable excipient. The plurality of tellurium nanoparticles can be present in the carrier medium at a concentration from about 10 micrograms per milliliter (µg/mL) to about 100 micrograms per milliliter (µg/mL). The nanoparticles can, for example, have cytotoxic effects against human melanoma cells, or another cancer.

A method of treating a bacterial infection in a patient in need thereof, in accordance with an embodiment of the invention, comprises administering an effective amount of a pharmaceutical composition comprising a nanoparticle taught herein. The pharmaceutical composition comprises: (i) a carrier medium; (ii) a plurality of tellurium nanoparticles, which, in some embodiments, can have a rod shape; and (iii) a pharmaceutically acceptable excipient. The plurality of nanoparticles can be present in the carrier medium at a concentration of from about 25 micrograms per milliliter (µg/mL) to about 100 micrograms per milliliter (µg/mL). The nanoparticles can, for example, have antibacterial properties against at least one of Gram-positive and Gram-negative bacteria. The nanoparticles can, for example, have antibacterial properties against antibiotic resistant bacteria. The nanoparticles can, for example, have antibacterial properties against at least one of: *Escherichia coli, Staphylococcus aureus*, methicillin-resistant *Staphylococcus aureus*, and multidrug-resistant *Escherichia coli*.

The tellurium nanoparticles can also be used in a method of treating a cancer. In some embodiments, the method can include administering to a subject in need thereof the pharmaceutical composition comprising tellurium nanoparticles for a time sufficient to treat the cancer.

The tellurium nanoparticles can also be used in a method of treating a bacterial infection. In some embodiments, the method can include administering to a subject in need thereof the pharmaceutical composition comprising tellurium nanoparticles for a time sufficient to treat the bacterial infection.

An effective amount of a pharmaceutical composition comprising the tellurium nanoparticles refers to the amount needed to perform its intended function, i.e., elicit a desired biological response. The effective amount of tellurium nanoparticles may vary depending on such factors including the type and severity of the disease, the patient's gender, age, weight and health, the route of administration, etc. The nanoparticles disclosed herein may be formulated in dosage unit form. For example, dosages of the nanoparticles may be from about 0.01 mg/kg/day to about 500 mg/kg/day, for example, from about 0.1 mg/kg/day to about 100 mg/kg/day.

A therapeutically effective amount of the nanoparticles can be administered in a single dose or multiple doses. Further, the dosages of the nanoparticles can be proportionally increased or decreased as needed.

The methods may include administration of a nanoparticle composition, wherein the composition is administered over a period of one week, two weeks, three weeks, a month, two months or longer. For example, disclosed herein are methods of treating cancers or bacterial infections that include administering a nanoparticle composition over a period of at least two weeks, three weeks, one month or administered over a period of about 2 weeks to about 6 months or more, at once, twice, or three times a day, once a week, once every two weeks, once every three weeks, or once every month, and wherein the dose of the active agent at each administration is from about 0.01 mg/kg to about 500 mg/kg, for example, from about 0.1 mg/kg to about 100 mg/kg.

An implant is a medical device that replaces, supports or enhances a biological structure, and can, for example include a sensory or neurological implant, a cardiovascular implant, an orthopedic implant, an electric implant, a contraception implant, a cosmetic implant, a gastrointestinal implant, a respiratory implant or a urological implant.

A pharmaceutically acceptable excipient is a substance formulated alongside the active ingredient of a pharmaceutical composition, for long-term stabilization, bulking up, or conferring therapeutic enhancement; and that is shown to be pharmaceutically safe. For example, excipients can include, for example, buffers, acids, bases, salts, solubilizers, preservatives, chelating agents, sugars, amino acids, proteins and solvents. One, several, or all of these can be present in a pharmaceutical composition.

Buffering agents suitable for use an excipient include, but are not limited to, ACES, acetate, ADA, ammonium hydroxide, AMP (2-amino-2-methyl-1-propanol), AMPD (2-amino-2-methyl-1,3-propanediol), AMPSO, BES, BICINE, bis-tris, BIS-TRIS propane, borate, CABS, cacodylate, CAPS, CAPSO, carbonate, CHES, citrate, DIPSO, EPPS, HEPPS, ethanolamine, formate, glycine, glycylglycine, HEPBS, HEPES, HEPPSO, histidine, hydrazine, imidazole, malate, maleate, MES, methylamine, MOBS, MOPS, MOPSO, phosphate, piperazine, piperidine, PIPES, POPSO, propionate, pyridine, pyrophosphate, succinate, TABS, TAPS, TAPSO, taurine (AES), TES, tricine, triethanolamine, Trizma.

Salts suitable for use as an excipient can, for example, include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts. Alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, quinine, quinoline, and basic amino acid such as lysine and arginine are also included.

Preservatives are often added to biopharmaceutical products to lengthen the shelf live. A representative list includes ascorbic acid, benzoic acid, benzyl alcohol, benzylalkonium chloride, erythorbic acid, propionic acid, sorbic acid, thiodipropionic acid, ascorbyl palmitate, butylated hydroxyanisole, butylated hydroxytoluene, calcium ascorbate, calcium propionate, calcium sorbate, dilauryl thiodipropionate, gum guaiac, methylparaben, metabisulfite, m-cresol, paraben, potassium bisulfite, potassium metabisulfite, potassium sorbate, propyl gallate, propylparaben, sodium ascorbate, sodium benzoate, sodium bisulfite, sodium metabisulfite, sodium propionate, sodium sorbate, sodium sulfite, stannous chloride, sulfur dioxide, tocopherols.

In order to dissolve and maintain dissolution of the pharmaceutical ingredient, solubilizers can be added to the biopharmaceutical composition; PEG, Tween, CMC, and SDS are all possibilities for agents used as solubilizers.

Chelating agents include, but are not limited to, citric acid, tartaric acid, calcium acetate, calcium chloride, calcium citrate, calcium diacetate, calcium gluconate, calcium hexametaphosphate, monobasic calcium phosphate, calcium phytate, dipotassium phosphate, disodium phosphate, isopropyl citrate, malic acid, monoisopropyl citrate, potassium citrate, sodium citrate, sodium diacetate, sodium gluconate, sodium hexametaphosphate, sodium metaphosphate, sodium phosphate, sodium pyrophosphate, tetra sodium pyrophosphate, sodium tartrate, sodium potassium tartrate, sodium thiosulfate, sodium tripolyphosphate, stearyl citrate, and tetrasodium ethylenediamine tetraacetate.

Acid and bases are often added to biopharmaceutical products to adjust pH or to enhance efficacy. Representative acids includes nitric acid, hydrochloric acid, sulfuric acid, perchloric acid, hydrobromic acid, hydroiodic acid, acetic acid, ascorbic acid, boric acid, butanoic acid, carbonic acid, citric acid, formic acid heptanoic acid, hexanoic acid, hydrocyanic acid, hydrofluoric acid, lactic acid, nitrous acid, octanoic acid, oxalic acid, pentanoic acid, phosphoric acid, propanoic acid, sulfurous acid, and uric acid. Representative bases include lithium hydroxide, sodium hydroxide, potassium hydroxide, magnesium hydroxide, calcium hydroxide, alanine, ammonia, dimethylamine, ethylamine, glycine, hydrazine, methylamine, and trimethylamine.

Sugars, including glucose (dextrose), fructose, galactose, ribose, sucrose, lactose, maltose, trehalose, cellobiose, arabitol, erythritol, glycerol, isomalt, lactitol, maltitol, mannitol, sorbitol, and xylitol.

Proteins such as albumin, and peptides can also be included as excipients.

An example of amino acid used as an excipient is L-histidine.

An example of protein used as an excipient is bovine serum albumin (BSA).

As used herein, an "organic acid" is an organic compound with acidic properties, and can include, for example, carboxylic acids, sulfonic acids, alcohols, thiols, enols, and phenols; such as, lactic acid, acetic acid, formic acid, citric acid, oxalic acid, uric acid, and ascorbic acid, such as 1-ascorbic acid.

EXEMPLIFICATION

Materials and Methods

Te Nanoparticle Synthesis and Purification

For Te nanoparticle synthesis, a stock concentration of sodium tellurite ($Na_2TeO_3$) (Sigma Aldrich, St Louis, Mo.) was prepared in deionized (DI) water. The different extracts were collected from fresh fruits (specifically, orange, lemon and lime) bought in a local supermarket. The fruits were squeezed, and the liquid was collected. Different metallic salt concentrations (100, 75, 50 and 25 mM) were added to a constant volume of the citric extract in a glass vial. Samples were named depending on the citric extracts used for the synthesis: orange-mediated (OR-TeNPs), lemon-mediated (LEM-TeNP) and lime-mediated (LIM-TeNPs) synthesis. Once mixed, a microwave-assisted reaction was followed. The vials were placed inside the microwave (Whirlpool WMC20005 YB) and a single cycle of heating at 750 W was completed for 10 s, followed by a cool-down of the reaction until reaching room temperature.

The purification process used was the following: the content of each one of the glass vials was transferred to a conical tube and centrifuged at 10 000 rpm for 30 min, generating a black pellet at the bottom of the tube. The solid was washed twice with DI and autoclaved water and the final solid was re-suspended in DI and autoclaved water inside a glass vial that was lyophilized for 24 h. The resulting black powder was weighed, and a specific amount of deionized and autoclaved water was added in order to obtain the desired concentration. The final suspension of Te nanostructures was stored in a fridge in the dark for further experiments.

The samples were centrifuged using both an Eppendorf™ Model 5430 Microcentrifuge and Eppendorf™ Model Centrifuge 5804 R, refrigerated, with Rotor A-4-44 incl. adapters for 15/50 mL conical tubes, a keypad, and at 230 V/50-60 Hz. A FreeZone Plus 2.5 Liter Cascade Console Freeze Dry System was used to lyophilize the samples and obtain the final powder. In addition, an ultrasonic homogenizer (model 150VT) with a power source of up to 150 W was used to homogenize the samples.

Characterization

Morphological characterization of the different nanomaterials was accomplished by transmission electron microscopy (TEM) using a JEM-1010 TEM (JEOL USA Inc., MA). To prepare samples for imaging, nanoparticles were dried on 300-mesh copper-coated carbon grids (Electron Microscopy Sciences, Hatfield, Pa.). A FEI Verios 460 Field Emission Microscope (FE-SEM) (FEI Europe B.V., Eindhoven, Netherlands) using selective secondary/backscattered electrons detection was also used for morphological characterization. For observation, 7 µL of a solution of citric-TeNPs on DI water were deposited on clean Si substrates and were allowed to dry for more than 24 h. The images were taken with 2 kV acceleration voltage and a 25 pA electron beam current. Electron dispersive X-Ray spectroscopy (EDX) was performed using an EDX detector (EDAX Octane Plus, Ametek B.V., Tilburg, Netherlands) coupled to the SEM previously mentioned, for the verification of the presence of elemental tellurium in the structures. SEM conditions for EDX measurements were 10 kV acceleration voltage and 400 pA beam current.

Structural analysis of the nanoparticles systems were carried out by infrared spectroscopy using a Fourier transform infrared spectrometer, Perkin Elmer 400 FT-IR/FT-NIR in attenuated total reflectance (ATR) mode. The samples for FT-IR analysis were prepared by drop casting the TeNPs colloids on a sample holder heated at ~50° C. 5 mg were used to carry out the measurement. The IR spectra were scanned in the range of 500 to 4000 $cm^{-1}$ with a resolution of 4 $cm^{-1}$. The spectra were normalized, and the baseline corrected using Spectrum™ software from Perkin-Elmer.

Powder XRD patterns were obtained with a Rigaku MiniFlex 600 operating at a voltage of 40 kV, a current of 15 mA, and Cu-Kα radiation ($\lambda=1.542$ Å). All XRD patterns were recorded at room temperature with a step width of 0.05 (2θ) and scan speed of 0.2° $min^{-1}$. The preparation of the sample for XRD analysis was done by drying 8 mL of TeNPs colloids on the sample holder.

For X-Ray photoelectron spectroscopy (XPS) experiments, drops of the compounds dispersed in DI water were deposited on clean copper substrates for sample preparation. After water evaporation, the samples were loaded in a vacuum loadlock chamber and then transferred in the XPS Ultra High Vacuum chamber with a base pressure in the low of the $10^{-10}$ mbar range. The XPS chamber was equipped with a hemispherical electron energy analyzer (SPECS Phoibos 100 spectrometer) and a Mg-Kα (1253.6 eV) X-ray source. The angle between the hemispherical analyzer and the plane of the surface was kept at 60°. Wide scan spectra were recorded using an energy step of 0.5 eV and a pass-energy of 40 eV while specific core level spectra (Te 3d, O 1 s and C 1 s) were recorded using an energy step of 0.1 eV and a pass-energy of 20 eV. Data processing was performed with CasaXPS software (Casa software Ltd, Cheshire, UK). The absolute binding energies of the photoelectron spectra were determined by referencing to the Te 3d 5/2 metallic core level at 573 eV. 44, 45 The contributions of the MgKα satellite lines were subtracted and the spectra were normalized to the maximum intensity.

A SpectraMax M3 spectrophotometer (Molecular Devices, Sunnyvale, Calif.) was used to measure the optical density of the bacterial cultures. Growth curves and other bacterial analysis were performed in a plate reader SpectraMax® Paradigm® Multi-Mode Detection Platform.

For cell fixation studies, a Cressington 208HR High Resolution Sputter Coater and a Samdri®-PVT-3D Critical Point dryer was used to prepare the samples, that were imaged using a Hitachi S-4800 SEM instrument at a 3 kV accelerating voltage and 10 μA beam current.

Stability Analysis

In order to analyze the stability of the samples, TEM and zetapotential measurements were completed in fresh and 60-day old TeNPs synthesized using a Te-precursor solution concentration of 50 mM and the three different citric extracts Bacteria Cultures Multidrug-resistant (MDR) *Escherichia coli* (ATCC BAA-2471; ATCC, Manassas, Va.) and methicillin-resistant *Staphylococcus aureus* (MRSA) (ATCC 4330; ATCC, Manassas, Va.) bacteria were selected for the antimicrobial tests to determine the effect of TeNPs synthesized with orange, lemon, and lime extracts. The cultures were maintained on agar plates at 4° C. Bacteria were inoculated into 5 mL of sterile Tryptic Soy Broth (TSB, sigma) in a 50 mL Falcon conical centrifuge tube and incubated at 37° C./200 rpm for 24 h. The optical density was then measured at 600 nm (OD600) using a spectrophotometer. The overnight suspension was diluted to a final bacterial concentration of $10^6$ colony forming units per milliliter (CFU mL$^{-1}$) prior to measuring the optical density.

Antimicrobial Activity of TeNPs

The colony of each bacterial strain was re-suspended in TSB media. The bacterial suspension was placed in a shaking incubator to grow overnight at 200 rpm and remained at a constant 37° C. The overnight suspension was diluted to a bacterial concentration of $10^6$ CFU mL$^{-1}$ and a spectrophotometer was used to perform optical density measurements at 600 nm (OD600). Moreover, the seeding density was determined in each experiment using a colony forming unit assay. Different concentrations of nanoparticles were mixed with 100 μL of bacteria in TSB medium and added to each well of a 96-well plate for the specific antimicrobial assay (Thermo Fisher Scientific, Waltham, Mass.). The control group consisted of bacteria mixed with 100 μL of TSB culture media without the presence of any Te nanoparticles. The final volume per each well was 200 μL.

Once the plate was prepared, the absorbance values of all samples were measured at 600 nm every 2 min on the absorbance plate reader for 24 h. The values coming from the Te nanoparticles system were measured preparing negative controls made of nanoparticles and medium only. For the conversion of OD to CFU mL$^{-1}$, standard curves were used for each one of the bacteria.

The bacterial growth curves were obtained and fitted into the Gompertz model[46] by subtracting the initial values to the entire curve and shifting them to the starting point. For the application of Gompertz distribution, re-parametrization was needed in order to describe the biological parameters (A, μ, and λ) (eqn (2)) rather than the mathematical ones (a, b, c . . . ) (eqn (1)).

$$y = a \cdot e^{-e^{(b-ct)}}$$

Equation 1. Gompertz Equation in Terms of Mathematical Parameters.

The Gompertz equation in terms of mathematical parameters was modified through a series of derivations to obtain the modified equation that was used for the fitting of the curves. The resulting equation describes a sigmoidal growth curve.

$$y = A \cdot e^{-e^{\frac{\mu \cdot e}{A}(\lambda - t) + 1}}$$

Equation 2. Gompertz Equation in Terms of Biological Parameters.

where the parameter y is related to the number of bacteria (corresponding to the optical density reading), A is the maximal possible value of y, μ is the maximal growth rate and λ is the lag time. The parameters A, μ and λ were estimated according to a least-squares estimation algorithm using a GRG nonlinear solver.

The colony counting assays were done by seeding the bacteria in a 96-well plated mixed with different concentrations of TeNPs. The plates were incubated at 37° C. during 8 h and, after that period of time, the plates were removed from the incubator and diluted with PBS in a series of vials ×10$^5$, ×10$^6$ and ×10$^7$. Three drops of 10 μL were taken of each dilution and deposited in a TSB-Agar plate. After a final period of incubation of 8 h inside the incubator at 37° C., the numbers of colonies formed were counted at the end of the incubation.

In Vitro Cytotoxicity Assays with Te Nanoparticles

Cytotoxicity assays were performed with primary human dermal fibroblasts (TCC® PCS-201-012™, Manassas, Va.) and melanoma (ATCC® CRL-1619, Manassas, Va.) cells. Cells were cultured in Dulbecco's Modified Eagle Medium (DMEM; Thermo Fisher Scientific, Waltham, Mass.), supplemented with 10% fetal bovine serum (FBS; ATCC® 302020™, American Type Culture Collection, Manassas, Va.) and 1% penicillin/streptomycin (Thermo Fisher Scientific, Waltham, Mass.). MTS assays (CellTiter 96® AQueous One Solution Cell Proliferation Assay, Promega, Madison, Wis.) were carried out to assess cytotoxicity. Cells were seeded onto tissue-culture-treated 96-well plates (Thermo Fisher Scientific, Waltham, Mass.) at a final concentration of 5000 cells per well in 100 μL of cell medium. After an incubation period of 24 h at 37° C. in a humidified incubator with 5% carbon dioxide ($CO_2$), the culture medium was replaced with 100 μL of fresh cell medium containing concentrations from 5 to 100 µg mL$^{-1}$ of green-synthesized OR-TeNPs, LEM-TeNPs, and LIM-TeNPs. Cells were cultured for another 24 and 48 h at the same conditions and then washed with PBS, the medium was then replaced with 100 µL of the MTS solution (prepared using a mixing ratio of 1:5 of MTS:medium). After the addition of the solution, the 96-well plate was incubated for 4 h in the incubator to allow for a color change. Then, the absorbance was measured at 490 nm on an absorbance plate reader (SpectraMAX M3, Molecular Devices) for cell viability after exposure to the TeNPs concentration. Cell viability was calculated by dividing the average absorbance obtained for each sample by the one achieved by the control sample, and then multiplied by 100. Controls containing cells and media, and just media, were also included in the 96-well plate to identify the normal growth of cells without nanoparticles and to determine the absorbance of the media itself.

Cell Fixation and SEM Imaging

Primary human dermal fibroblasts and melanoma cells were seeded in a 6-well plate with a glass coverslip (Fisher Brand) attached to the bottom. After an incubation period of 24 h at 37° C. in a humidified incubator with 5% carbon dioxide ($CO_2$), media was removed and replaced with fresh one containing a concentration of 50 µg mL$^{-1}$ of OR-, LEM- and LIM-TeNPs. Cells were cultured for another 24 h at same conditions. After, the coverslips were fixed with a primary fixative solution containing 2.5% glutaraldehyde (Electron Microscopy Sciences, EMS) and 0.1 M sodium cacodylate buffer solution (Electron Microscopy Sciences, EMS) for 1 hour. Subsequently, the fixative solution was exchanged for 0.1 M sodium cacodylate buffer and the coverslips were washed 3 times for 10 min. Post-fixation was done using 1% osmium tetroxide (OsO4) solution (Electron Microscopy Sciences, EMS) in buffer for 1 hour. Subsequently, the coverslips were washed three times with buffer and dehydration was progressively achieved with 35, 50, 70, 80, 95 and 100% ethanol (three times for the 100% ethanol). Finally, the coverslips were dried by liquid $CO_2$-ethanol exchange in a Samdri®-PVT-3D Critical Point dryer. The coverslips were mounted on SEM stubs with carbon adhesive tabs (Electron Microscopy Sciences, EMS) after treatment with liquid graphite, and then sputter coated with a thin layer of platinum using a Cressington 208HR High Resolution Sputter Coater. Digital images of the treated and untreated bacterial cells were acquired using a SEM microscope.

Reactive Oxygen Species (ROS) Analysis of Samples

For ROS quantification, 2',7'-dichlorodihydrofluorescein diacetate (H2DCFDA) was used. Human melanoma cells were seed in a 96 well-plate at a concentration of 5×104 cells per mL in presence of different concentrations of the TeNPs as well as in a control without any nanoparticles. The cell were cultured under standard culture conditions (37° C. in a humidified incubator with a 5% carbon dioxide (CO2) atmosphere) for 24 h before the experiment. Briefly, the ROS indicator was reconstituted in anhydrous dimethylsulfoxide (DMSO) to make a concentrated stock solution that was kept and sealed. The growth media were then carefully removed and a fixed volume of the indicator in PBS was added to each one of the wells to a final concentration of 10 µM. The cells were incubated for 30 min at an optimal temperature and the loading buffer was removed afterwards. Fresh media were added and cells were allowed to recover for a short time. The baseline for fluorescence intensity of a sample of the loaded cell period exposure was determined. Positive controls were done stimulating the oxidative activity with hydrogen peroxide to a final concentration of 50 µM. The intensity of fluorescence was then observed by flow cytometry. Measurements were taken by an increase in fluorescence at 530 nm when the sample was excited at 485 nm. Fluorescence was also determined in the negative control—untreated loaded with dye cells maintained in a buffer.

Statistical Analysis

Figure 13:
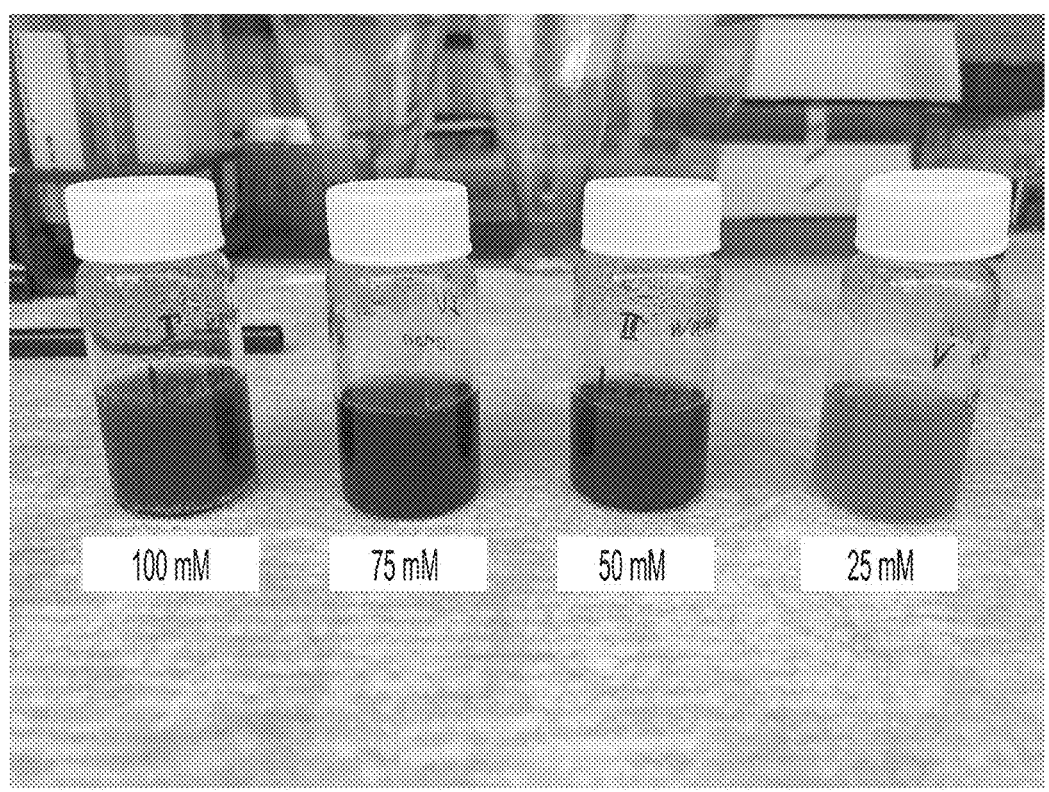
FIG. 13 is a photograph showing coloration of reaction mixture after microwave-assisted synthetic approaches for different Te-precursor solution concentrations. From left to right, a decrease of the metallic salt (sodium tellurite) concentration is translated in a brighten of the black coloration within the solution.

All experiments were repeated in triplicate (N=3) to ensure reliability of results. Statistical significance was assessed using student's t-tests, with a $p<0.05$ being statistically significant. Results are displayed as mean±standard deviation Results and Discussion Synthesis and Purification of TeNPs A facile and quick synthesis of TeNPs using orange, lemon and lime extracts was successfully completed, showing the ability of the extracts as both reducing and stabilizing agents for the generation of elemental tellurium-based nanomaterials. The reduction of Te from ionic state ($Te^{4+}$) to elemental form ($Te^0$) was achieved with the appearance of a dark color within the solution. A change of color from light to dark yellow was observed for all the Te-precursor solution concentrations after a few seconds of the reaction (FIG. 13). However, there was no noticeable difference in tone between the different citric extracts.

Therefore, a green and cost-effective approach can be achieved using the microwave-assisted method. The reduction of metallic ions within the solution of nanomaterials is only accomplished in the presence of both reducing and stabilizing agents.[47] Thus, these agents must be present in the reaction and come from the juice extracts.

Characterization of the Te Nanoparticles

After purification, the synthesized TeNPs using different Te precursor solution concentrations and citric extracts were characterized by TEM in terms of size and morphology with the aim to understand the effect of the extracts (FIGS. 14A-D, 15A-D, and 16A-D). TEM images showed that, for all tellurium salt concentrations, there was no difference regarding these two properties. Therefore, for the following characterization and further experiments, a concentration of 50 mM of metallic salt was chosen.

Figure 1B:
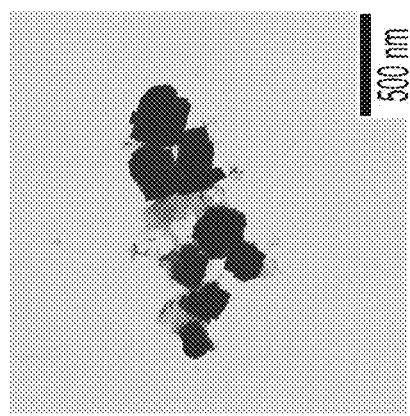
Figure 1A:
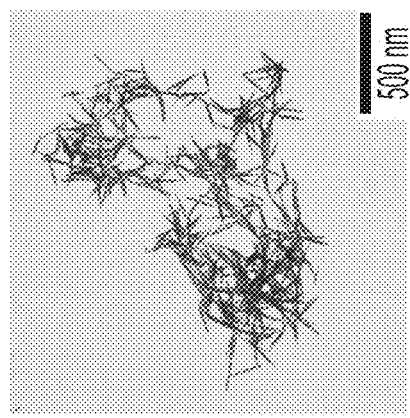

TEM images (FIGS. 1A-C) showed that the nanostructures synthesized by different extracts had different morphology and shape. Thin nanorods with both sharp ends were found for OR-TeNPs, around 50-200 nm in length and 2-15 nm in width (FIG. 1A). LEM- and LIM-TeNPs yielded a mixture of cubic-shaped nanoparticles 100-200 nm in length (FIGS. 1B and 1C, respectively).

The only effect of the tellurium salt precursor concentration, as determined by TEM, was that a larger concentration led to the formation of bigger and more numerous aggregates of nanoparticles (FIGS. 14A-D, 15A-D, and 16A-D).

Figure 2C:
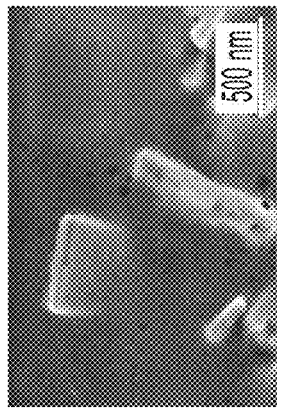
FIGS. 2A-F are scanning electron microscopy (SEM) images of OR-TeNPs (FIGS. 2A and 2D), LEM-TeNPs (FIGS. 2B and 2E) and LIM-TeNPs (FIGS. 2C and 2F). The characteristic morphology of the nanostructures was observed using SEM. The upper images (FIGS. 2A-C) correspond to secondary electrons micrographs and show the morphology of the obtained structures, while the lower ones (FIGS. 2D-F) are taken with back-scattered electrons and provide compositional contrast. The scale bar is the same for all images (500 nm).
Figure 2F:
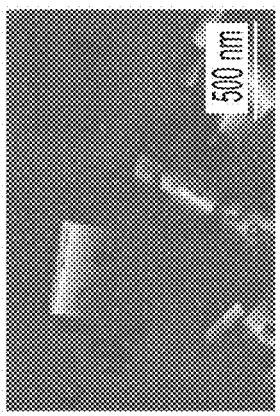
Figure 2B:
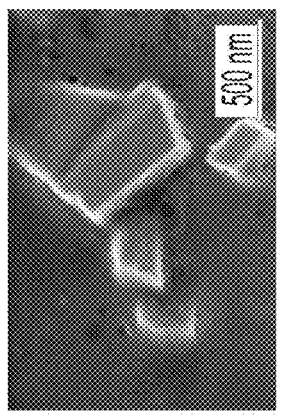
Figure 2E:
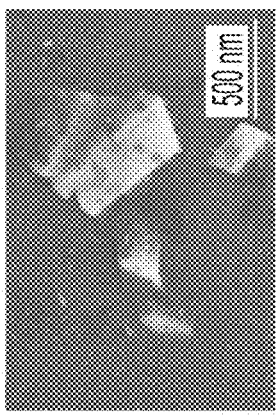
Figure 2A:
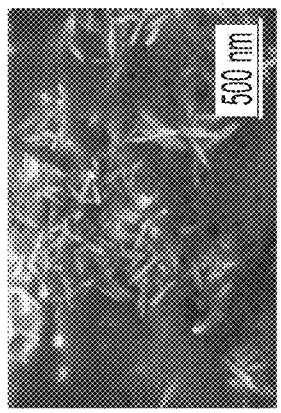
Figure 2D:
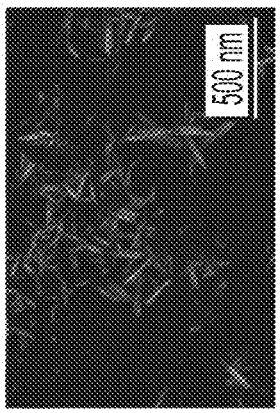

SEM characterization of OR-TeNPs (FIG. 2A) showed a homogeneous rod structure while for the LEM-TeNPs (FIG. 2B) and LIM-TeNPs (FIG. 2C), cubic-shaped structures were clearly observed. Importantly, a non-metallic organic matrix was observed surrounding the nanoparticles for all samples. The presence of the organic coating embedding the cubes for LEM- and LIM-samples made it difficult to observe very small nanoparticles together with the larger structures in standard conditions, i.e. imaging with secondary electrons. However, when the images were obtained using back-scattered electrons, whose signal depends on the atomic number Z, structures composed of Te (Z=52) were distinguished with brighter contrast than the organic coating (Z=6 and 8 for C and O, respectively). For instance, FIGS. 2D-F show representative back-scattered electrons images of OR-, LEM- and LIM-TeNPs. Only Te nanorods were seen in the OR-TeNPs sample, in agreement with the TEM characterization, while for the LEM- and LIM-samples both large crystal cubes and very small nanoparticles (around 10 nm size) immersed in the organic matrix were observed. For the LEM-TeNPs sample, some nanorods were discerned too.

To determine the elemental composition and structure of the Te nanostructures, EDX, XRD and XPS measurements were performed. EDX characterization confirmed that the electron-dense structures were composed of tellurium as proven by the presence of specific tellurium peaks in all samples (FIGS. 17A-E, 18A-E, and 19A-E). Significant peaks for carbon and oxygen were found, as well as sodium, indicating the presence of an organic coating and reaction products surrounding the nanostructures. However, it was difficult to determine if these peaks came either from the embedding matrix or from inside the rods and cubes. Summarizing, both SEM and EDX characterization allowed to determine that in LEM- and LIM-samples both cubic crystals and small particles containing tellurium coexist, while in OR-samples no cubes but well-formed Te nanorods were observed.

Figure 3:
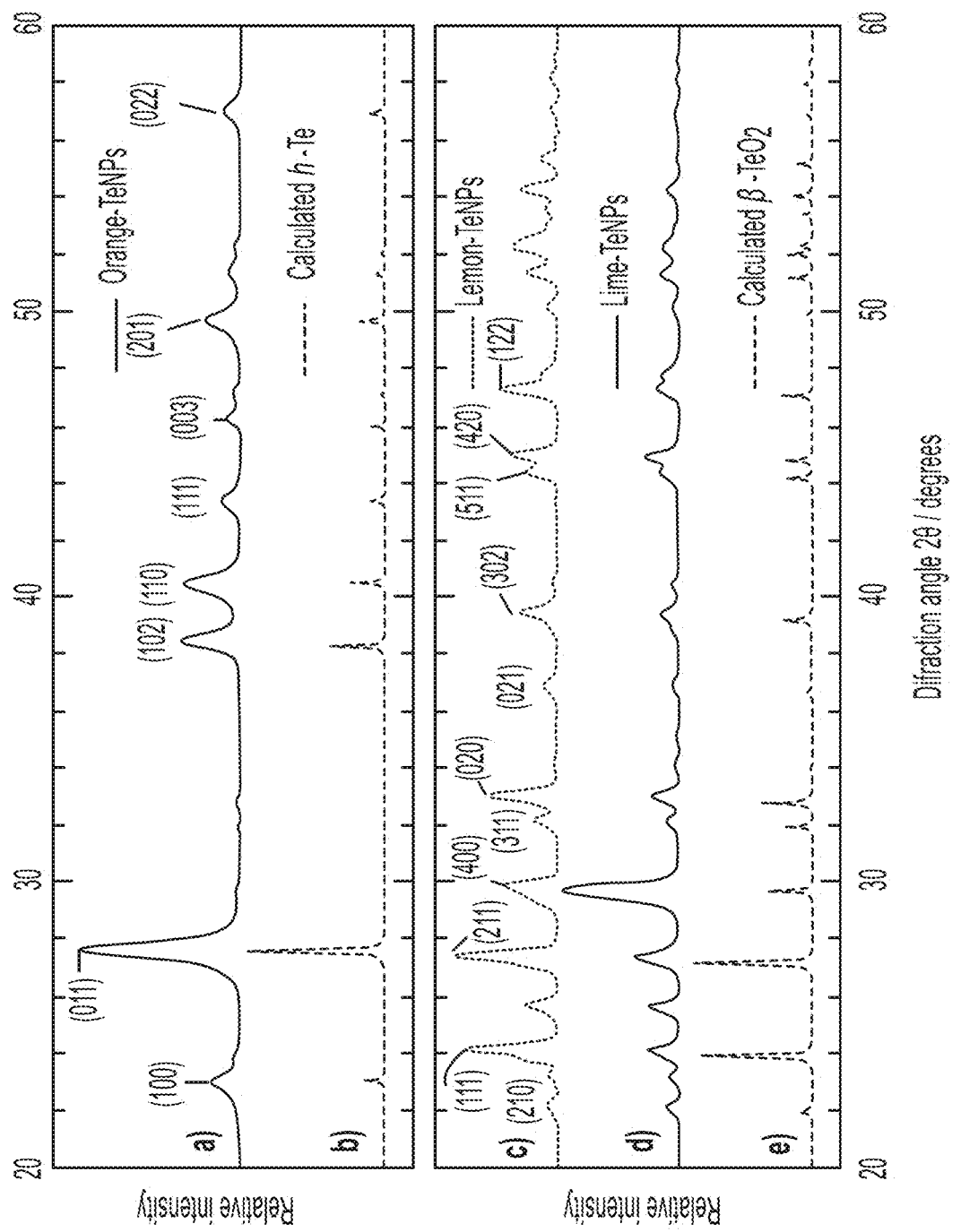
FIG. 3 is a comparison between the experimental XRD patterns for (a) OR-TeNPs, (c) LEM-TeNPs and (d) LIM-TeNPs with the calculated XRD patterns for (b) bulk hexagonal Te (h-Te)48 and (e) orthorhombic β-TeO2.49 Upper panel: Miller indices for h-Te. Lower panel: Miller indices for β-TeO2.

XRD patterns are shown in FIG. 3. The diffraction peaks for the OR-TeNPs XRD pattern (FIG. 3, a)) can be indexed to the hexagonal Te structure (h-Te, space group P3121).[48] The XRD analysis indicated the presence of foreign phases, probably tetra-oxotelluric acid and/or telluric oxide (the diffraction peaks appeared at diffraction angles $2\theta<20°$, not shown in FIG. 3). The lattice parameters calculated for the hexagonal OR-TeNPs are in good agreement with the reported values for h-Te,[48] as shown in Table 3. In the case of the XRD analysis of LEM-TeNPs and LIM-TeNPs (FIG. 3, c) and d)) both XRD patterns can be indexed to orthorhombic $\beta$-TeO$_2$ (space group Pbca).[49] The diffraction peak at $2\theta \approx 25.7°$ may correspond to the crystallographic plane (110) of tetragonal $\alpha$-TeO$_2$ (space group P43212). 50 The lattice parameters calculated for the orthorhombic LEM-TeNPs and LIM-TeNPs are also reported in Table 3.

Figure 4:
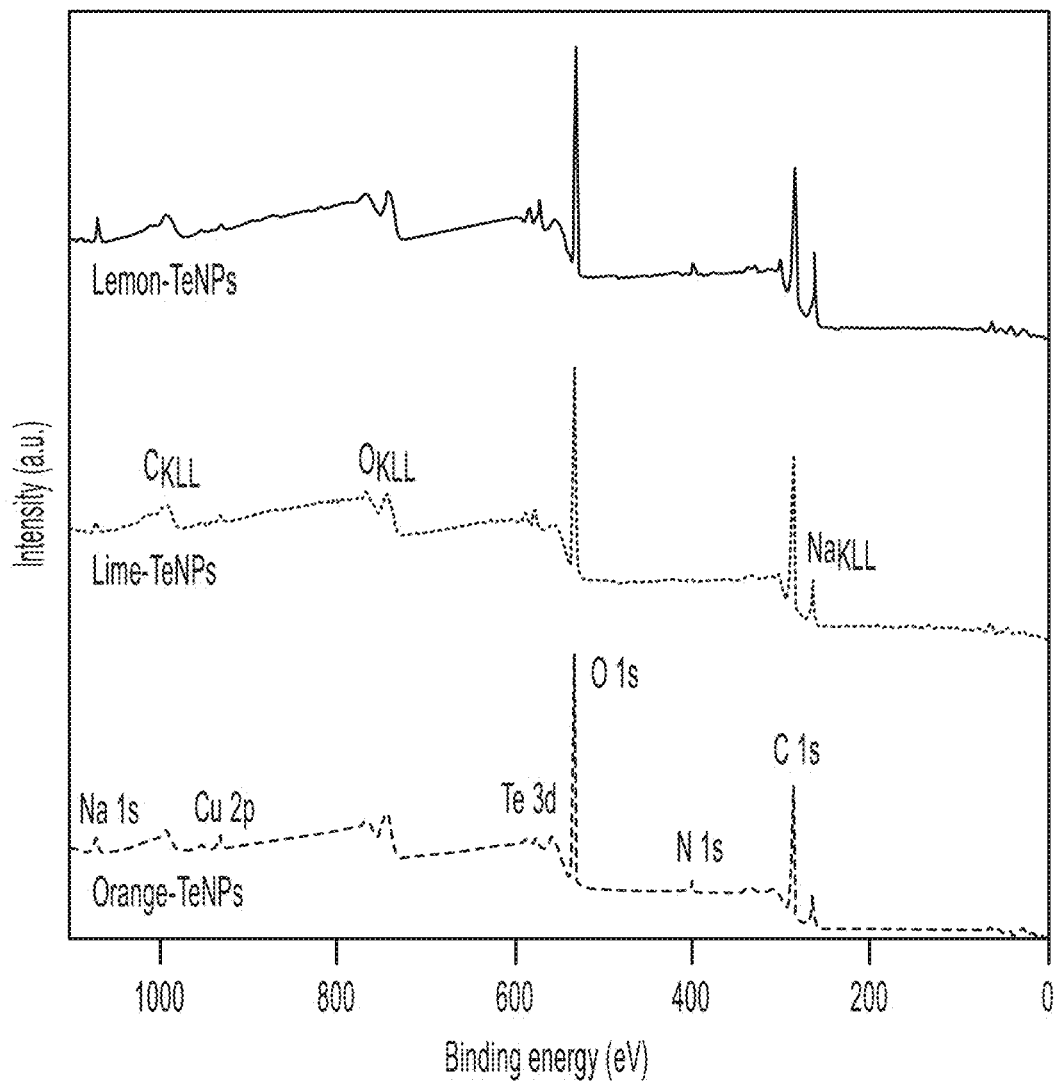
FIG. 4 is an XPS wide scan of Te nanostructures obtained from orange, lime and lemon extracts.
Figure 20:
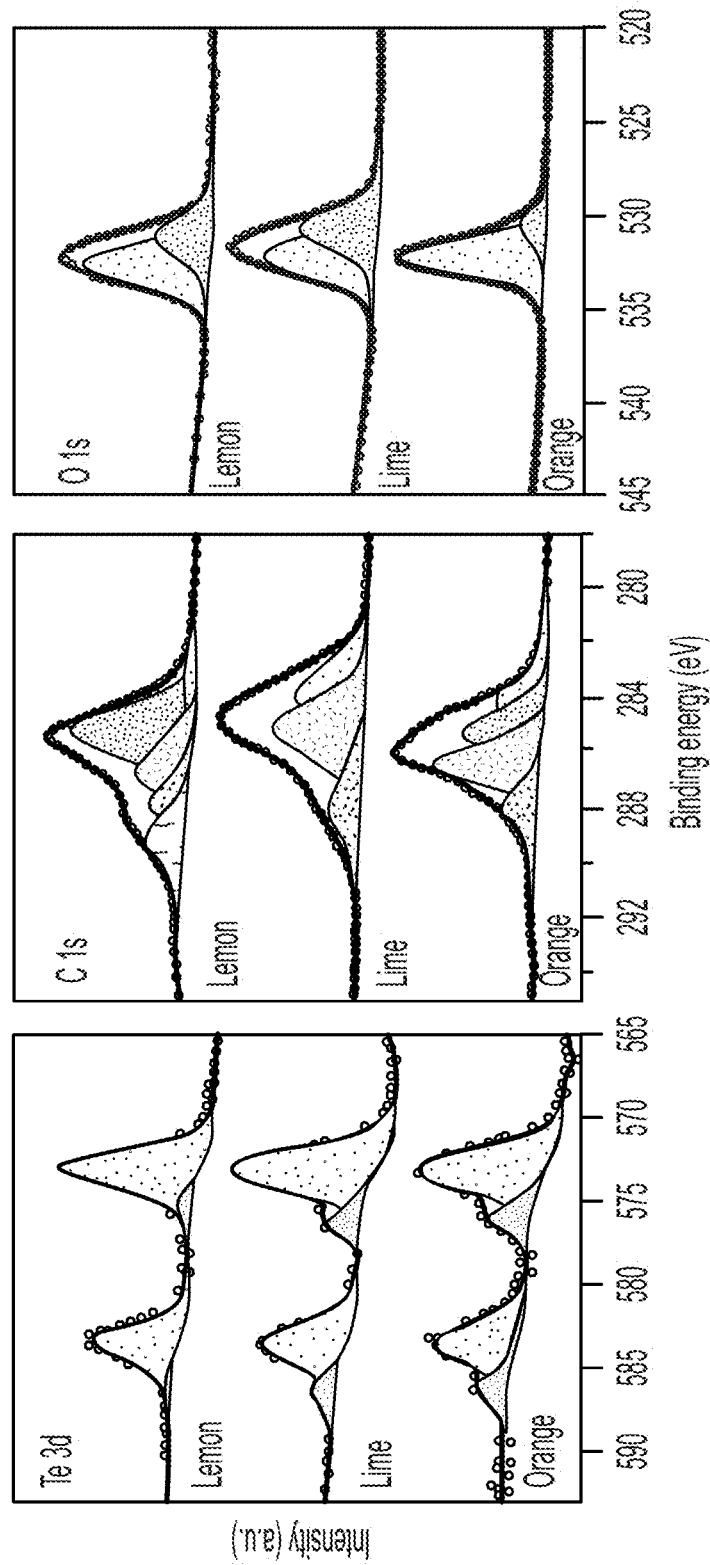
FIG. 20 is XPS Core level spectra of Te 3d (left), C is (center) and O 1s (right) of OR-, LEM- and LIM-TeNPs, respectively.

XPS was used to characterize the chemical composition and electronic states of the different Te nanomaterials. FIG. 4 presents the wide energy range scan of the Te nanoparticles obtained from the orange, lime and lemon juices. As seen, the three samples present the same elements. Apart from the tellurium, carbon, oxygen, nitrogen and sodium were detected. Copper from the substrate was also detectable, but not considered in the quantification depicted in Table 4. A comparison of the three samples evidenced that the highest Te concentration was detected in the lemon dispersion, which doubled the orange one. A detailed analysis of the core level peaks enabled the observation of certain differences between the samples, as shown in FIG. 20 and values from Table 5.

Figure 5:
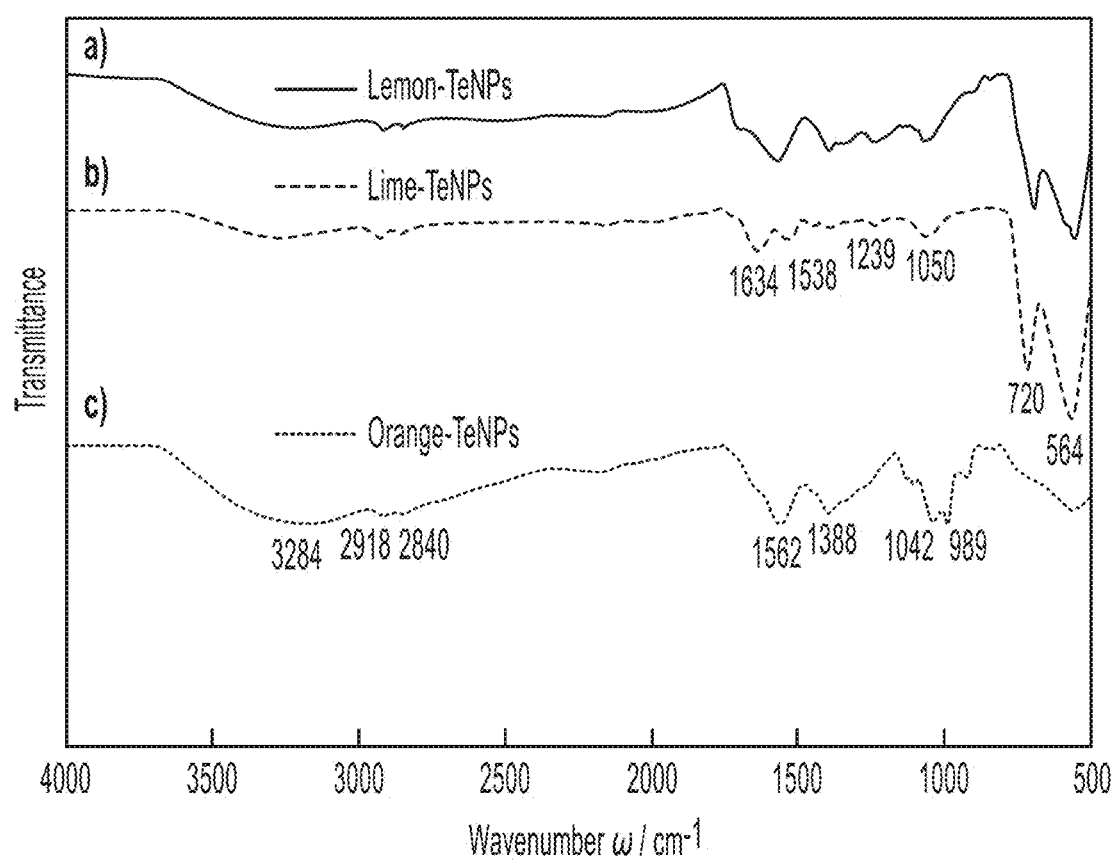
FIG. 5 is FT-IR spectra of (a) LEM-TeNPs, (b) LIM-TeNPs and (c) OR-TeNPs.

FT-IR spectroscopy measurements were completed in order to identify the capping agents in the Te nanoparticles. The FT-IR spectra of OR-, LEM- and LIM-TeNPs are shown in FIG. 5. The signals found in each of the IR spectra correspond to the most representative functional groups found in the juice from the rag and pulp of citrus fruits, i.e., sugars (e.g. sucrose, glucose, and fructose), flavonoids (e.g. hesperidin) and water-soluble pectin molecules (e.g. protopectin, calcium and magnesium pectates).[51-54] For all of the FT-IR spectra, the bands are assigned to the antisymmetric stretching vibration of —OH, —CH$_3$ and —CH$_2$ at 3284, 2918 and 2840 cm$^{-1}$, respectively. The signal at 1634 cm$^{-1}$ was associated to the deformation vibrations of water in the sample. The signals within the region of 800-1500 cm$^{-1}$ were due to the deformation vibrations of O—H and C—H bonds of pyranose rings. The peak at 1042 cm$^{-1}$ was assigned to the vibration absorption of C—O. 55 In the case of LEM-TeNPs and LIM-TeNPs, medium absorption bands due to tellurium dioxide (TeO$_2$) around 720 and 564 cm$^{-1}$ were observed, while in OR-TeNPs only weak signals at the same regions were identified, which may correspond to the presence of TeO2 in the sample.[56] These two bands are related to the symmetrical equatorial and asymmetrical axial stretching vibrations of the Te—O bonds, respectively.[57]

Stability analysis of the TeNPs after 60-days of their synthesis (using 50 mM Te-precursor solution concentration) by TEM imaging (FIGS. 21A-C) and zeta-potential measurements (Table 6) was completed. In both cases, the aged samples kept their original features.

Antimicrobial Activity of TeNPs

The antimicrobial activity of the nanostructures was tested against two different bacterial strains, MDR-*Escherichia coli* and MRSA in order to evaluate their antibacterial potential against both Gram-negative and -positive bacteria, respectively. Experiments using 24 h growth curves (FIGS. 22A-F) showed a promising antibacterial effect in a range of nanoparticle concentrations between 5 and 50 μg mL$^{-1}$ due to a decrease and inhibition in bacterial growth for both strains. This decay seemed to increase with a rise in concentration.

Figure 22B:
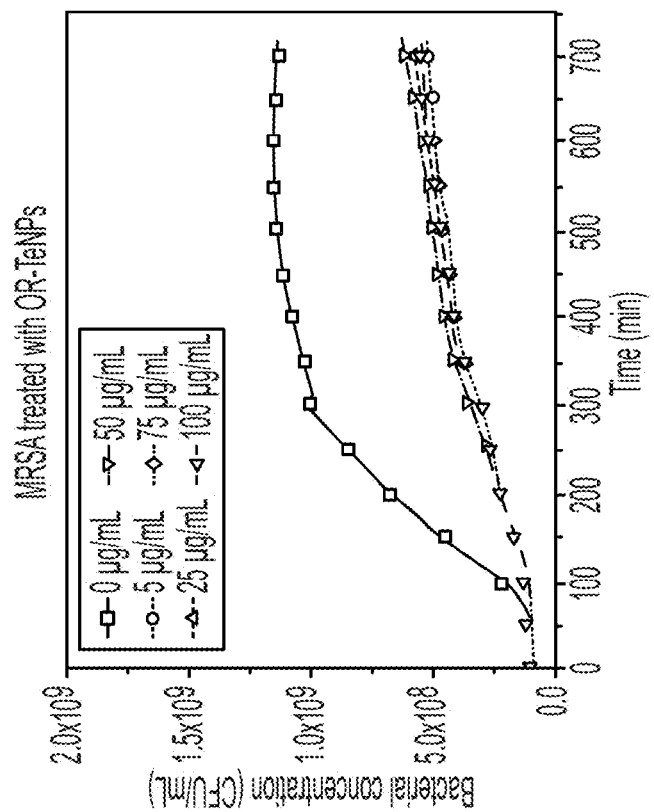
FIGS. 22A-F are charts showing that citric-mediated TeNPs decrease the growth of *Escherichia coli* (FIGS. 22A, 22C, and 22E) and *Staphylococcus aureus* (FIGS. 22B, 22D, and 22F). Growth of a 106 CFU mL$^{-1}$ suspension of *Escherichia coli* (MDR-*E. coli*) and *Staphylococcus aureus* (MRSA) over 24 h in presence of different concentrations of tellurium nanoparticles. Data=mean+/−SEM, N=3.
Figure 22A:
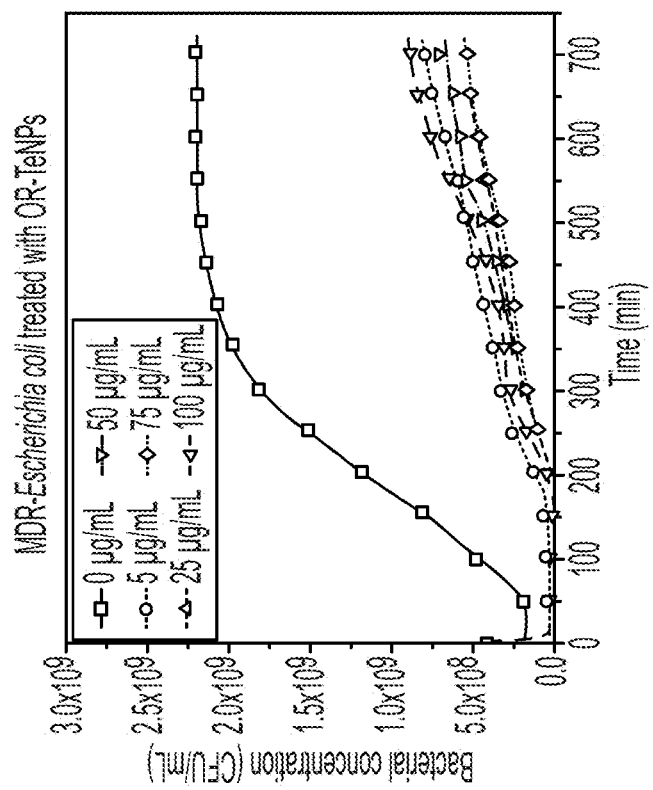
Figure 22D:
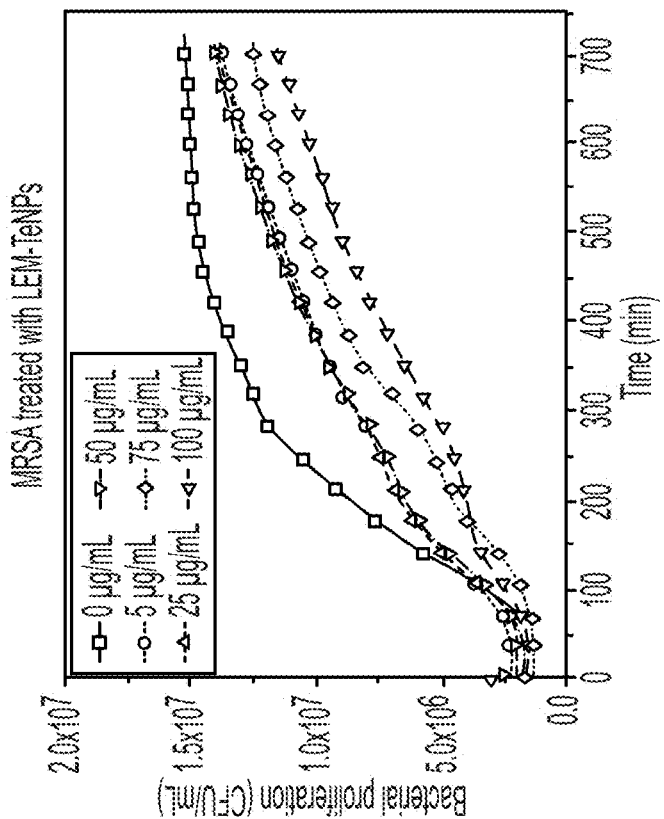
Figure 22C:
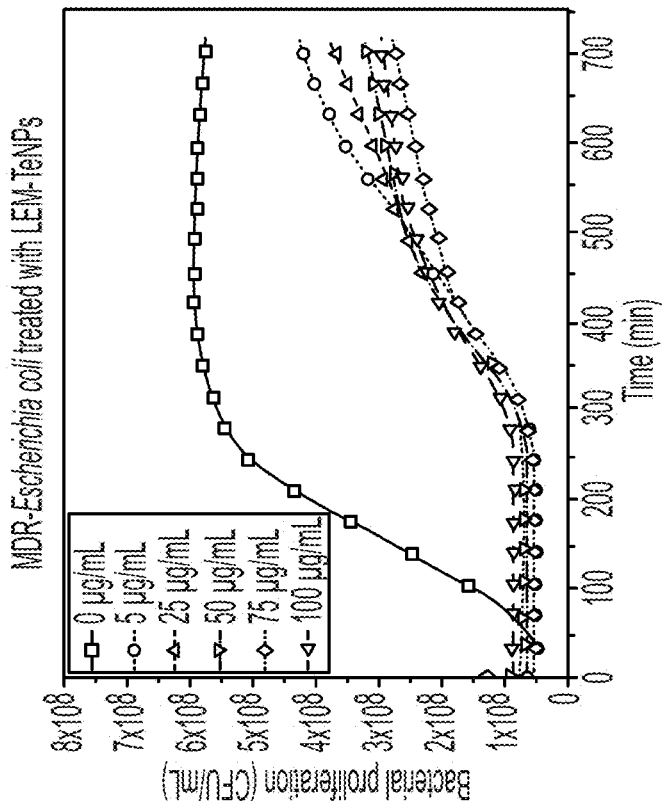
Figure 22F:
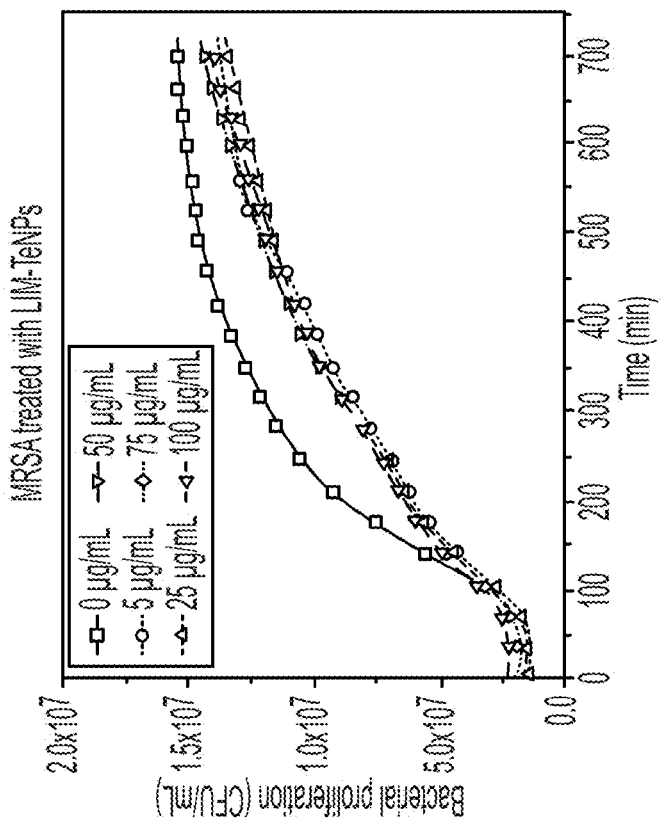
Figure 22E:
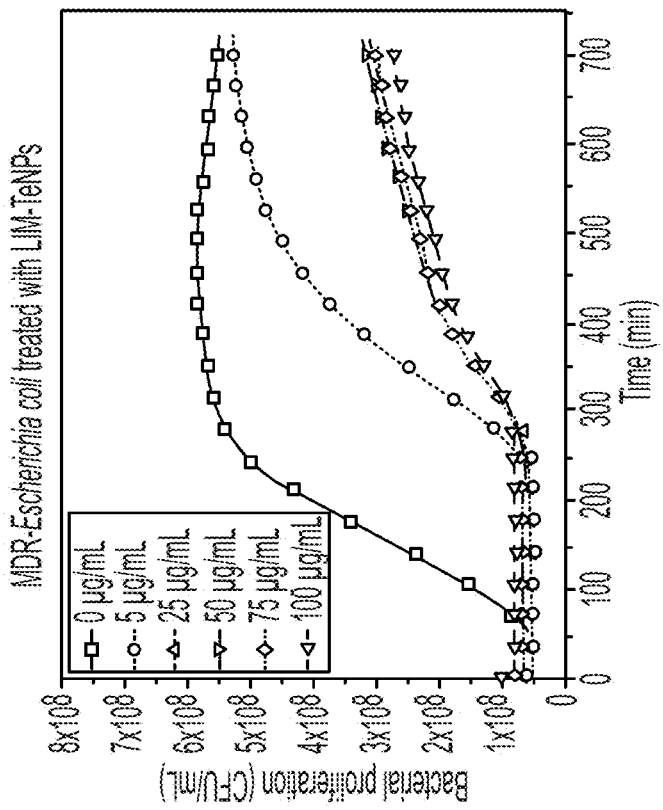

When OR-TeNPs were added to a culture of MDR-*Escherichia coli*, significant bacterial inhibition was found for the whole range of concentrations (FIG. 22A), while for LEM-TeNPs and LIM-TeNPs, the antimicrobial effect was slightly less significant (FIGS. 22C and 22E, respectively). No significant inhibition was found for the minimum concentration (5 μg mL$^{-1}$) for both cases, with a dose-dependent trend in bacterial inhibition. For MRSA experiments, OR-TeNPs showed again the highest antimicrobial effect compared to the other nanosystems, with an important impact in the bacterial cell proliferation over time (FIG. 22B). LEM-TeNPs and LIM-TeNPs showed a slight impact on the growth, with higher TeNPs concentrations meaning an increased antimicrobial effect for lemon-mediated Te nanoparticles (FIG. 22D), but no significant change for the lime-mediated Te nanostructures (FIG. 22F). The dose-dependent antibacterial effect on both bacterial strains was confirmed after modelization of the growth curves with the Gompertz analysis (FIGS. 23A-F).

Figure 6A:
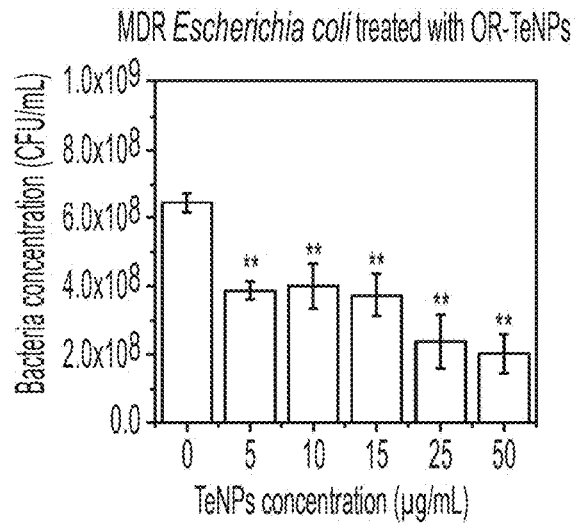
FIGS. 6A-F are colony counting assays of MDR-*Escherichia coli* (FIGS. 6A, 6C, and 6E) and methicillin-resistant *Staphylococcus aureus*, MRSA (FIGS. 6B, 6D, and 6F) after being treated for 8 h with different citric-mediated synthesized nanoparticles. Data=mean±SEM, N=3. *p<0.05 versus control (0 μg mL$^{-1}$ concentration), **p<0.01 versus control (0 μg mL$^{-1}$ concentration).
Figure 6B:
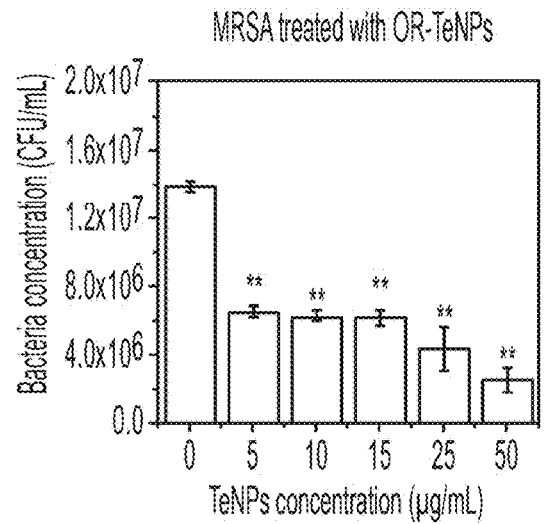
Figure 6C:
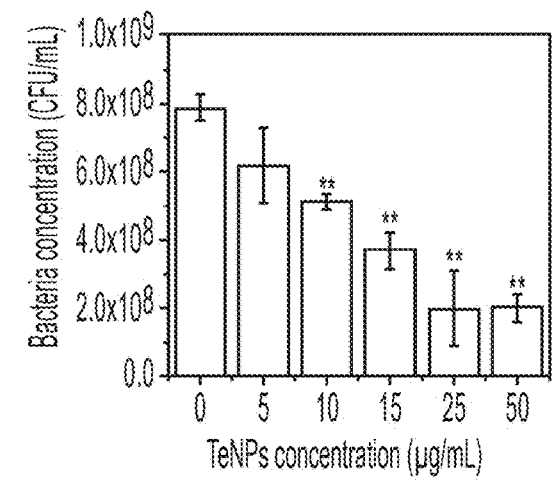
Figure 6D:
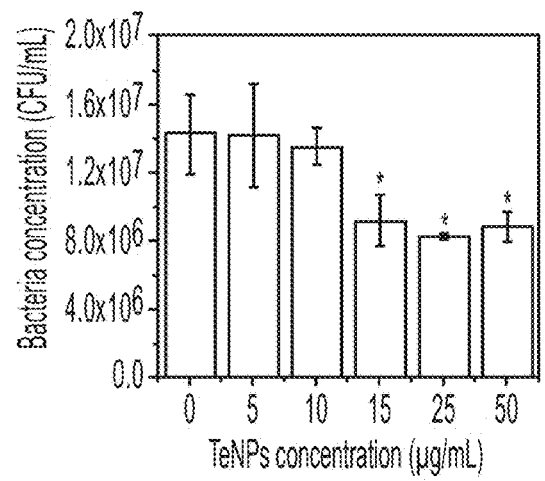
Figure 6E:
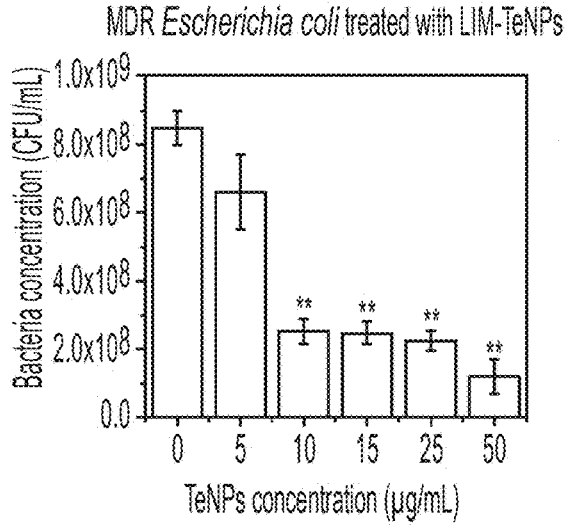

Colony forming unit assays were also performed to assess the interaction between the synthesized TeNPs and the bacterial strains MDR-*Escherichia coli* and MRSA. When MDR-*Escherichia coli* was grown with OR-TeNPs (FIG. 6A), a significant inhibition effect over cell proliferation was found, with a similar activity of all the Te nanoparticle concentrations, achieving a 50% inhibition compared to the control. For LEM-TeNPs (FIG. 6C), no significant inhibition was found for lower concentrations, while higher than 15 μg mL$^{-1}$ caused an inhibition above 50%. A similar situation was found for LIM-TeNPs (FIG. 6D), where Te nanoparticle concentrations over 10 μg mL$^{-1}$ showed an inhibition of the bacterial proliferation.

Figure 6F:
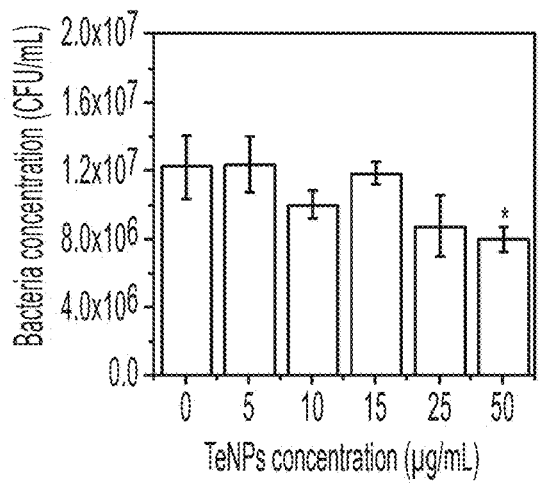

Experiments with MRSA showed a significant inhibition effect with a constant trend when OR-TeNPs were present in the bacterial culture (FIG. 6B), while no significant inhibition (or not at all) was found for lower concentrations of LEM-TeNPs (FIG. 6D) and LIM-TeNPs (FIG. 6F). Only concentrations over 15 μg mL$^{-1}$ seemed to develop a slight antimicrobial effect for both nanomaterials.

Consequently, OR-TeNPs seem to have the most important antimicrobial effect over both bacterial strains, with inhibition of the bacterial population over 50% for most of the TeNPs concentrations. This effect is especially noticeable for MDR-*Escherichia coli*, closely followed by the Gram-positive bacteria. However, no significant antibacterial effect was found when LEM- and LIM-TeNPs were cultured with MRSA, while showing inhibition for MDR-*Escherichia coli*. Overall, all the Te nanoparticles have better antimicrobial properties against Gram-negative bacteria.

$IC_{50}$ values were obtained with the aim to show the minimum inhibitory concentration for each one of the bacterial tests (Table 2).

TABLE 2

$IC_{50}$tud values (in µg/mL) for different Te nanoparticles against MDR-*Escherichia coli* and MRSA. Error values are given for each one of the parameters

| Te-nanosystems | MDR-*Escherichia coli* | MRSA |
|---|---|---|
| OR-TeNPs | 21.38 ± 3.06 | 21.98 ± 3.96 |
| LEM-TeNPs | 8.18 ± 1.25 | 33.51 ± 9.59 |
| LIM-TeNPs | 6.23 ± 0.92 | 34.68 ± 8.12 |

These values differ from others found in literature, showing a decrease of the $IC_{50}$ values for our Te nanosystems. For example, Zare et al. 58 have investigated the antibacterial effect of Te nanorods (TeNRs) using Minimum Inhibitory Concentration (MIC) as quantifying values. The TeNRs, produced by the Bacillus sp. BZ were tested against *Staphylococcus aureus* (MIC 250 µm mL$^{-1}$), *P. aeruginosa* (MIC 125 µm mL$^{-1}$), *S. typhi* (MIC µg mL$^{-1}$), and *K. pneumonia* (MIC 125 µg mL$^{-1}$).

The bactericidal effect of Te nanoparticles has been studied,[19] and it can be related to the production of reactive oxygen species (ROS) upon exposure of the bacterial cultures. Evidence so far suggests that the antimicrobial activity seems to be directly linked to the dimensions of the nanoparticles: indeed, the highest activity was shown by nanoparticles of smaller sizes. As nanoparticles decrease in size, their surface to volume ratio increase, confirming smaller is better for improving the biological reactivity. Nevertheless, size is not the sole parameter influencing antimicrobial properties of the nanoparticles: other important features are both the elemental composition and the shape.[59] It is hypothesized that the presence of the natural coating surrounding the nanoparticles can have an important effect on the biomedical properties. Moreover, tellurium oxyanions have also been found to trigger the generation of ROS, with both elements capable of reacting with intracellular thiols and forming intermediates that cause oxidative stress because of the formation of superoxide radicals.[60] Thus, even if reactive oxygen species are involved in the toxicity of TeNPs, other mechanisms may be responsible for the antimicrobial activity of these nanostructured metals. For instance, it seems that Te nanoparticles can contribute to functional damage of cell membrane or wall by disrupting the integrity of these important envelopes.[61] Some other mechanism related to the surface features of the nanoparticles may be involved, however, in conferring the toxicity to TeNPs. For instance, the presence of a natural and organic-based coating surrounding the nanoparticles can be closely related to the enhancement of the bacterial activity towards other nanoparticles systems.

Figure 7A:
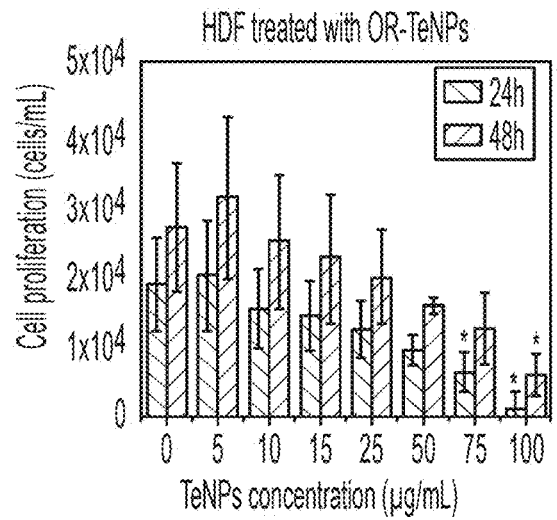
FIGS. 7A-C are MTS assay on human dermal fibroblast (HDF) in the presence of OR-TeNPs (FIG. 7A), LEM-TeNPs (FIG. 7B) and LIM-TeNPs (FIG. 7C) ranging from 5 to 100 μg mL$^{-1}$. Data=mean±SEM, N=3. *p<0.05 versus control (0 μg mL$^{-1}$ concentration), **p<0.01 versus control (0 μg mL$^{-1}$ concentration).
Figure 7B:
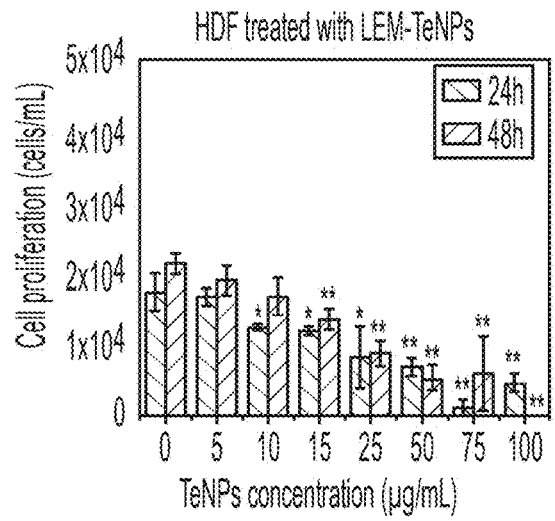
Figure 7C:
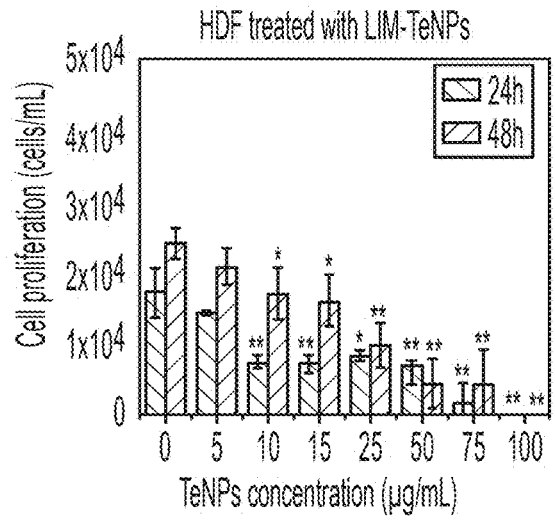

In Vitro Cytocompatibility and Cytotoxicity of TeNPs with Healthy and Cancer Cells With the aim to determine the cytotoxicity associated with the green-synthesized TeNPs in mammalian cells, in vitro cytotoxicity assays were performed with human dermal fibroblasts (HDF) and human melanoma cells for 24 and 48 h. Experiments with fibroblast cells showed a decrease in the cell viability with a Te nanoparticle concentration increase for all the systems, with a constant cell proliferation after 48 h of growth. OR-TeNPs (FIG. 7A) remained cytocompatible (with cell growth over 60%) for concentrations up to 50 µg mL$^{-1}$ for both experimental days while an important depletion of the cell proliferation was found at concentrations higher than 25 µg mL$^{-1}$ and 10 µg mL$^{-1}$ for LEM-TeNPs (FIG. 7B) and LIM-TeNPs (FIG. 7C), respectively.

Figure 8A:
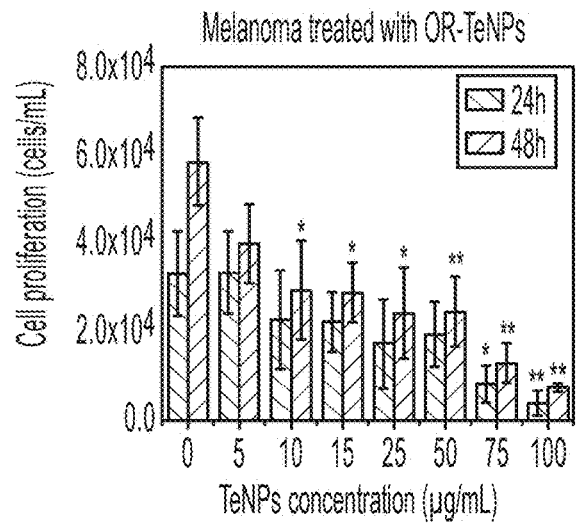
FIGS. 8A-C are MTS assay on human melanoma cells in the presence of OR-TeNPs (FIG. 8A), LEM-TeNPs (FIG. 8B) and LIM-TeNPs (FIG. 8C) ranging from 5 to 100 μg mL$^{-1}$. Data=mean±SEM, N=3. *p<0.05 versus control (0 μg mL$^{-1}$ concentration), **p<0.01 versus control (0 μg mL$^{-1}$ concentration).
Figure 8B:
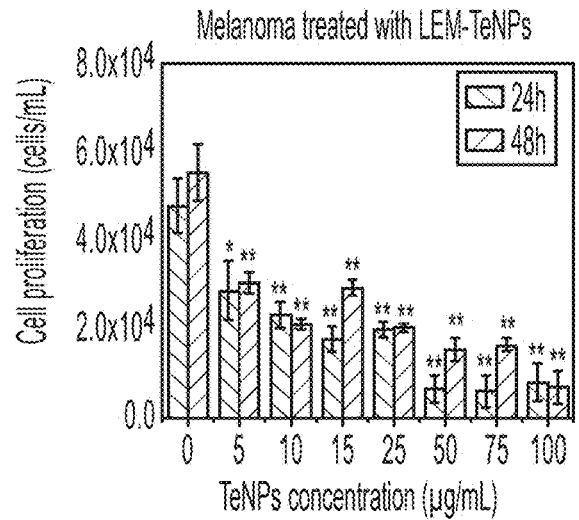
Figure 8C:
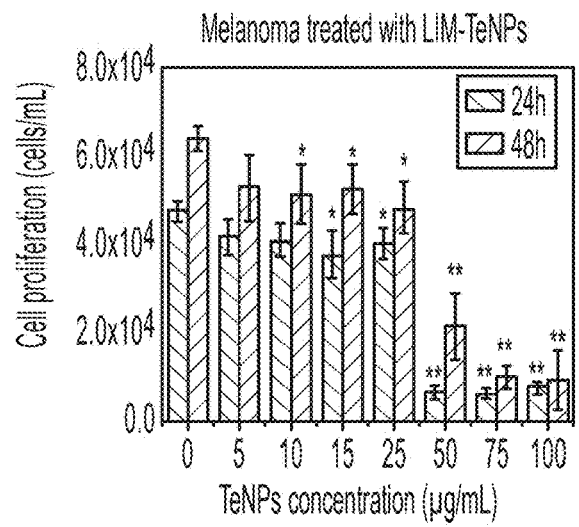

The second set of experiments was carried out with cancerous melanoma cells to evaluate the potential anticancer effect of the Te nanoparticles (FIGS. 8A-C). TeNPs concentrations from 5 to 100 µg mL$^{-1}$ were tested in all the different nanosystems with the objective of observing the potential biomedical application of the nanoparticles.

OR-TeNPs (FIG. 8A) showed inhibition of cell growth in the extended range of concentrations, nevertheless, it was accentuated at concentrations higher than 25 µg mL$^{-1}$. With similar behavior, LEM-TeNPs (FIG. 8B) presented an increasing decrease in cell proliferation. Lower TeNPs concentrations of 10 and 25 µg mL$^{-1}$ showed a specifically remarkable recession, therefore confirming that even a lower density of Te nanoparticles produced significant anticancer activity in comparison to the normal growth of the cells (presented in the graph as 0 mL$^{-1}$ columns). Finally, LIM-TeNPs (FIG. 8C) presented a different tendency in comparison to the others citric juices. Lower concentrations of metallic nanoparticles seemed to produce a non-notable delay on the cell proliferation, however, 50 µg mL$^{-1}$ and greater concentrations of TeNPs showed a sharp decrease juxtaposed with the control increase. Consequently, according with these results, it can be concluded that on average, the anticancer effect presented in these Te nanostructures is enhanced at higher nanoparticle concentrations. Nonetheless, low concentrations of LIM-TeNPs present also a good performance, allowing the use of these biogenic nanoparticles for biomedical applications with no cytotoxic effect associated.

Figure 9B:
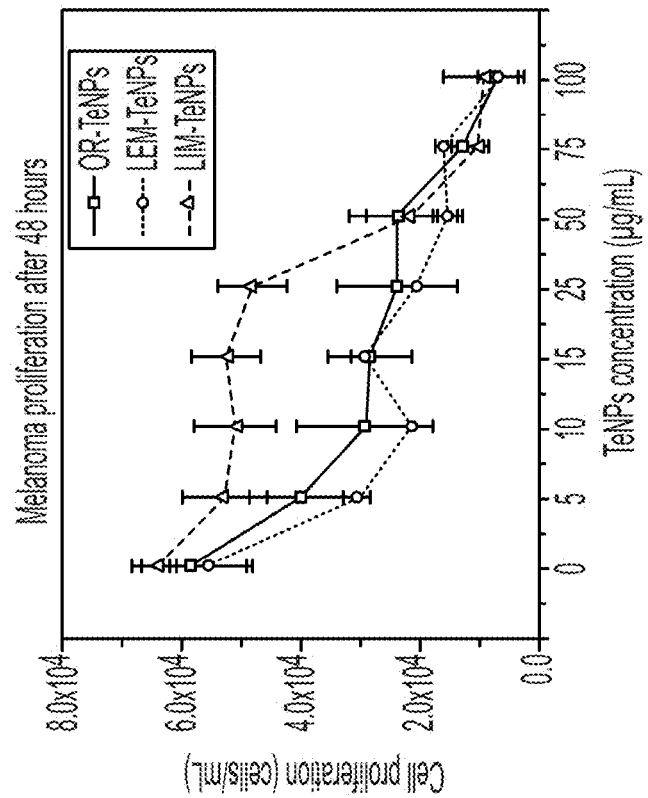
FIGS. 9A-B are MTS assays on HDF (FIG. 9A) and melanoma (FIG. 9B) cells in the presence of OR-, LEM- and LIM-TeNPs ranging from 5 to 100 μg mL$^{-1}$ after 48 h of experiment. Data=mean±SEM, N=3.
Figure 9A:
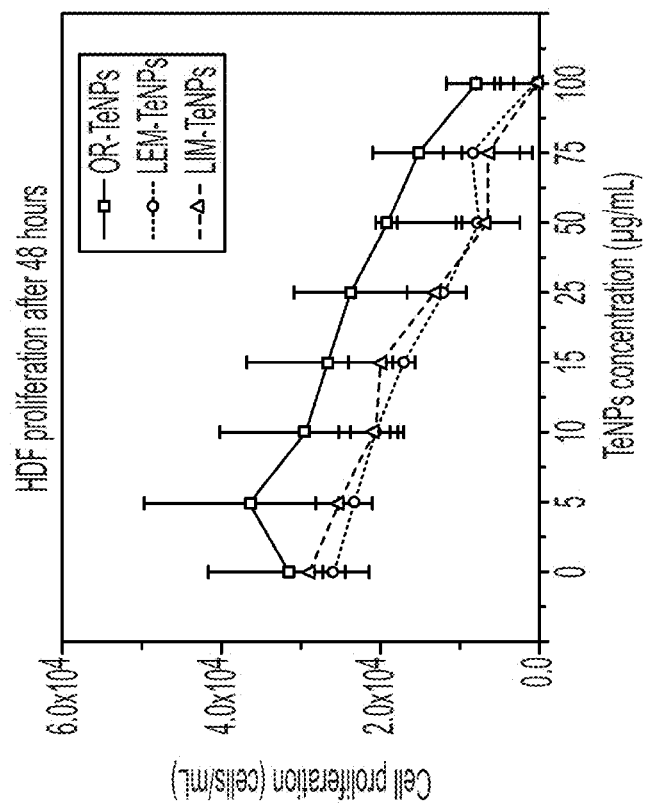

The cytotoxic effect on both cell lines was evaluated, showing a dose-dependent cytotoxic effect over the cells after 48 h of experiments (FIGS. 9A-B). The Te nanoparticles caused a decrease in the proliferation of cells for both healthy and cancer cell lines. However, the decay was more pronounced for cancer cells (FIG. 9B), showing higher cytotoxicity. OR-TeNPs showed the best cytocompatibility towards HDF cells, with a significant cytotoxic effect on melanoma cells over the whole range of Te nanoparticle concentrations (FIG. 9A). LEM- and LIM-TeNPs showed a similar trend when exposed to HDF cells, while the cytotoxic effect on melanoma cells was not so pronounced for LIM-TeNPs as it was for LEM-TeNPs, which showed a similar effect on cell proliferation as OR-TeNPs (even better at low concentrations). Overall, results from this part of the study showed for the first time that citric-derived TeNPs displayed both antibacterial and anticancer effects and a negligible cytotoxic effect for human healthy cells within an ideal range from 5 to 50 µg mL$^{-1}$.

Reactive Oxygen Species (ROS) Analysis

Figure 10B:
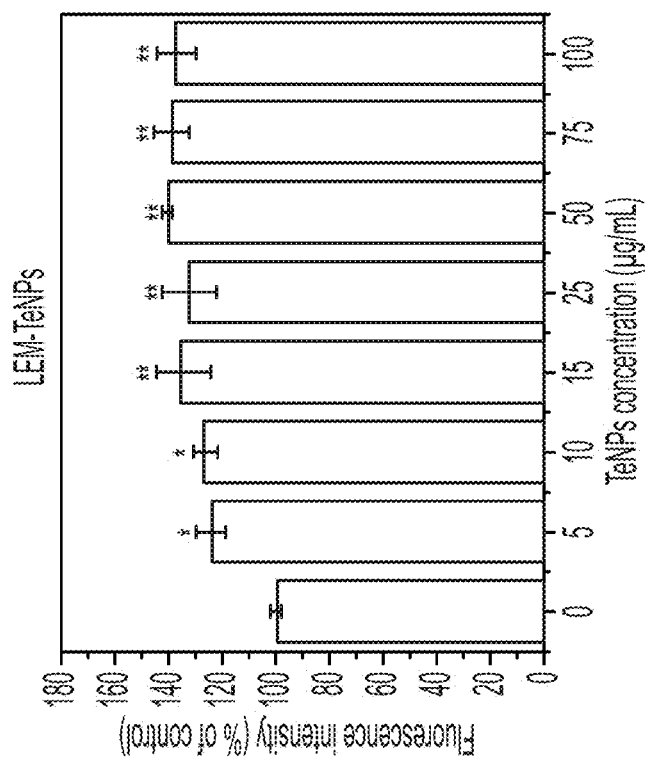
FIGS. 10A-C show Reactive Oxygen Species (ROS) analysis. The ROS production has been evaluated for the different nanoparticles (OR-, LEM- and LIM-TeNPs) in experiments with human melanoma cells (A, B, C). Data=mean±SEM, N=3. *p<0.05 versus control (0 μg mL$^{-1}$ concentration), **p<0.01 versus control (0 μg mL$^{-1}$ concentration).
Figure 10A:
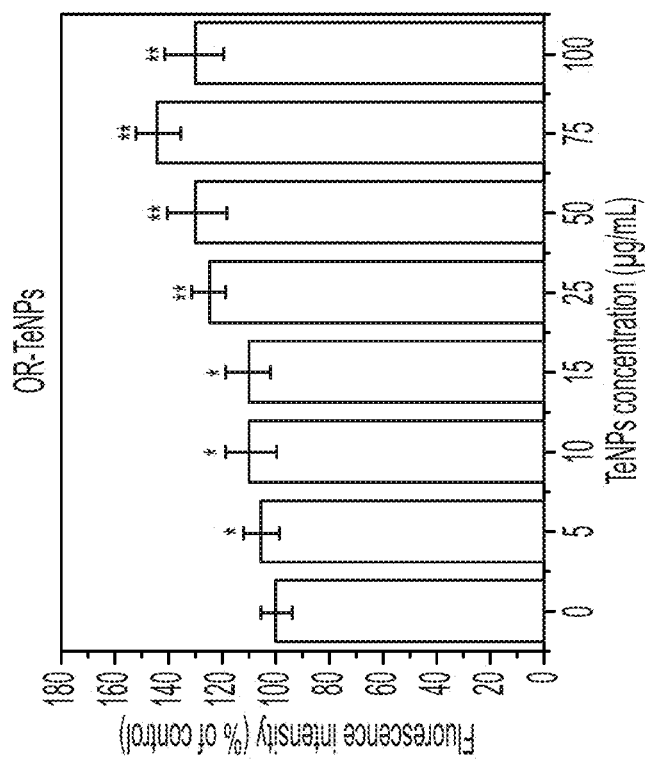
Figure 10C:
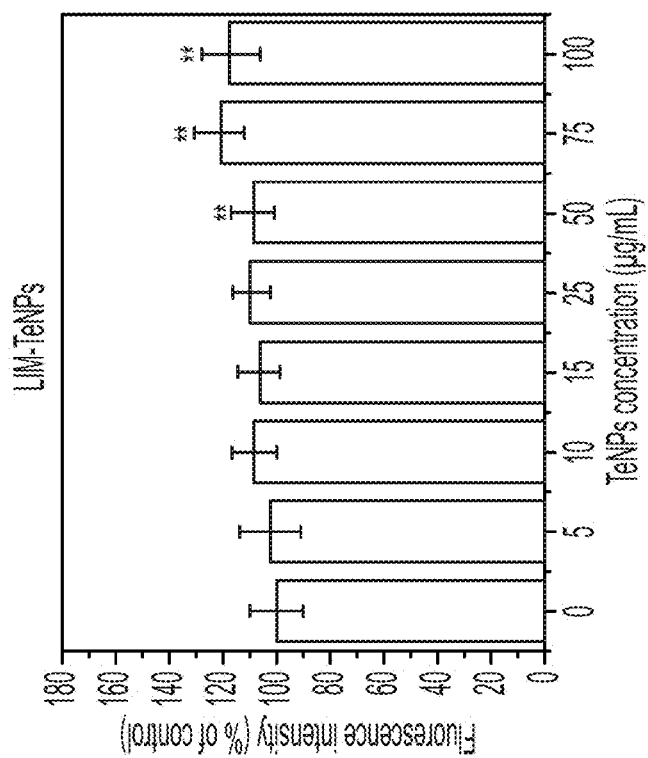

ROS analysis (FIGS. 10A-C) showed an increase in the ROS production when nanoparticles were present in the media, with a dose-dependent effect. Therefore, the increase in the number of reactive oxygen species is related to the dose-dependent anticancer behavior that was shown before.

It was hypothesized that the cytocompatibility of the Te nanostructures was associated to the organic coating present all over the Te nanostructures. This coating (composed of organic material from the synthesis) surrounding the Te surface would prevent the ion release and finally avoid cell damage. Several studies have shown an enhancement of cytocompatibility of green-synthesized nanoparticles in comparison to chemically-synthesized nanoparticles, showing no significant cytotoxic effect on the cells.[62,63]

A deteriorate ROS protective mechanisms is found in cancer cells, which may explain the anticancer effect. Several studies have reported the anticancer effect of Te compounds,[64] but only a few, if any, studies have shown this activity in tellurium nanomaterials.[65] After synthesis, some molecules remained in the coating surrounding the surface of the nanoparticles (such as citric acid and vitamin C). Both compounds are known to have anticancer properties.[66,67] Without wishing to be bound by theory, it is believed that the synergetic effects of both the metallic core and coating enhance the anticancer properties, thus presenting citric-TeNPs as a novel solution for anticancer activity with low associated cytotoxicity towards healthy cells. The anticancer effect of these citric TeNPs may also be attributed to the generation of ROS, since Te nanoparticles have been reported as strong agents for ROS-mediated apoptosis and genotoxicity.[68]

$IC_{50}$ values were calculated for the anticancer effect of the nanoparticles, rendering 0.204, 0.135 and 0.039 mg mL$^{-1}$ for OR-, LEM- and LIM-TeNPs, respectively. Therefore, it is possible to compare in terms of efficacy to other metallic nanosystems reported in literature. For instance, Hafeez et al. studied a dacarbazine laden nanoparticle (DZNP) and dacarbazine laden nanocream (DZNC) topical delivery system for the treatment of melanoma.[69] Dacarbazine (DZ) is poorly soluble in water with a short half-life in blood circulation, low rate of response with the toxic effect which ultimately limits its utilization for the treatment of skin cancer.[70] $IC_{50}$ of DZNP was 0.19 mg mL$^{-1}$, while the $IC_{50}$ was 0.63 mg ml$^{-1}$ for DZNC, with higher values than the ones obtained for our nanosystems. It is possible to compare the Te nanostructures synthesized in this work with commercially available anticancer treatments in terms of cost. For instance, dacarbazine intravenous nanopowder has a price for injection (100 mg) of around USD \$88/supply, while the price of 100 mg of $Na_2TeO_3$, the precursor of the Te nanoparticles, is around 1 dollar (plus the price of orange, lemon and lime, that rounds between 0.5-0.9 USD per kg). 71 Therefore, it is possible to conclude that the Te nanosystems presented in this work are relatively more efficient and cost-effective than other current nanoparticle-based treatments towards melanoma.

ROS production was compared with an inorganic nanoparticle, Iron Sucrose (IS) (VENOFER®, American Regent, Shirley, N.Y.). Gupta et al. found that incubation with 100 μg mL$^{-1}$ IS induced significantly higher ROS generation compared to controls. IS appeared to increase intracellular ROS in a time-dependent manner and a 60% increase from control experiments was measured after incubation with IS.[72] For all our nanoparticles systems, after 24 hours of incubation, there was around 20-30% increase from control experiments.

Cell Fixation and SEM Imaging

Figure 11A:
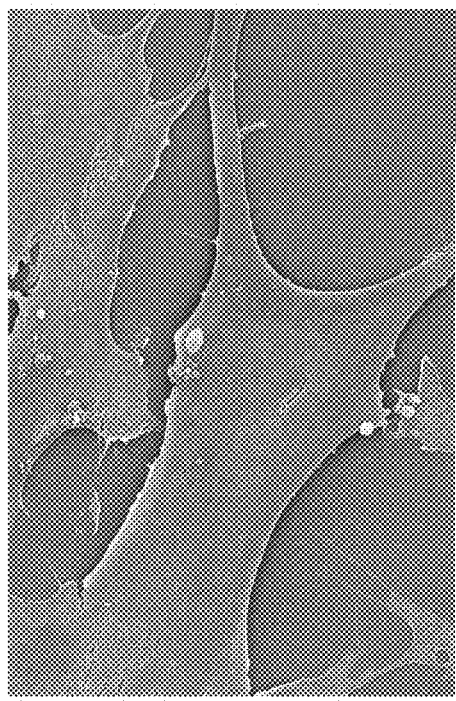
FIGS. 11A-D are SEM images showing the interaction between HDF cells and OR- (FIG. 11B), LEM- (FIG. 11C) and LIM-TeNPs (FIG. 11D). Interaction with 0 μg mL$^{-1}$ (FIG. 11A) and 50 μg mL$^{-1}$ (FIGS. 11B, 11C, and 11D) of the respective Te nanoparticles and HDF cells were analyzed.
Figure 11B:
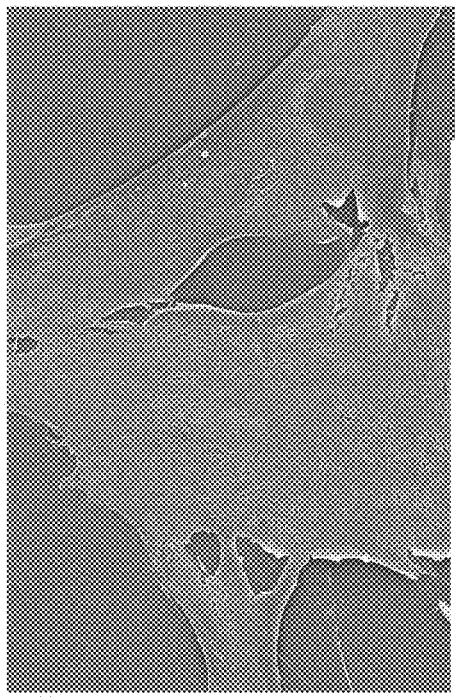
Figure 11C:
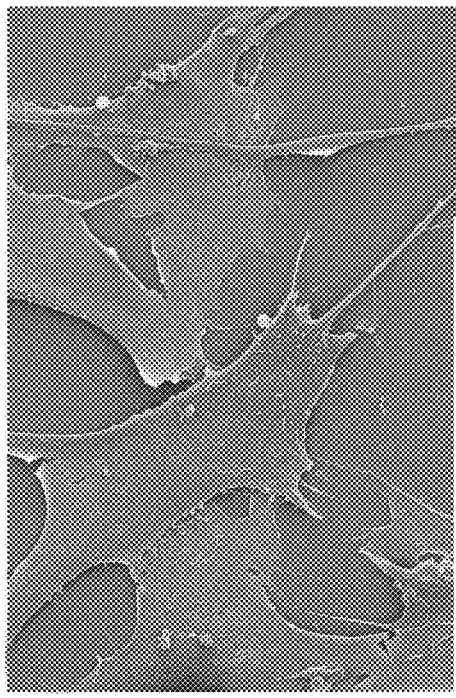
Figure 11D:
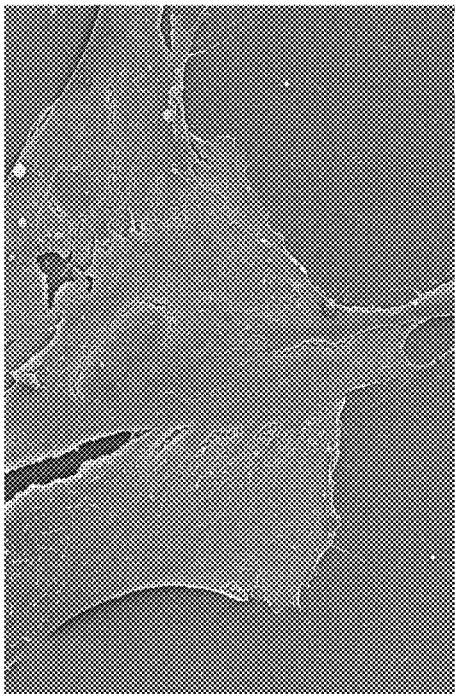

The effect of the different Te nanoparticles in the morphology and proliferation of both HDF and melanoma cells were extensively studied using SEM microscopy (FIGS. 11A-D). When HDF cells were cultured in the presence of a fixed concentration of OR- (FIG. 11B), LEM- (FIG. 11C) and LIM-TeNP (FIG. 11D) showed no significant modification on the cell morphology in contrast with the control (FIG. 11A). Therefore, these results suggest that the proliferation of the cells is maintained constant when they are grown in presence of the Te nanoparticles. Nonetheless, some discontinuities can be observed on the membrane previous to rupture (without any other change in the structure), which eventually ends in cell death. Hence, the tendency of these results suggested a necrotic mechanism.[73,74]

On the contrary, when melanoma cells were cultured in the presence of a fixed concentration of OR- (FIG. 12B), LEM- (FIG. 12C) and LIM-TeNPs (FIG. 12D) significant morphological changes were observed with respect to the control (FIG. 12A). In all cases, the cell membrane suffered significant damages and showed different stages on cell death mechanism. Swelling on the membrane appeared due to the rearranging of the structures in the cytoskeleton (FIG. 12C) as a consequence of the apoptosis mechanism induced by the cells.[75] Finally, these formations produced cell membrane rupture in various fragments (FIGS. 12B and 12D) that end in cell death.[76] Therefore, a significant decay in cell proliferation can be found, with important differences between the treated and untreated samples.

Conclusions

In this work, an effective green and environmentally-friendly synthesis route for TeNPs synthesis was presented, employing three citric juices (orange, lemon and lime) as unique reducing and stabilizing agents in a reaction that was accomplished in seconds. TeNPs, with either rod-like or cubic-shaped morphologies were extensively characterized in terms of composition and chemical structure, before being employed as biomedical agents. Inhibition of antibiotic-resistant bacterial growth was found in a range of concentrations between 5 and 50 μg mL$^{-1}$ with a main mechanism of inhibition related to ROS production. Cytotoxicity studies were accomplished showing a dose-dependent anticancer effect towards human melanoma cells in a range of concentrations up to 100 μg mL$^{-1}$, remaining cytocompatible towards human healthy fibroblast cells at concentrations up to 50 μg mL$^{-1}$. Therefore, citric juice-mediated TeNPs are shown here as a novel nanosized agent with antimicrobial and anticancer properties, enhanced cytocompatibility, with an easy synthesis that does not use harsh materials or the production of toxic by-products. These findings suggest that green-synthesized TeNPs can overcome many of the shortcomings of traditionally synthesized nanomaterials, providing promising evidence for future research and applications in medicine for this rare metalloid in its nanometer scale, for instance, in antibacterial wound dressings.

Supplementary Information

TEM Characterization of TeNPs

OR-, LEM- and LIM-TeNPs were prepared using a microwave-assisted method with a decrease of the Te-precursor solution concentration from 100 to 25 mM, leading to some changes in the morphology and aggregation of the structures, with the presence of clusters at high concentrations (FIGS. 14A-D, 15A-D, and 16A-D).

For OR-TeNPs, needle-like nanostructures were found to generate clusters at high concentrations, with less presence of the aggregates when the concentration of Te-precursor solution was decreased, while the morphology was the same for all the samples (FIGS. 14A-D).

For LEM-TeNPs, cubic-shaped nanostructures were found, with a size-metallic salt concentration dependence (FIGS. 15A-D). For the lowest concentration, no cubic structures were found, while some nanorod-like structures were observed.

For LIM-TeNPs, cubic-shaped nanostructures were found, with some agglomerates for the highest Te-precursor solution concentrations (FIG. 16A-D). The agglomeration decreases when the metallic salt concentration is lowered. The presence of some nanorods together with the cubic-like structures were noticed.

EDX Characterization

Different areas of each sample were analyzed in order to assess the substances present in the nanostructures. The characterization confirmed that the electron-dense nanoparticles were composed of tellurium as proven by the presence of specific tellurium peaks in all samples. For OR-TeNPs (FIGS. 17A-E), the analysis indicated the presence a single kind of nanostructures, Te nanorods, surrounded by a matrix composed mainly of carbon, oxygen, sodium and potassium. As the ratio between the oxygen content and the carbon content is almost the same in area 1, with lots of nanorods, and in area 2, with mainly organic coating, we can infer that the nanorods are mainly composed of metallic Te. For LEM-TeNPs (FIGS. 18A-E) and LIM-TeNPs (FIGS. 19A-E), analysis of the different positions corroborated the presence of two tellurium structures, small tellurium nanoparticles, visible in the back-scattered electrons SEM images, and bigger cubic-shape crystals. In all samples, significant oxygen, carbon and sodium peaks were also identified, indicating the presence of a matrix embedding the nanostructures coming from the citric extract and the salt used in the synthesis process. Focusing our attention on FIGS. 18A-E corresponding to LEM-Te NPs, the ratio oxygen (atomic %)/carbon (atomic %) in Spot 1, on top of a big cubic-shape crystal, is four times higher than that in Area 2 without big crystal, which indicates that the big crystal contains a significant amount of oxygen. Thus, such a higher content of oxygen suggests partial oxidation of the tellurium core, in agreement with the XRD patterns (FIG. 3). A similar case is deduced from FIGS. 19A-E corresponding to LIM-Te NPs. Finally, potassium, magnesium and calcium species were also found in all the spectra and it has been hypothesized that their presence may be derived from the orange, lemon and lime themselves, as well as from the metallic salt (sodium-containing tellurite). As described in the literature, citric juices contain a good amount of potassium 1, being the metal in highest content, with values between 15 and 300 mg/L. The detected silicon amount came from the use of Si substrates for the sample deposition.

XRD Characterization

XRD patterns are shown in FIG. 3. The lattice parameters calculated for OR-TeNPs and the orthorhombic LEM-TeNPs and LIM-TeNPs are also reported in Table 3.

TABLE 3

Lattice parameters calculated for Orange-TeNPs (h-Te) and, Lemon-TeNPs and Lime-TeNPs ($\beta$-TeO$_2$)

| Sample | a/Å | b/Å | c/Å |
| --- | --- | --- | --- |
| OR-TeNPs | 4.476 | 4.476 | 5.856 |
| h-Te[2] | 4.456 | 4.456 | 5.921 |

TABLE 3-continued

Lattice parameters calculated for Orange-TeNPs (h-Te) and, Lemon-TeNPs and Lime-TeNPs ($\beta$-TeO$_2$)

| Sample | a/Å | b/Å | c/Å |
| --- | --- | --- | --- |
| LEM-TeNPs | 12.019 | 5.419 | 5.546 |
| LIM-TeNPs | 12.045 | 5.434 | 5.547 |
| $\beta$-TeO$_2$[3] | 12.035 | 5.464 | 5.607 |

XPS Analysis

FIG. 4 presents the wide energy range scan of the Te nanoparticles obtained from the orange, lime and lemon juices using XPS analysis. Quantification is reported in Table 4. A comparison of the three samples evidenced that the higher Te concentration was detected in the lemon dispersion, which doubled the orange one.

TABLE 4

Composition of the samples extracted from the wide energy range scans displayed in FIG. 20.

| | Composition at % | | | | |
| --- | --- | --- | --- | --- | --- |
| | C | N | Na | O | Te |
| OR-TeNPs | 59.2 | 1.7 | 1.0 | 37.7 | 0.4 |
| LIM-TeNPs | 65.0 | 1.1 | 0.6 | 32.6 | 0.6 |
| LEM-TeNPs | 62.5 | 1.1 | 1.2 | 34.4 | 0.8 |

Detailed analysis of the core level peaks enabled the observation of certain differences between the samples. FIG. 20 (left) presents the Te 3 d core level peak of the samples. Two components are present in the Te 3 d; the first component at 573±0.1 eV corresponds to the metallic component of Te 3 d5/2 and the other component at 576±0.2 eV, corresponds to the oxidized component 4, 5. By having a look to the proportion between the metallic and the oxidized components (Table 5), LEM-TeNPs—the samples with higher metallic Te proportion—only presented a 6 at % of Te oxidized, whereas the amount of oxidized Te is 18 at % in OR-TeNPs. The difference between these results and those obtained with the other techniques (EDX, XRD) is due to the inherent characteristics of the technique: XPS is a surface analysis technique where the average depth of analysis for a XPS measurement is only a few nm, much smaller than the penetration depth in the measurements by EDX and XRD.

The analysis of the C is core level spectra of the samples revealed significant differences between the samples (FIG. 20 (center)). Five components were used for the fitting, all of them were forced to have the same full width at half maximum (FWHM). These components corresponded to C—C/C—H bonds at 285±0.2 eV; C—O/C—N bonds at 286.3±0.2 eV; C=O bonds at 288.1±0.2 eV and O—C=O bonds at 289±0.2 eV. These four components are typical from organic compounds.[6] The fifth component that appeared at a lower biding energy (284±0.2 eV) can be attributed to carbon in the sp2 configuration.[7] The relative intensity of each component varies depending on the sample. Table 5 displays the proportion of each component of the C 1s and O 1 s. OR-TeNPas—the one with the highest amount of oxygen—is the only sample in which the main component of the C 1 s is not the C—C bond, and the C—O contribution is the most abundant. In the three samples, the C=O contribution is similar (around 13 at %). Only in the lemon sample, the O—C=O contribution is representative and reaches 13 at %.

The 0 is core level of the samples can be fitted into two components, one at 532.3±0.2 eV and another less intense at 530.8±0.2 eV (FIG. 20 (right)). The first component is in the energy range characteristic of carbon-oxygen bonds in organic compounds.[6] The second component is close to the energy range of Te oxide [NIST database https://srdata.nist.gov/xps/] although by having a look to the amount of Te oxide of each sample (Table 5), it is clear that there are also other contributions to this component. The elements present in small amounts (i.e., N, Na, Cu) can also contribute to this component when bonded to oxygen.

TABLE 5

Components used for the fitting of the C 1s and O 1s core levels.

| | Te | TeO$_x$ | C—C | C—O | C=O | O—C=O | sp$^2$ | O1 | O2 |
|---|---|---|---|---|---|---|---|---|---|
| OR-TeNPs | 82 | 18 | 30 | 41 | 12 | 0 | 17 | 83 | 17 |
| LIM-TeNPs | 86 | 14 | 42 | 11 | 14 | 2 | 31 | 59 | 41 |
| LEM-TeNPs | 94 | 6 | 49 | 21 | 13 | 13 | 5 | 70 | 30 |

Stability Analysis

Figure 14A:
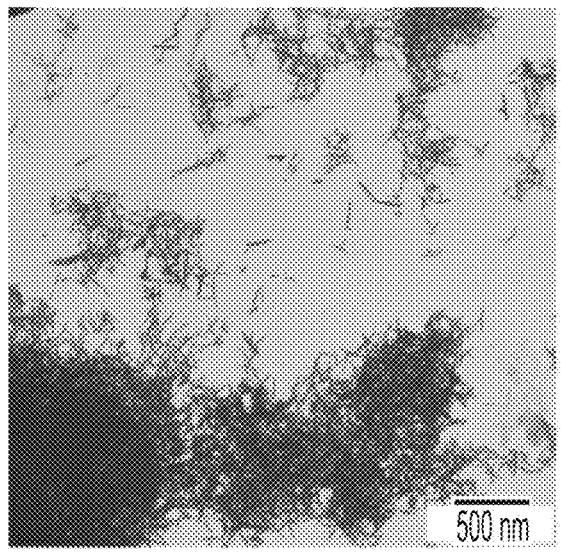
FIGS. 14A-D are TEM characterizations of OR-TeNPs when 100 mM (FIG. 14A), 75 mM (FIG. 14B), 50 mM (FIG. 14C) and 25 mM (FIG. 14D) Te-precursor solution concentration was used.
Figure 14B:
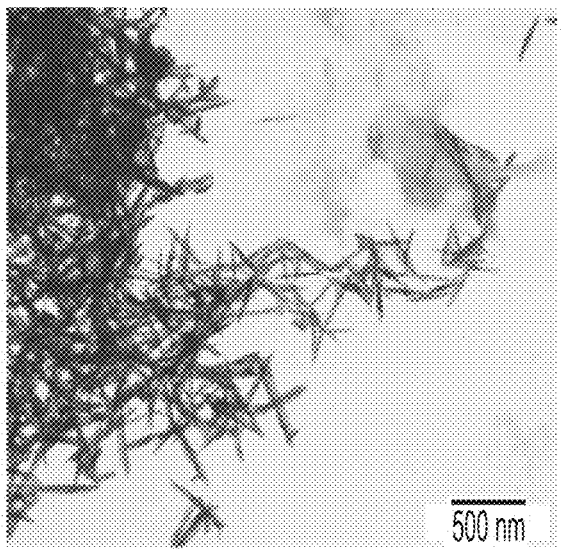
Figure 14C:
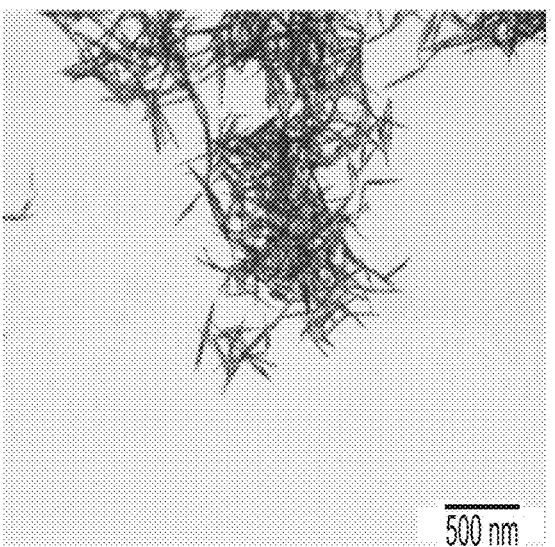
Figure 14D:
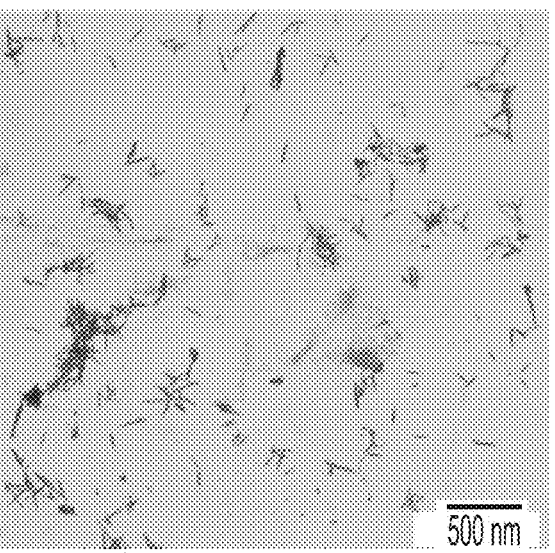
Figure 15A:
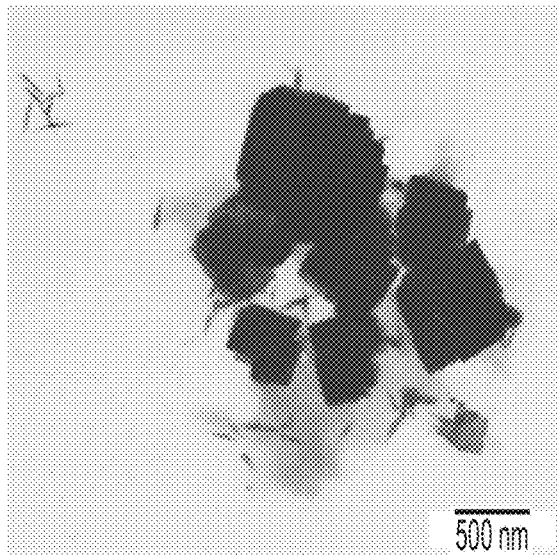
FIGS. 15A-D are TEM characterizations of LEM-TeNPs when 100 mM (FIG. 15A), 75 mM (FIG. 15B), 50 mM (FIG. 15C) and 25 mM (FIG. 15D) Te-precursor solution concentration was used.
Figure 15B:
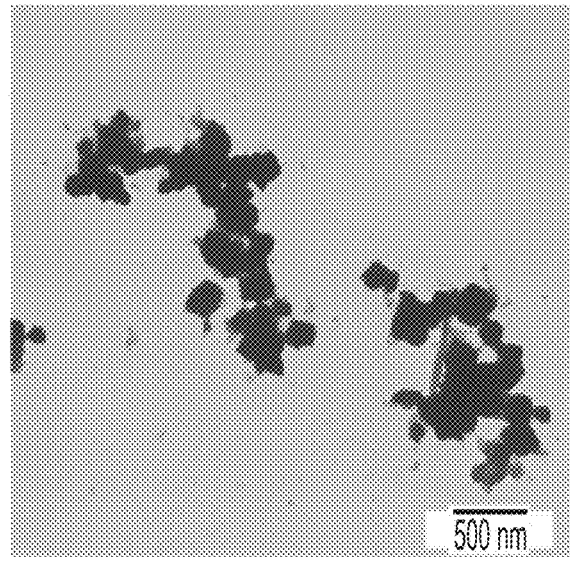
Figure 15C:
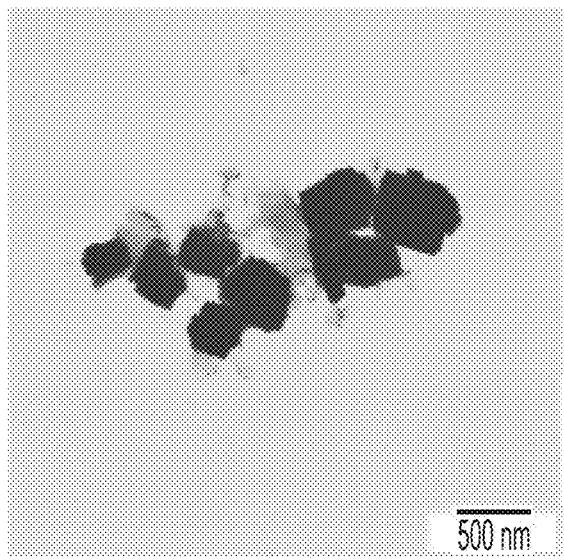
Figure 15D:
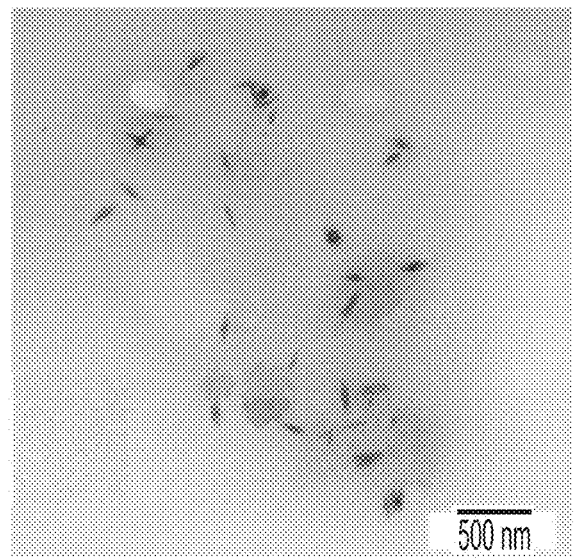
Figure 16A:
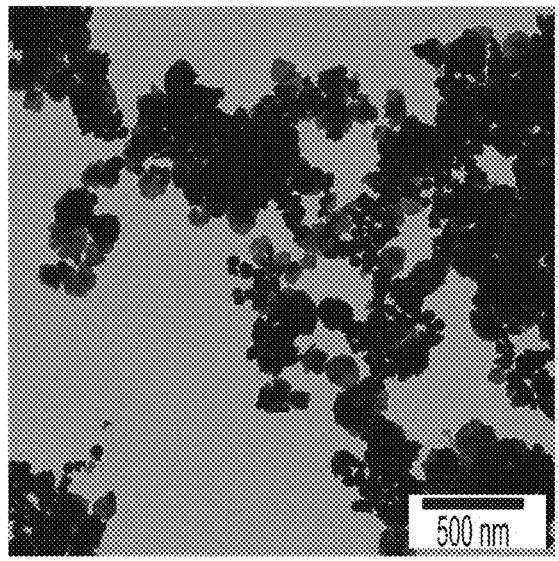
FIGS. 16A-D are TEM characterizations of LIM-TeNPs when 100 mM (FIG. 16A), 75 mM (FIG. 16B), 50 mM (FIG. 16C) and 25 mM (FIG. 16D) Te-precursor solution concentration was used.
Figure 16B:
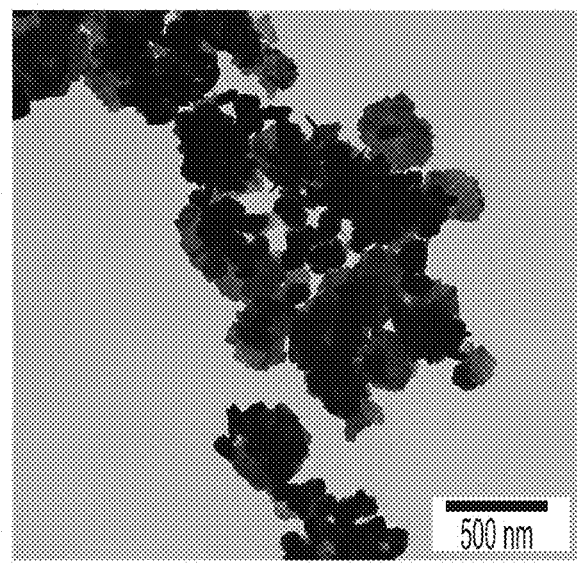
Figure 16C:
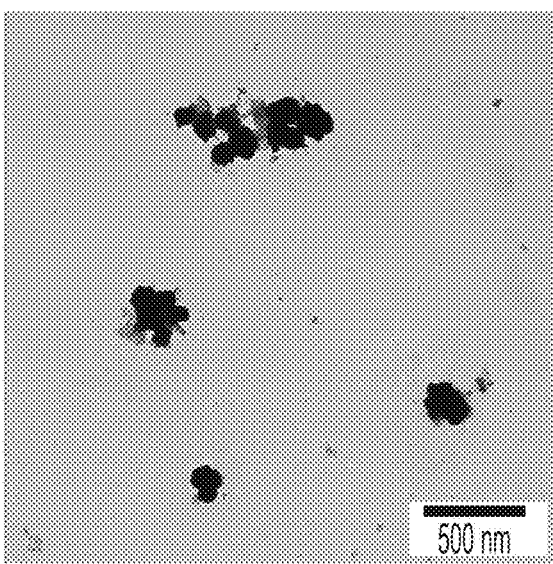
Figure 16D:
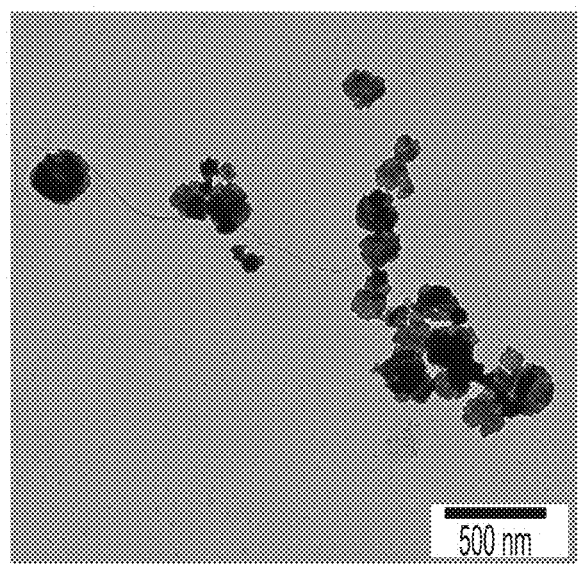
Figure 17A:
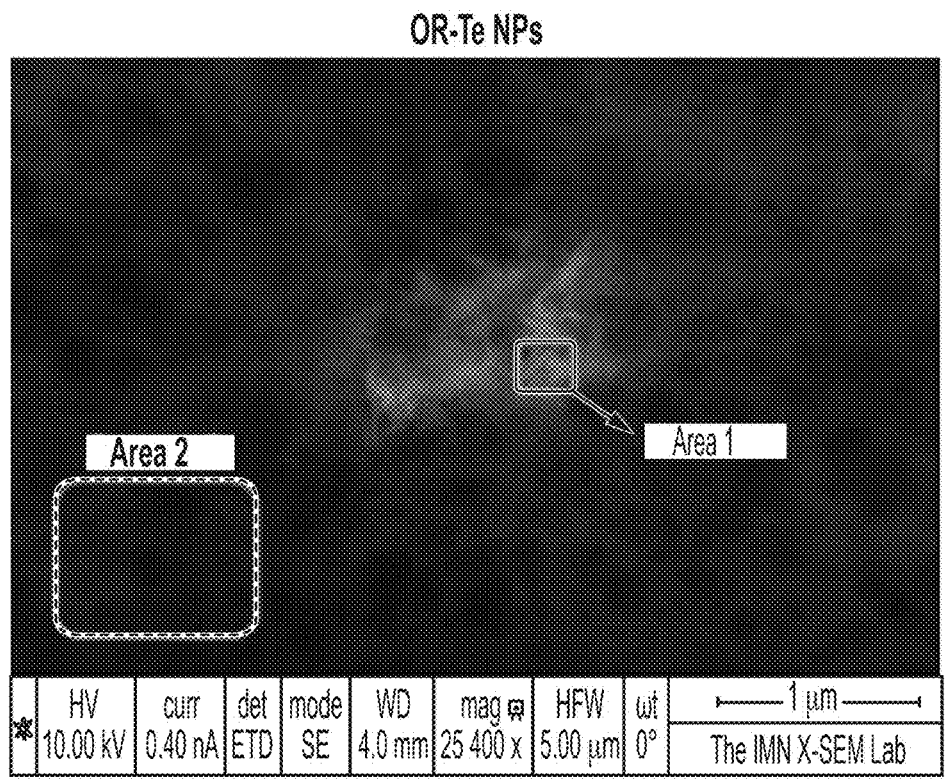
FIGS. 17A-E are characterizations of OR-TeNPs, showing the presence of tellurium within the sample, as well as carbon, oxygen and sodium. The spectra were taken in different zones: Area 1 corresponds to the tellurium nanorods embedded in an organic matrix, and Area 2 corresponds to the surrounding matrix with some buried nanostructures not observed in the image (some tellurium is also detected there).
Figure 17B:
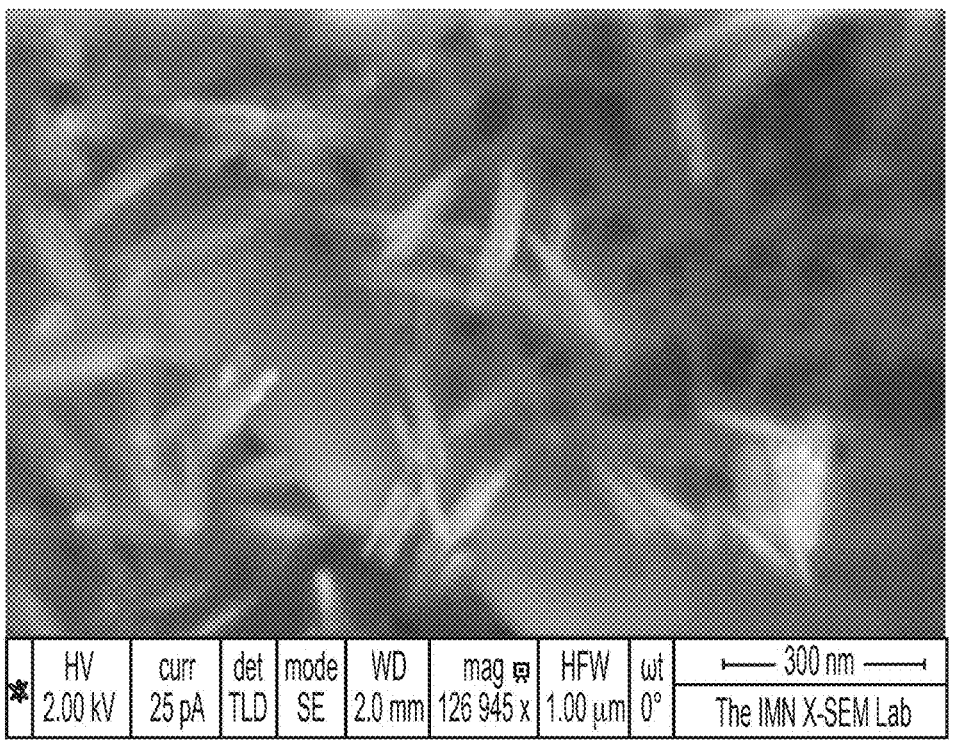
Figure 17C:
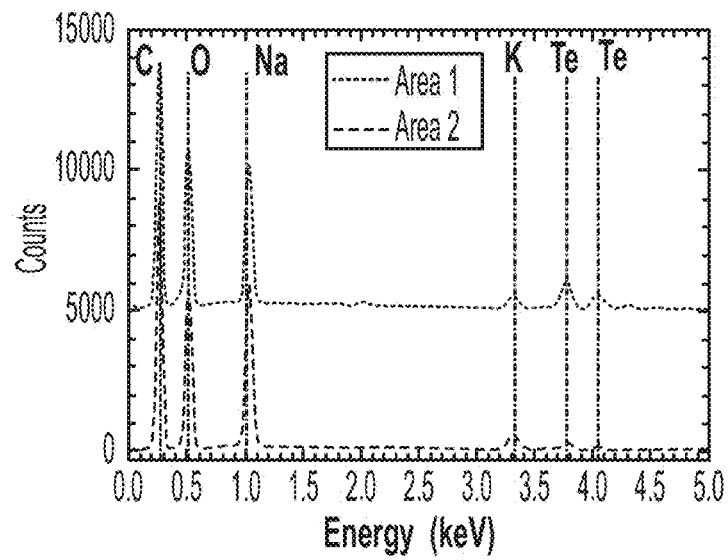
Figure 17D:
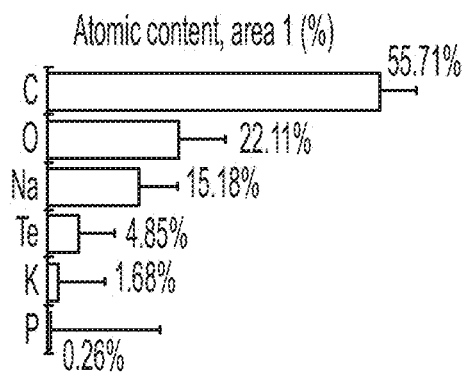
Figure 17E:
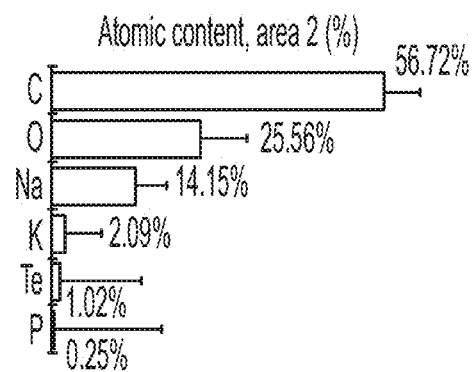
Figure 18A:
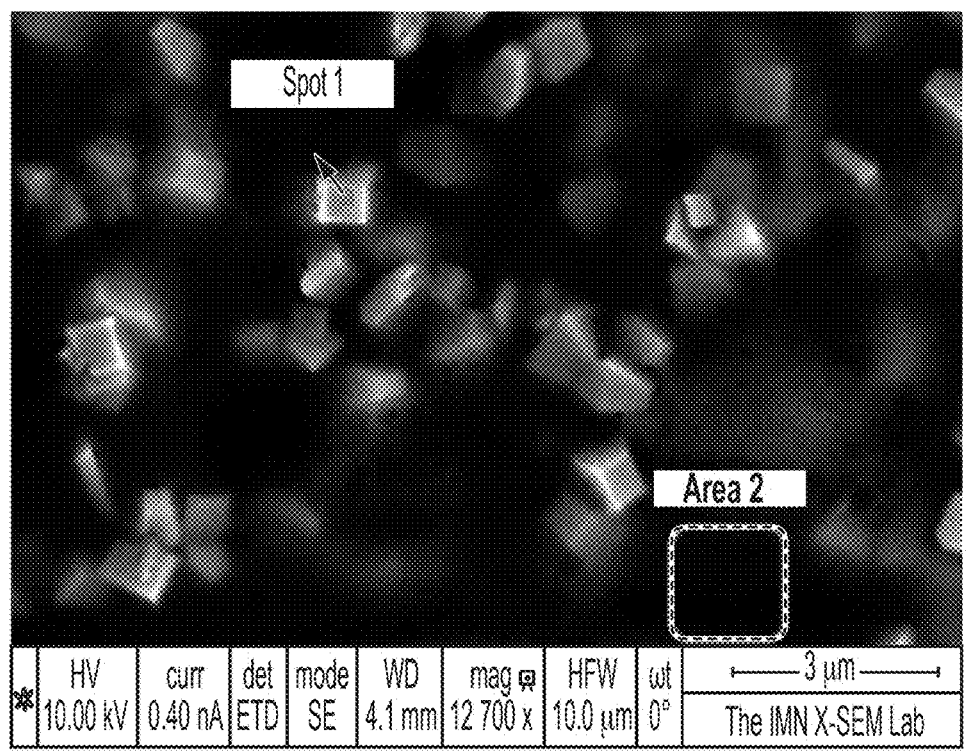
FIGS. 18A-E are characterization of LEM-TeNPs, showing the presence of tellurium within the sample, as well as carbon, oxygen and sodium. The spectra were taken in different zones: Spot 1 corresponds to one of the big tellurium crystals found in the sample and Area 2 corresponds to the surrounding organic matter, where the small dispersed nanoparticles are confirmed to be made of tellurium.
Figure 18B:
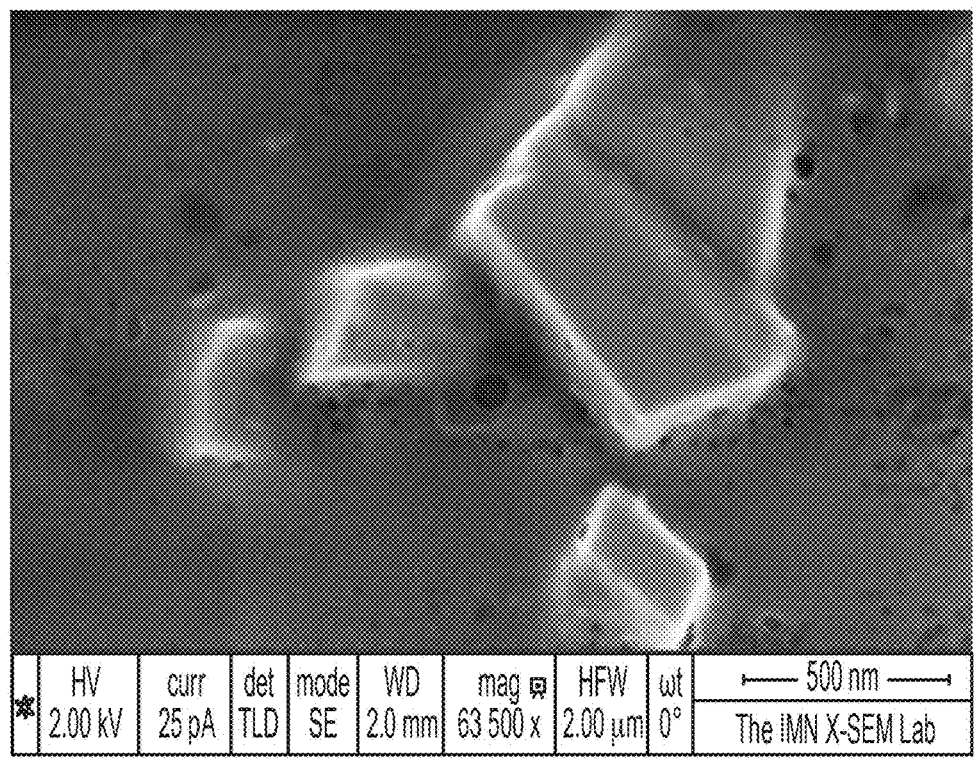
Figure 18C:
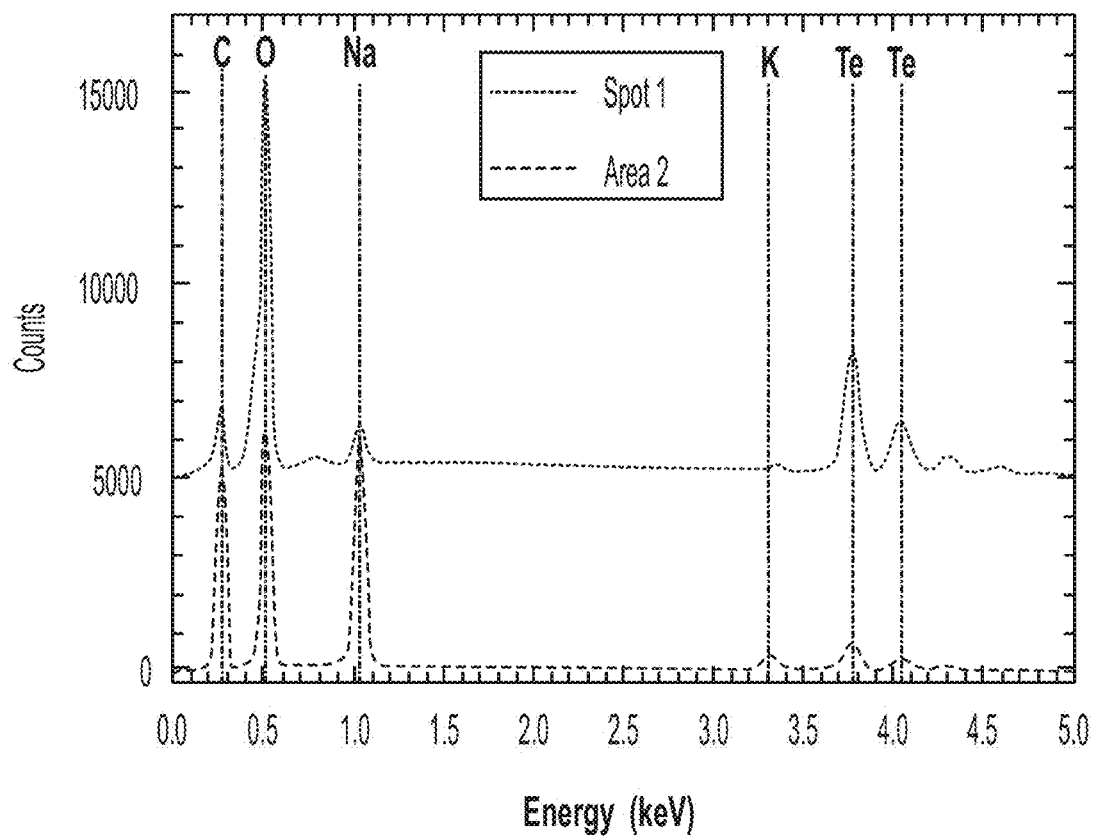
Figure 18D:
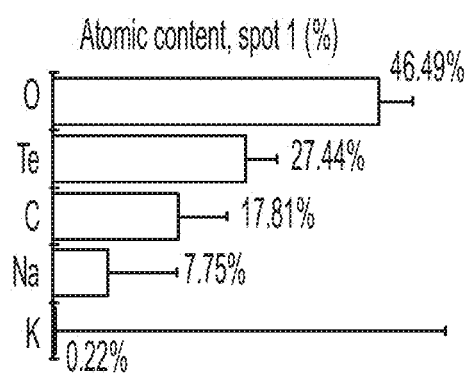
Figure 18E:
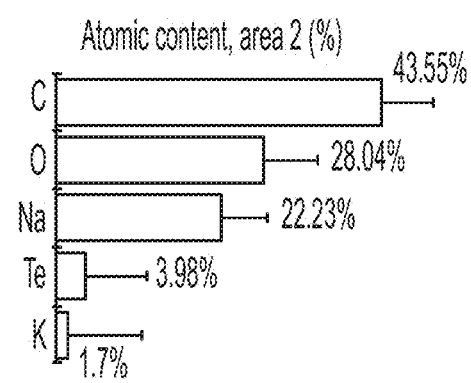
Figure 19A:
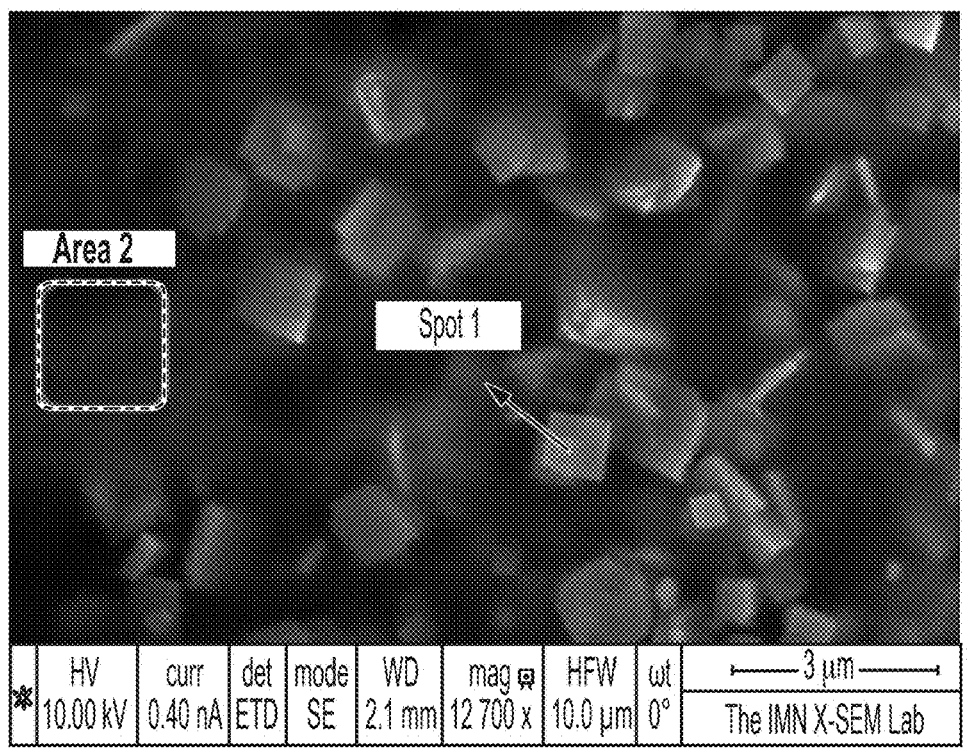
FIGS. 19A-E are characterization of LIM-TeNPs, showing the presence of tellurium within the sample, as well as carbon, oxygen and sodium. The spectra were taken in different zones: Spot 1 corresponds to one of the cubic tellurium crystals found in the sample and Area 2 corresponds to the surrounding organic matter, where the small dispersed nanoparticles are confirmed to be made of tellurium.
Figure 19B:
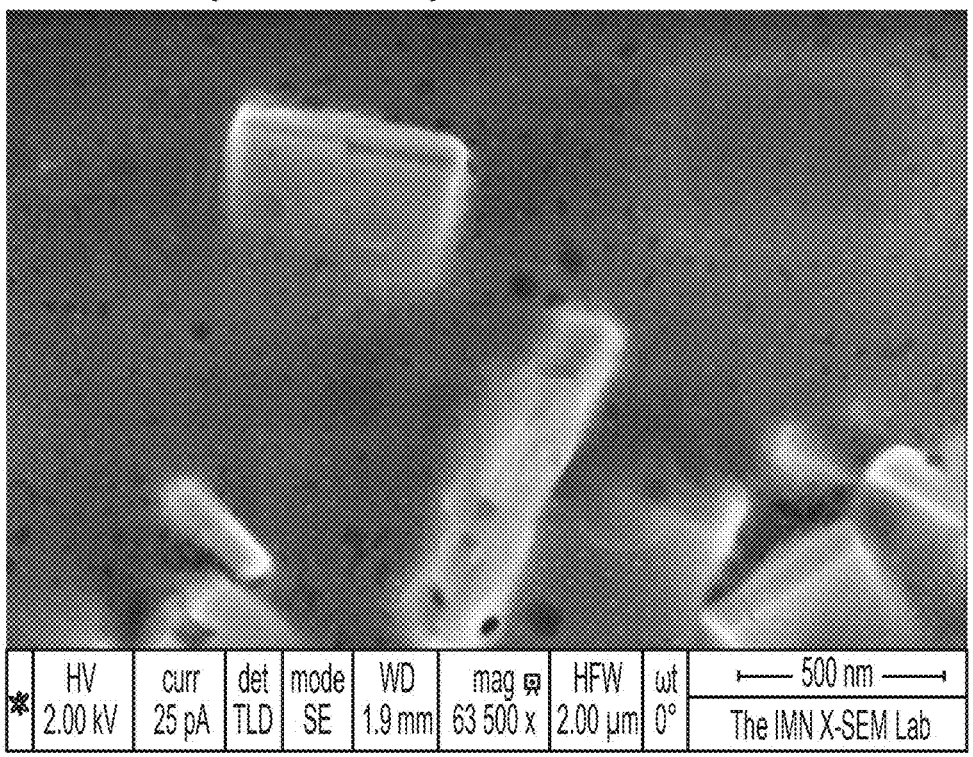
Figure 19C:
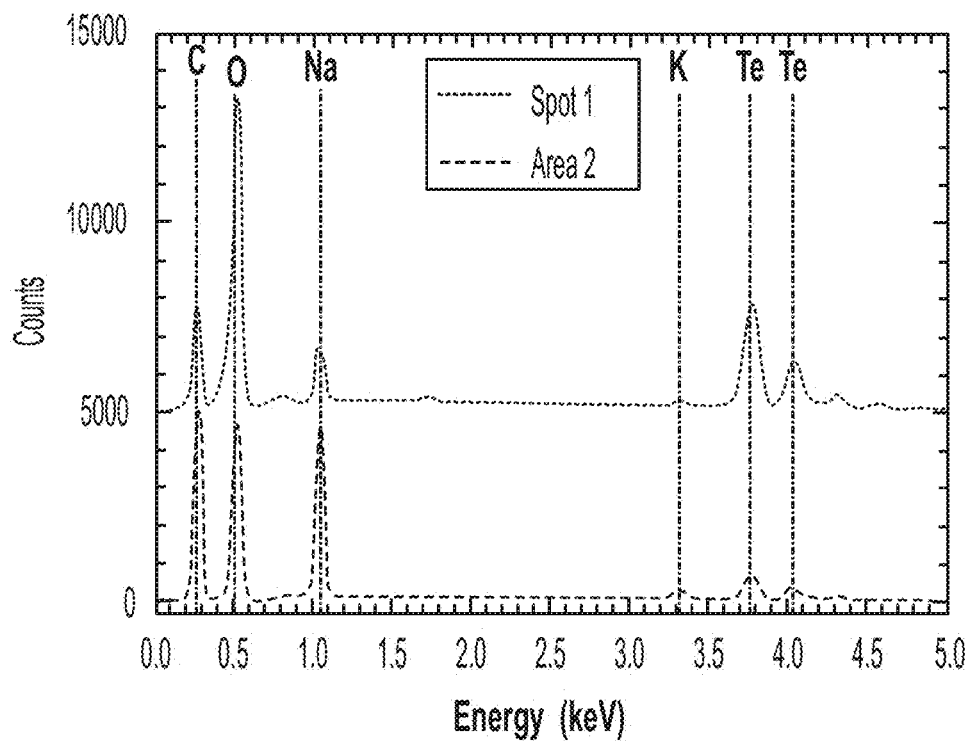
Figure 19D:
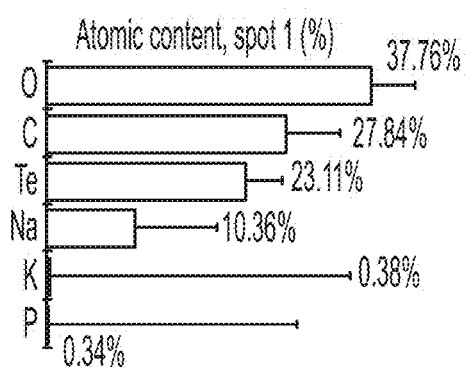
Figure 19E:
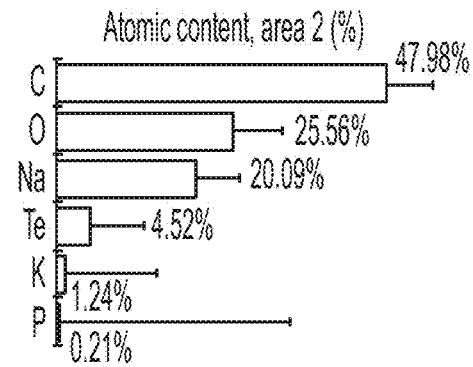

In order to verify the stability of the citrics-mediated Te nanoparticles synthesized using a metal precursor concentration of 50 mM, TEM imaging on the samples after 60 days of synthesis were carried out (FIGS. 21A-C). In general, it is evident that the samples kept their original morphologies and features. For example, the 60-days old OR-TeNPs sample is composed of partial agglomerated thin nanoneedles (50-200 nm length and 2-15 nm wide), as seen in FIG. 21A. These features are in accordance with the freshly synthesized OR-TeNPs sample (FIGS. 1A and 14C). In the case of 60-days old LEM- and LIM-TeNPs samples, agglomerated nanocubes with 100-200 nm in length were observed (FIGS. 21B and 21D, respectively), which is in agreement with their corresponding initial samples (FIGS. 1B and 1C, respectively).

The stability analysis through the measurement of the zeta-potential (Z-potential) of the freshly synthesized and 60-days old Te-based nanoparticle colloids were also carried out. In general, a colloid or suspension is considered stable if the Z-potential is above ±30 mV.[8] Given the measured Z-potential values for the colloids OR-, LEM- and LIM-TeNPs (freshly and 60-days old samples, see Table 6), they can be considered stable.

TABLE 6

Zeta-potential values for freshly and 60-days old OR-, LEM- and LIM-TeNPs. The pH of the colloids were 7.0 ±

| Type of NP | Z-potential (mV) As-synthesized | Z-potential (mV) 60 days-old |
|---|---|---|
| OR-TeNPs | −27.06 ± 0.28 | −29.11 ± 0.09 |
| LEM-TeNPs | −23.66 ± 0.98 | −26.12 ± 1.01 |
| LIM-TeNPs | −30.18 ± 1.84 | −28.39 ± 2.2 |

Antimicrobial Activity of TeNPs

The antimicrobial activity of the different Te nanostructures was evaluated using 24-hours growth curve analysis, with results are displayed in FIGS. 22A-F.

Figure 23B:
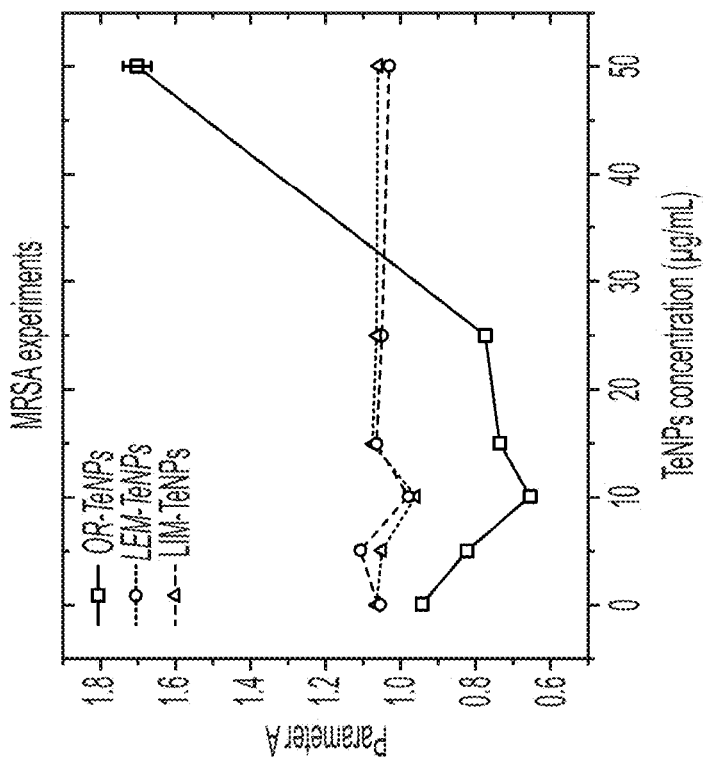
FIGS. 23A-F show Gompertz parameters evaluation. The Gompertz parameters have been evaluated for the different nanoparticles (OR-, LEM- and LIM-TeNPs) in experiments with *Escherichia coli* (FIGS. 23A, 23C, and 23E) and *Staphylococcus aureus* (FIGS. 23B, 23D, and 23F). Data=mean+/−SEM.
Figure 23A:
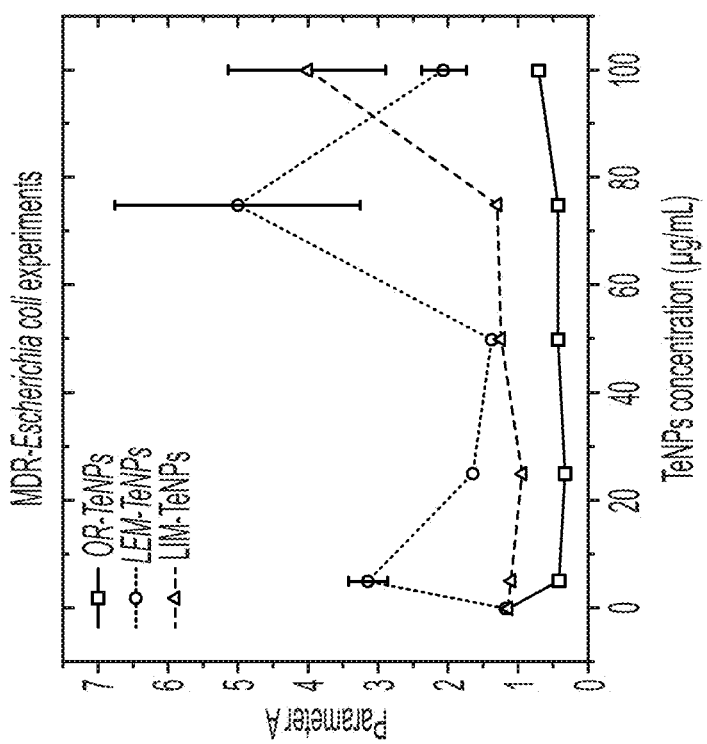

The parameters in the Gompertz equation were calculated and plotted for analysis for the three Te nanosystems. The parameter A represents the maximum specific growth of the bacteria under experimental conditions. Upon analysis of this parameter, it was found that a larger Te nanoparticle concentration led to lower asymptotic absorbance values (FIGS. 23A and 23B). The antibacterial activity was especially noticeable in the case of MDR E. coli (FIG. 23A). The bigger decay in asymptotic absorbance was found in the treatment with these bacteria. In general, the OR-TeNPs displayed an antibacterial effect for both Gram-positive and -negative bacteria.

Figure 23D:
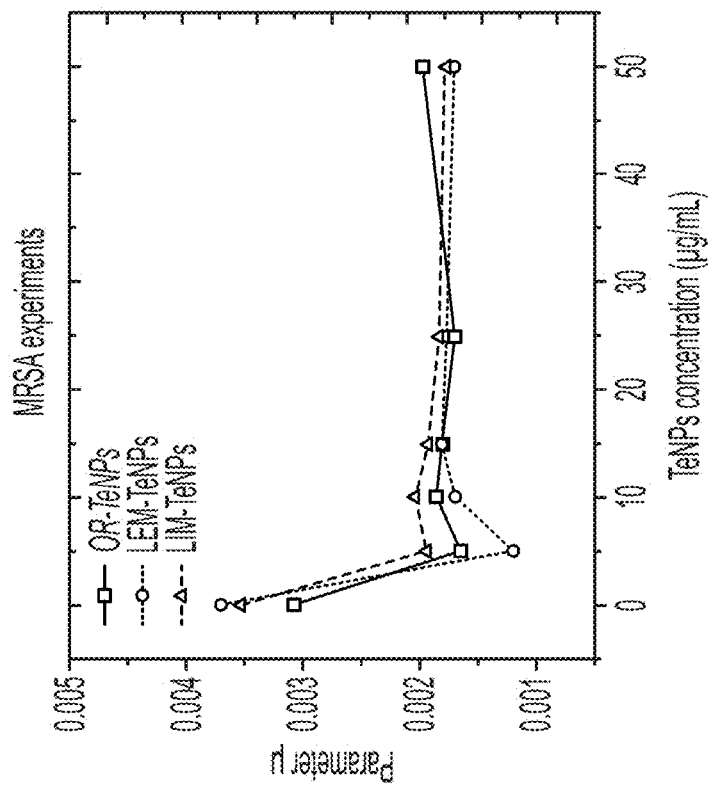
Figure 23C:
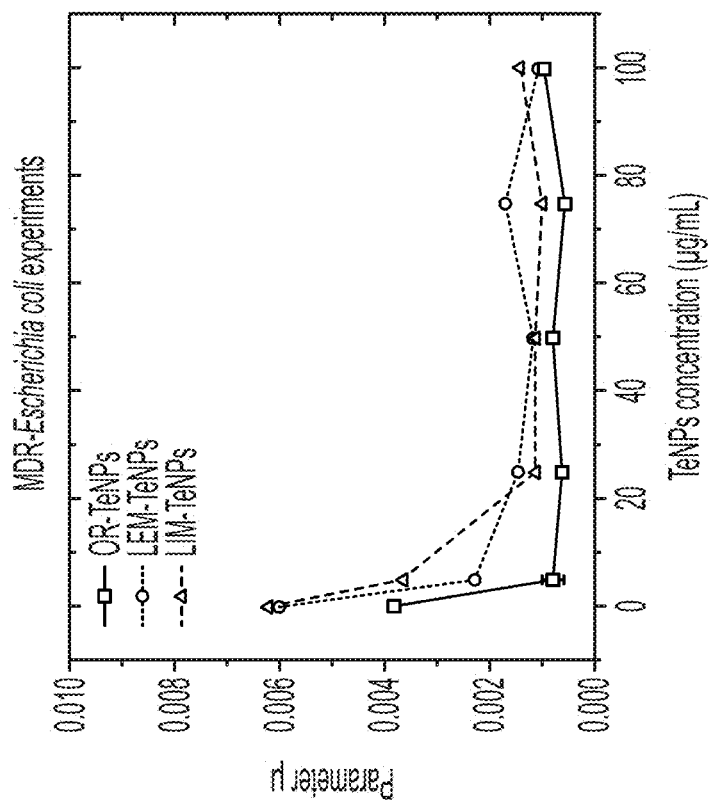
Figure 23F:
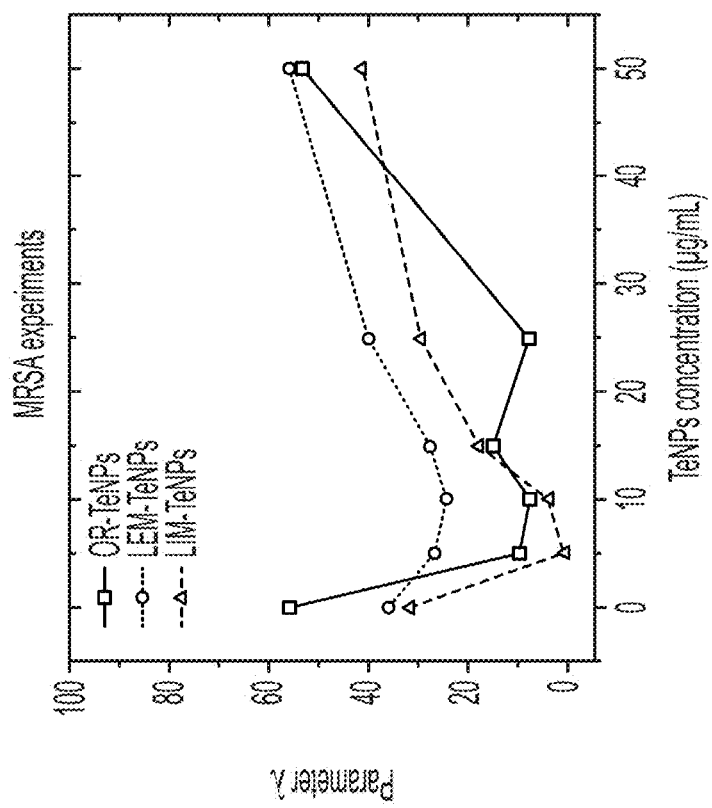
Figure 23E:
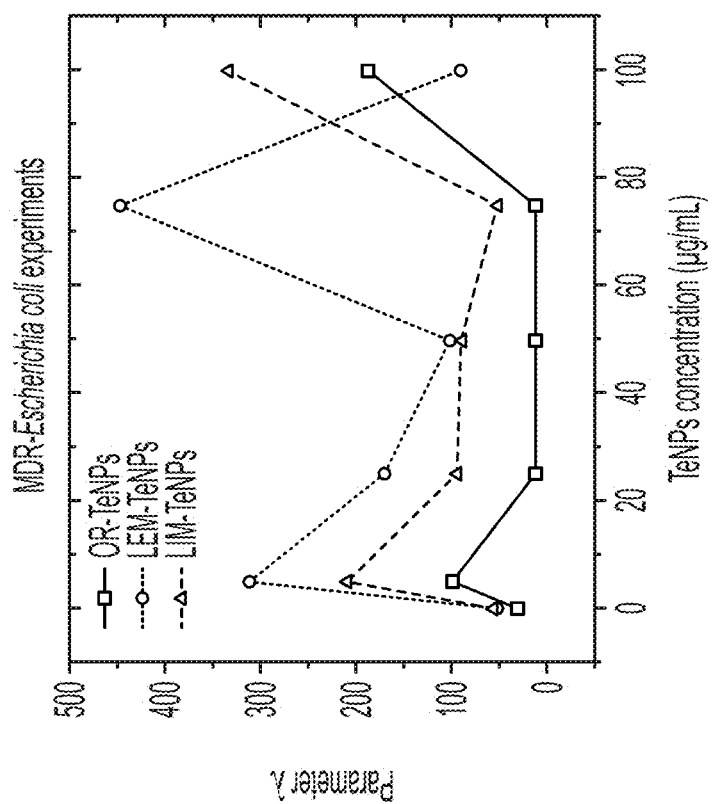

The maximum value of growth speed by the bacteria was analyzed using the parameter μ (FIGS. 23C and 23D). The plots demonstrated that larger TeNP concentrations resulted in lower maximum values reached for the bacteria; again, this was especially visible in the experiments with MDR Escherichia coli (FIG. 23C). Finally, the parameter λ that represents the lag time in the bacterial growth under experimental conditions was analyzed, and results are shown in FIGS. 23E and 23F. Results showed that a higher TeNP concentration led to a shorter lag phase for bacterial growth. This was especially visible in the experiments with MDR Escherichia coli (FIG. 23E), however, this trend was less obvious in the experiments with MRSA (FIG. 23F). Since the lag phase refers to the point where bacteria are adapting themselves to the growth conditions offered by the media with nanoparticles, the delay may mean that the nanoparticles delay the maturing of bacteria, which are then unable to proliferate the way they should. The presence of nanoparticles may affect the bacterial growth cycle through the synthesis of RNA, enzymes or other molecules involved in this phase, which will need to be assessed in future studies.

REFERENCES

1 C. L. Ventola, The Antibiotic Resistance Crisis: Part 1: Causes and Threats, Pharm. Ther., 2015, 40(4), 277-283.
2 S. Bin Zaman, M. A. Hussain, R. Nye, V. Mehta, K. T. Mamun and N. Hossain, A Review on Antibiotic Resistance: Alarm Bells Are Ringing, Cureus, 2017, 9(6), e1403, DOI: 10.7759/cureus.1403.
3 B. Li and T. J. Webster, Bacteria Antibiotic Resistance: New Challenges and Opportunities for Implant-Associated Orthopedic Infections, J. Orthop. Res., 2017, 36(1), 22-32, DOI: 10.1002/jor.23656.
4 G. Housman, S. Byler, S. Heerboth, K. Lapinska, M. Longacre, N. Snyder and S. Sarkar, Drug Resistance in Cancer: An Overview, Cancers, 2014, 6(3), 1769-1792, DOI: 10.3390/cancers6031769.
5 R. L. Siegel, K. D. Miller and A. Jemal, Cancer Statistics, 2018, Ca-Cancer J. Clin., 2018, 68(1), 7-30, DOI: 10.3322/caac.21442.
6 R. P. Kulkarni, Nano-Bio-Genesis: Tracing the Rise of Nanotechnology and Nanobiotechnology as "Big Science", J. Biomed. Discovery Collab., 2007, 2, 3, DOI: 10.1186/1747-5333-2-3.
7 C. L. Ventola, The Nanomedicine Revolution: Part 1: Emerging Concepts, Pharm. Ther., 2012, 37(9), 512-525.
8 L. Y. Rizzo, B. Theek, G. Storm, F. Kiessling and T. Lammers, Recent Progress in Nanomedicine: Therapeutic, Diagnostic and Theranostic Applications, Curr. Opin. Biotechnol., 2013, 24(6), 1159-1166, DOI: 10.1016/j.copbio.2013.02.020.
9 S. K. Murthy, Nanoparticles in Modern Medicine: State of the Art and Future Challenges, Int. J. Nanomed., 2007, 2(2), 129-141.
10 O. Salata, Applications of Nanoparticles in Biology and Medicine, J. Nanobiotechnol., 2004, 2(1), 3, DOI: 10.1186/1477-3155-2-3.
11 C. E. Escárcega-Gonzalez, J. A. Garza-Cervantes, A. Vazquez-Rodríguez, L. Z. Montelongo-Peralta, M. T. Trevino-Gonzalez, E. Diaz Barriga Castro, E. M. Saucedo-Salazar, R. M. Chávez Morales, D. I. Regalado-Soto, F. M. Treviño-Gonzalez, et al., In Vivo Antimicrobial Activity of Silver Nanoparticles Produced via a Green Chemistry Synthesis Using Acacia Rigidula as a Reducing and Capping Agent, Int. J. Nanomed., 2018, 13, 2349-2363, DOI: 10.2147/IJN. S160605.

12 R. Arvizo, R. Bhattacharya and P. Mukherjee, Gold Nanoparticles: Opportunities and Challenges in Nanomedicine, Expert Opin. Drug Delivery, 2010, 7(6), 753-763, DOI: 10.1517/17425241003777010.

13 J. Bogdan, J. Pławińska-Czarnak and J. Zarzyńska, Nanoparticles of Titanium and Zinc Oxides as Novel Agents in Tumor Treatment: A Review, Nanoscale Res. Lett., 2017, 12(1), 225, DOI: 10.1186/s11671-017-2007-y.

14 J. Jiang, J. Pi and J. Cai, The Advancing of Zinc Oxide Nanoparticles for Biomedical Applications, Bioinorg. Chem. Appl., 2018, 2018, 1-18, DOI: 10.1155/2018/1062562.

15 L. Tang and J. Cheng, Nonporous Silica Nanoparticles for Nanomedicine Application, Nano Today, 2013, 8(3), 290-312, DOI: 10.1016/INANTOD.2013.04.007.

16 T. Yamashita, K. Yamashita, H. Nabeshi, T. Yoshikawa, Y. Yoshioka, S.-I. Tsunoda and Y. Tsutsumi, Carbon Nanomaterials: Efficacy and Safety for Nanomedicine, Materials, 2012, 5(2), 350-363, DOI: 10.3390/ma5020350.

17 Y. Zhao, Q. Sun, X. Zhang, J. Baeyens and H. Su, Self-Assembled Selenium Nanoparticles and Their Application in the Rapid Diagnostic Detection of Small Cell Lung Cancer Biomarkers, Soft Matter, 2018, 14(4), 481-489, DOI:10.1039/c7sm01687e.

18 B. Hosnedlova, M. Kepinska, S. Skalickova, C. Fernandez, B. Ruttkay-Nedecky, Q. Peng, M. Baron, M. Melcova, R. Opatrilova, J. Zidkova, et al., Nano-Selenium and Its Nanomedicine Applications: A Critical Review, Int. J. Nanomed., 2018, 13, 2107-2128, DOI: 10.2147/IJN.5157541.

19 E. Zonaro, S. Lampis, R. J. Turner, S. J. S. Qazi and G. Vallini, Biogenic Selenium and Tellurium Nanoparticles Synthesized by Environmental Microbial Isolates Efficaciously Inhibit Bacterial Planktonic Cultures and Biofilms, Front. Microbiol., 2015, 6, 584, DOI: 10.3389/fmicb.2015.00584.

20 A. Fleming, On the Specific Antibacterial Properties of Penicillin and Potassium Tellurite. Incorporating a Method of Demonstrating Some Bacterial Antagonisms, J. Pathol. Bacteriol., 1932, 35(6), 831-842, DOI: 10.1002/path.1700350603.

21 A. Ramos-Ruiz, J. V. Wilkening, J. A. Field and R. Sierra-Alvarez, Leaching of Cadmium and Tellurium from Cadmium Telluride (CdTe) Thin-Film Solar Panels under Simulated Landfill Conditions, J. Hazard. Mater., 2017, 336, 57-64, DOI: 10.1016/j.jhazmat.2017.04.052.

22 J. D. Poplawsky, W. Guo, N. Paudel, A. Ng, K. More, D. Leonard and Y. Yan, Structural and Compositional Dependence of the CdTe x Se1-x Alloy Layer Photoactivity in CdTe-Based Solar Cells, Nat. Commun., 2016, 7(1), 12537, DOI: 10.1038/ncomms12537.

23 R. C. Molina-Quiroz, C. M. Muñoz-Villagrán, E. de la Torre, J. C. Tantaleán, C. C. Vásquez and J. M. Pérez-Donoso, Enhancing the Antibiotic Antibacterial Effect by Sub Lethal Tellurite Concentrations: Tellurite and Cefotaxime Act Synergistically in Escherichia Coli, PLoS One, 2012, 7(4), e35452, DOI: 10.1371/journal.pone.0035452.

24 J. M. Pérez, I. L. Calderón, F. A. Arenas, D. E. Fuentes, G. A. Pradenas, E. L. Fuentes, J. M. Sandoval, M. E. Castro, A. O. Elias and C. C. Vásquez, Bacterial Toxicity of Potassium Tellurite: Unveiling an Ancient Enigma, PLoS One, 2007, 2(2), e211, DOI: 10.1371/journal.pone.0000211.

25 J. Liu, C. Liang, X. Zhu, Y. Lin, H. Zhang and S. Wu, Understanding the Solvent Molecules Induced Spontaneous Growth of Uncapped Tellurium Nanoparticles, Sci. Rep., 2016, 6, 32631, DOI: 10.1038/srep32631.

26 P. C. Ray, H. Yu and P. P. Fu, Toxicity and Environmental Risks of Nanomaterials: Challenges and Future Needs, J. Environ. Sci. Health, Part C: Environ. Carcinog. Ecotoxicol. Rev., 2009, 27(1), 1-35, DOI: 10.1080/10590500802708267.

27 S. Mukherjee and C. R. Patra, Biologically Synthesized Metal Nanoparticles: Recent Advancement and Future Perspectives in Cancer Theranostics, Future Sci. OA, 2017, 3(3), F50203, DOI: 10.4155/fsoa-2017-0035.

28 F. Salamanca-Buentello, D. L. Persad, E. B. Court, D. K. Martin, A. S. Daar and P. A. Singer, Nanotechnology and the Developing World, PLoS Med., 2005, 2(5), e97, DOI:10.1371/journal.pmed.0020097.

29 I. Iavicoli, V. Leso, W. Ricciardi, L. L. Hodson and M. D. Hoover, Opportunities and Challenges of Nanotechnology in the Green Economy, Environ. Health, 2014, 13(1), 78, DOI: 10.1186/1476-069X-13-78.

30 M. de la Guardia, The Challenges of Green Nanotechnology, BioImpacts, 2014, 4(1), 1-2, DOI: 10.5681/bi.2014.009.

31 V. V. Makarov, A. J. Love, O. V. Sinitsyna, S. S. Makarova, I. V. Yaminsky, M. E. Taliansky and N. O. Kalinina, 'Green', Nanotechnologies: Synthesis of Metal Nanoparticles Using Plants, Acta Nat., 2014, 6(1), 35-44.

32 Y.-J. Kim, R. Mathiyalagan, J. Markus, C. Wang, P. Singh, S. Ahn, M. E.-A. Farh, D. C. Yang and R. Abbai, Green Synthesis of Multifunctional Silver and Gold Nanoparticles from the Oriental Herbal Adaptogen: Siberian Ginseng, Int. J. Nanomed., 2016, 11, 3131-3143, DOI: 10.2147/IJN.S108549.

33 D. Medina Cruz, G. Mi and T. J. Webster, Synthesis and Characterization of Biogenic Selenium Nanoparticles with Antimicrobial Properties Made by Staphylococcus Aureus, Methicillin-Resistant Staphylococcus Aureus (MRSA), Escherichia Coli, and Pseudomonas Aeruginosa, J. Biomed. Mater. Res., Part A, 2018, 106(5), 1400-1412, DOI: 10.1002/jbm.a.36347.

34 F. Niknejad, M. Nabili, R. Daie Ghazvini and M. Moazeni, Green synthesis of silver nanoparticles: Advantages of the yeast, Curr. Med. Mycol., 2015, 1(3), 17-24, DOI: 10.18869/acadpub.cmm.1.3.17.

35 P. Velusamy, G. V. Kumar, V. Jeyanthi, J. Das and R. Pachaiappan, Bio-Inspired Green Nanoparticles: Synthesis, Mechanism, and Antibacterial Application, Toxicol. Res., 2016, 32(2), 95-102, DOI: 10.5487/TR.2016.32.2.095.

36 L. Wu, X. Cai, K. Nelson, W. Xing, J. Xia, R. Zhang, A. J. Stacy, M. Luderer, G. M. Lanza, L. V. Wang, et al., A Green Synthesis of Carbon Nanoparticles from Honey and Their Use in Real-Time Photoacoustic Imaging, Nano Res., 2013, 6(5), 312-325, DOI: 10.1007/s12274-013-0308-8.

37 S. K. Nune, N. Chanda, R. Shukla, K. Katti, R. R. Kulkarni, S. Thilakavathi, S. Mekapothula, R. Kannan and K. V. Katti, Green Nanotechnology from Tea: Phytochemicals in Tea as Building Blocks for Production of Biocompatible Gold Nanoparticles, J. Mater. Chem., 2009, 19(19), 2912-2920, DOI: 10.1039/b822015h.

38 P. Singh, S. Pandit, J. Garnæs, S. Tunjic, V. Mokkapati, A. Sultan, A. Thygesen, A. Mackevica, R. V. Mateiu, A.

38 E. Daugaard, et al., Green Synthesis of Gold and Silver Nanoparticles from *Cannabis sativa* (Industrial Hemp) and Their Capacity for Biofilm Inhibition, Int. J. Nanomed., 2018, 13, 3571-3591, DOI: 10.2147/IJN.S157958.
39 J. H. Lee, M. C. Moon, J. Y. Lee and I. J. Yu, Challenges and Perspectives of Nanoparticle Exposure Assessment, Toxicol. Res., 2010, 26(2), 95-100, DOI: 10.5487/TR.2010.26.2.095.
40 B. Kong, J. H. Seog, L. M. Graham and S. B. Lee, Experimental Considerations on the Cytotoxicity of Nanoparticles, Nanomedicine, 2011, 6(5), 929-941, DOI: 10.2217/nnm.11.77.
41 H. Kelebek, S. Selli, A. Canbas and T. Cabaroglu, HPLC Determination of Organic Acids, Sugars, Phenolic Compositions and Antioxidant Capacity of Orange Juice and Orange Wine Made from a Turkish Cv. Kozan, Microchem. J., 2009, 91(2), 187-192, DOI: 10.1016/J.MICROC.2008.10.008.
42 K. L. Penniston, S. Y. Nakada, R. P. Holmes and D. G. Assimos, Quantitative Assessment of Citric Acid in Lemon Juice, Lime Juice, and Commercially-Available Fruit Juice Products, J. Endourol., 2008, 22(3), 567-570, DOI:10.1089/end.2007.0304.
43 A. H. Bennett and D. J. Tarbert, Vitamin C in Citrus Juices, Biochem. J., 1933, 27(4), 1294-1301.
44 D. Briggs, in Handbook of X-Ray Photoelectron Spectroscopy, ed. C. D. Wanger, W. M. Riggs, L. E. Davis, J. F. Moulder and G. E. Muilenberg, Perkin-Elmer Corp., Physical Electronics Division, Eden Prairie, Minn., USA, 1979. 190 Pp. $195, Surf. Interface Anal. 1981, 3(4), v-v, DOI:10.1002/sia.740030412.
45 R. R. Silva, H. A. G. Mejia, S. J. L. Ribeiro, L. K. Shrestha, K. Ariga, O. N. Oliveira Jr., V. R. Camargo, L. J. Q. Maia, C. B. Araújo, R. R. Silva, et al., Facile Synthesis of Tellurium Nanowires and Study of Their Third-Order Nonlinear Optical Properties, J. Braz. Chem. Soc., 2016, 28(1), 58-67, DOI: 10.5935/0103-5053.20160145.
46 M. H. Zwietering, I. Jongenburger, F. M. Rombouts and K. van't Riet, Modeling of the Bacterial Growth Curve, Appl. Environ. Microbiol., 1990, 56(6), 1875-1881.
47 H. Kim, Y. S. Seo, K. Kim, J. W. Han, Y. Park and S. Cho, Concentration Effect of Reducing Agents on Green Synthesis of Gold Nanoparticles: Size, Morphology, and Growth Mechanism, Nanoscale Res. Lett., 2016, 11(1), 230, DOI: 10.1186/s11671-016-1393-x.
48 C. Adenis, V. Langer and O. Lindqvist, Reinvestigation of the Structure of Tellurium, Acta Crystallogr., Sect. C: Cryst. Struct. Commun., 1989, 45(6), 941-942, DOI: 10.1107/S0108270188014453.
49 H. Beyer, Verfeinerung Der Kristallstruktur von Tellurit, Dem Rhomischen TeO2, Z. Kristallogr., 1967, 124, 228-237.
50 I. P. Kondratyuk, L. A. Muradyan, Y. V. Pisarevskii and V. I. Simonov, Precision X-Ray Structural Investigation of Acousto-Optical Single Crystals of α-TeO2, Kristallografiya, 1987, 32, 609.
51 J. F. Kefford, The Chemical Constituents of Citrus Fruits, Adv. Food Res., 1960, 9, 285-372, DOI: 10.1016/S0065-2628 (08)60278-5.
52 W. C. Scott, T. J. Kew and M. K. Veldhuis, Composition of Orange Juice Cloud, J. Food Sci., 1965, 30(5), 833-837, DOI: 10.1111/j.1365-2621.1965.tb01850.x.
53 C. E. Vandercook and R. G. Stephenson, Lemon Juice Composition. Identification of Major Phenolic Compounds and Estimation by Paper Chromatography, J. Agric. Food Chem., 1966, 14(5), 450-454, DOI: 10.1021/jf60147a003.
54 C. E. Vandercook, L. A. Rolle, H. L. Postlmayr and R. A. Utterberg, Lemon Juice Composition. V. Effects of Some Fruit Storage and Processing Variables on the Characterization of Lemon Juice, J. Food Sci., 1966, 31(1), 58-62, DOI: 10.1111/j.1365-2621.1966.tb15415.x.
55 K. V. Berezin, I. T. Shagautdinova, M. L. Chernavina, A. V. Novoselova, K. N. Dvoretskii and A. M. Likhter, The Experimental Vibrational Infrared Spectrum of Lemon Peel and Simulation of Spectral Properties of the Plant Cell Wall, Opt. Spectrosc., 2017, 123(3), 495-500, DOI: 10.1134/50030400X17090089.
56 G. Carotenuto, M. Palomba, S. De Nicola, G. Ambrosone and U. Coscia, Structural and Photoconductivity Properties of Tellurium/PMMA Films, Nanoscale Res. Lett., 2015, 10(1), 313, DOI: 10.1186/s11671-015-1007-z.
57 R. A. El-Mallawany, Theoretical and Experimental IR Spectra of Binary Rare Earth Tellurite Glasses-1, Infrared Phys., 1989, 29(2-4), 781-785, DOI: 10.1016/0020-0891 (89) 90125-5.
58 B. Zare, M. A. Faramarzi, Z. Sepehrizadeh, M. Shakibaie, S. Rezaie and A. R. Shahverdi, Biosynthesis and Recovery of Rod-Shaped Tellurium Nanoparticles and Their Bactericidal Activities, Mater. Res. Bull., 2012, 47(11), 3719-3725, DOI: 10.1016/J.MATERRESBULL.2012.06.034.
59 S. Pal, Y. K. Tak and J. M. Song, Does the Antibacterial Activity of Silver Nanoparticles Depend on the Shape of the Nanoparticle? A Study of the Gram-negative Bacterium *Escherichia Coli*, Appl. Environ. Microbiol., 2007, 73(6), 1712-1720, DOI: 10.1128/AEM.02218-06.
60 D. Zannoni, F. Borsetti, J. J. Harrison and R. J. Turner, The Bacterial Response to the Chalcogen Metalloids Se and Te, in Advances in Microbial Physiology, 2007, vol. 53, pp. 1-312, DOI: 10.1016/S0065-2911(07)53001-8.
61 J. Pi, F. Yang, H. Jin, X. Huang, R. Liu, P. Yang and J. Cai, Selenium Nanoparticles Induced Membrane Biomechanical Property Changes in MCF-7 Cells by Disturbing Membrane Molecules and F-Actin, Bioorg. Med. Chem. Lett., 2013, 23(23), 6296-6303, DOI: 10.1016/j.bmcl.2013.09.078.
62 D. Benedec, I. Oniga, F. Cuibus, B. Sevastre, G. Stiufiuc, M. Duma, D. Hanganu, C. Iacovita, R. Stiufiuc and C. M. Lucaciu, Origanum Vulgare Mediated Green Synthesis of Biocompatible Gold Nanoparticles Simultaneously Possessing Plasmonic, Antioxidant and Antimicrobial Properties, Int. J. Nanomed., 2018, 13, 1041-1058, DOI: 10.2147/IJN.S149819.
63 S. Gurunathan, J. Han, J. H. Park and J.-H. Kim, A Green Chemistry Approach for Synthesizing Biocompatible Gold Nanoparticles, Nanoscale Res. Lett., 2014, 9(1), 248, DOI: 10.1186/1556-276X-9-248.
64 L. A. Ba, M. Döring, V. Jamier and C. Jacob, Tellurium: An Element with Great Biological Potency and Potential, Org. Biomol. Chem., 2010, 8(19), 4203-4216, DOI: 10.1039/c00b00086h.
65 C. D. Brown, D. M. Cruz, A. K. Roy and T. J. Webster, Synthesis and Characterization of PVP-Coated Tellurium Nanorods and Their Antibacterial and Anticancer Properties, J. Nanopart. Res., 2018, 20(9), 254, DOI: 10.1007/s11051-018-4354-8.
66 X. Chen, Q. Lv, Y. Liu and W. Deng, Effect of Food Additive Citric Acid on The Growth of Human Esophageal Carcinoma Cell Line EC109, Cell J., 2017, 18(4), 493-502, DOI: 10.22074/CELLJ.2016.4716.

67 J. van der Reest and E. Gottlieb, Anti-Cancer Effects of Vitamin C Revisited, Cell Res., 2016, 26(3), 269-270, DOI: 10.1038/cr.2016.7.

68 P. Brenneisen and A. Reichert, Nanotherapy and Reactive Oxygen Species (ROS) in Cancer: A Novel Perspective, Antioxidants, 2018, 7(2), 31, DOI: 10.3390/antiox7020031.

69 A. Hafeez and I. Kazmi, Dacarbazine Nanoparticle Topical Delivery System for the Treatment of Melanoma, Sci. Rep., 2017, 7(1), 16517, DOI: 10.1038/s41598-017-16878-1.

70 Dacarbazine Prices, Coupons & Patient Assistance Programs-Drugs.com, https://www.drugs.com/price-guide/dacarbazine (accessed Dec. 24, 2018).

71 United States Department of Agriculture National Agricultural Statistics Service.

72 A. Gupta, J. Zhuo, J. Zha, S. Reddy, J. Olp and A. Pai, Effect of Different Intravenous Iron Preparations on Lymphocyte Intracellular Reactive Oxygen Species Generation and Subpopulation Survival, BMC Nephrol., 2010, 11, 16, DOI: 10.1186/1471-2369-11-16.

73 H. Sun, J. Jia, C. Jiang and S. Zhai, Gold Nanoparticle-Induced Cell Death and Potential Applications in Nanomedicine, Int. J. Mol. Sci., 2018, 19(3), 754, DOI: 10.3390/ijms19030754.

74 S. Burattini and E. Falcieri, Analysis of Cell Death by Electron Microscopy, in Methods in molecular biology, Clifton, N.J., 2013, vol. 1004, pp. 77-89, DOI: 10.1007/978-1_62703-383-1-7.

75 D. J. Taatjes, B. E. Sobel and R. C. Budd, Morphological and Cytochemical Determination of Cell Death by Apoptosis, Histochem. Cell Biol., 2008, 129(1), 33-43, DOI: 10.1007/s00418-007-0356-9.

76 S. Elmore, Apoptosis: A Review of Programmed Cell Death, Toxicol. Pathol., 2007, 35(4), 495-516, DOI: 10.1080/01926230701320337.

REFERENCES FOR SUPPLEMENTARY INFORMATION

1 D'Elia, L.; Barba, G.; Cappuccio, F. P.; Strazzullo, P. Potassium Intake, Stroke, and Cardiovascular Disease. J. Am. Coll. Cardiol. 2011, 57 (10), 1210-1219. https://doi.org/10.1016/j.jacc.2010.09.070.

2 Adenis, C.; Langer, V.; Lindqvist, O. Reinvestigation of the Structure of Tellurium. Acta Crystallogr. Sect. C Cryst. Struct. Commun. 1989, 45 (6), 941-942. https://doi.org/10.1107/50108270188014453.

3 Beyer, H. Verfeinerung Der Kristallstruktur von Tellurit, Dem Rhomischen TeO2. Zeitschrift fur Krist. 1967, 124, 228-237.

4 Beamson, G.; Briggs, D. High Resolution XPS of Organic Polymers: The Scienta ESCA300 Database. J. Chem. Educ. 1993, 70 (1), A25. https://doi.org/10.1021/ed070pA25.5.

5 Nevshupa, R.; Martínez, L.; Álvarez, L.; López, M. F.; Huttel, Y.; Méndez, J.; Román, E. Influence of Thermal Ageing on Surface Degradation of Ethylene-Propylene-Diene Elastomer. J. Appl. Polym. Sci. 2011, 119 (1), 242-251. https://doi.org/10.1002/app.32519.

6 Briggs, D. Handbook of X-Ray Photoelectron Spectroscopy C. D. Wanger, W. M. Riggs, L. E. Davis, J. F. Moulder and G. E. Muilenberg Perkin-Elmer Corp., Physical Electronics Division, Eden Prairie, Minn., USA, 1979. 190 Pp. $195. Surf. Interface Anal. 1981, 3 (4), v-v. https://doi.org/10.1002/sia.740030412.

7 Silva, R. R.; Mejia, H. A. G.; Ribeiro, S. J. L.; Shrestha, L. K.; Ariga, K.; Oliveira Jr., O. N.; Camargo, V. R.; Maia, L. J. Q.; Araújo, C. B.; Silva, R. R.; et al. Facile Synthesis of Tellurium Nanowires and Study of Their Third-Order Nonlinear Optical Properties. J. Braz. Chem. Soc. 2016, 28 (1), 58-67. https://doi.org/10.5935/0103-5053.20160145.

8 Liu, J.; Liang, C.; Zhu, X.; Lin, Y.; Zhang, H.; Wu, S. Understanding the Solvent Molecules Induced Spontaneous Growth of Uncapped Tellurium Nanoparticles. Sci. Rep. 2016, 6, 32631. https://doi.org/10.1038/srep32631.

INCORPORATION BY REFERENCE; EQUIVALENTS

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of making a tellurium nanomaterial, the method comprising:
   a) combining a juice from rag and pulp of a citrus fruit with a tellurium salt to form a mixture comprising the juice with dissolved tellurium salt, wherein the dissolved tellurium salt has a concentration from 25 mM to 100 mM, and wherein the tellurium salt is sodium tellurite ($Na_2TeO_3$), sodium tellurate ($Na_2TeO_4$), potassium tellurate ($K_2TeO_4$), potassium tellurate hydrate ($K_2TeO_4.H_2O$), potassium tellurite ($K_2TeO_3$), telluric acid ($Te(OH)_6$), or tellurium tetrachloride ($TeCl_4$); and
   b) heating the mixture comprising the juice with dissolved tellurium salt, thereby making the tellurium nanomaterial, wherein the tellurium nanomaterial has a length from about 50 nm to about 200 nm.

2. The method of claim 1, wherein the citrus fruit is an orange, a lemon, or a lime.

3. The method of claim 1, wherein the tellurium salt is $Na_2TeO_3$.

4. The method of claim 1, wherein the tellurium salt is dissolved in a solvent prior to combining the juice with the tellurium salt.

5. The method of claim 4, wherein the solvent is water.

6. The method of claim 1, further comprising centrifuging the tellurium nanomaterial.

7. The method of claim 1, wherein heating the mixture comprising the juice with dissolved tellurium salt is performed by microwave heating.

8. The method of claim 1, wherein heating the mixture comprising the juice with dissolved tellurium salt comprises heating to a temperature from about 25° C. to about 100° C.

* * * * *

UNITED STATES PATENT AND TRADEMARK OFFICE
CERTIFICATE OF CORRECTION

PATENT NO. : 11,559,556 B2
APPLICATION NO. : 16/817856
DATED : January 24, 2023
INVENTOR(S) : David Medina Cruz et al.

It is certified that error appears in the above-identified patent and that said Letters Patent is hereby corrected as shown below:

In the Claims

In Claim 1, Column 34, Line 40, delete "($K_2TeO_4.H_2O$)" and insert -- ($K_2TeO_4 \cdot H_2O$) --.

Signed and Sealed this
Twenty-eighth Day of March, 2023

Katherine Kelly Vidal
*Director of the United States Patent and Trademark Office*